United States Patent
Steuernagel et al.

(10) Patent No.: US 8,921,304 B2
(45) Date of Patent: Dec. 30, 2014

(54) MODIFIED UBIQUITIN PROTEINS HAVING A SPECIFIC BINDING ACTIVITY FOR THE EXTRADOMAIN B OF FIBRONECTIN

(75) Inventors: Arnd Steuernagel, Goettingen (DE); Erik Fiedler, Halle/Saale (DE); Markus Fiedler, Halle/Saale (DE); Anja Kunert, Halle/Saale (DE); Joerg Nerkamp, Halle/Saale (DE); Thomas Goettler, Halle/Saale (DE); Manja Gloser, Teutschenthal (DE); Ilka Haenssgen, Halle/Saale (DE)

(73) Assignee: Scil Proteins GmbH, Halle/Saale ( * ) Notice: Subject to any disclaimer, the term of this patent is extended or adjusted under 35 U.S.C. 154(b) by 0 days.

(21) Appl. No.: 13/142,195

(22) PCT Filed: Dec. 14, 2010

(86) PCT No.: PCT/EP2010/069665
§ 371 (c)(1),
(2), (4) Date: Sep. 27, 2012

(87) PCT Pub. No.: WO2011/073208
PCT Pub. Date: Jun. 23, 2011

(65) Prior Publication Data
US 2013/0011334 A1    Jan. 10, 2013

(30) Foreign Application Priority Data

Dec. 14, 2009 (EP) .................................. 09179147
May 7, 2010 (EP) .................................. 10162264
Oct. 8, 2010 (EP) .................................. 10186980

(51) Int. Cl.
| | | |
|---|---|---|
| A61K 38/00 | (2006.01) |
| C07K 14/00 | (2006.01) |
| C12N 15/10 | (2006.01) |
| C07K 14/47 | (2006.01) |
| C07K 14/435 | (2006.01) |
| C07K 14/525 | (2006.01) |
| G01N 33/68 | (2006.01) |

(52) U.S. Cl.
CPC ........ *C12N 15/1034* (2013.01); *C12N 15/1041* (2013.01); *G01N 33/6878* (2013.01); *C12N 15/1044* (2013.01); *C07K 14/47* (2013.01); *G01N 33/6845* (2013.01); *C12N 15/1037* (2013.01); *C07K 14/435* (2013.01); *C07K 2319/95* (2013.01); *C07K 14/525* (2013.01); *C07K 2319/31* (2013.01)
USPC ............................................ 514/1.1; 530/350

(58) Field of Classification Search
None
See application file for complete search history.

(56) References Cited

U.S. PATENT DOCUMENTS

| | | |
|---|---|---|
| 4,873,192 A | 10/1989 | Kunkel |
| 5,789,166 A | 8/1998 | Bauer et al. |
| 5,958,684 A | 9/1999 | Van Leeuwen et al. |
| 6,569,677 B1 | 5/2003 | Legrand et al. |
| 6,673,901 B2 | 1/2004 | Koide |
| 6,799,121 B2 | 9/2004 | Chu et al. |
| 7,250,297 B1 | 7/2007 | Beste et al. |
| 7,601,803 B1 | 10/2009 | Fiedler et al. |
| 7,838,629 B2 | 11/2010 | Fiedler et al. |
| 2003/0045681 A1 | 3/2003 | Neri et al. |
| 2003/0073623 A1 | 4/2003 | Drmanac et al. |
| 2004/0043386 A1 | 3/2004 | Pray et al. |
| 2006/0058510 A1 | 3/2006 | Skerra et al. |
| 2006/0099686 A1 | 5/2006 | Fiedler et al. |
| 2007/0111287 A1 | 5/2007 | Fiedler et al. |
| 2007/0248536 A1 | 10/2007 | Fiedler et al. |
| 2008/0171851 A1 | 7/2008 | Fiedler et al. |
| 2010/0130720 A1 | 5/2010 | Schraeml et al. |
| 2013/0097737 A1 | 4/2013 | Kovalic et al. |

FOREIGN PATENT DOCUMENTS

| | | |
|---|---|---|
| AU | 2010332932 | 6/2011 |
| AU | 2010332938 | 6/2011 |
| FR | 2 761 688 A | 10/1998 |
| WO | WO97/16556 | 5/1997 |
| WO | WO97/45544 | 12/1997 |
| WO | WO98/54312 | 12/1998 |
| WO | WO99/58570 | 11/1999 |
| WO | WO01/04144 | 1/2001 |
| WO | WO01/62800 | 8/2001 |
| WO | WO2004/106368 | 12/2004 |
| WO | WO2005/044845 | 5/2005 |
| WO | WO2005/059131 | 6/2005 |
| WO | WO2006/040129 | 4/2006 |
| WO | WO2006/119897 | 11/2006 |
| WO | WO2007/054120 | 5/2007 |
| WO | WO2007/115837 | 10/2007 |
| WO | WO2007/128563 | 11/2007 |
| WO | WO2008/022759 | 2/2008 |

(Continued)

OTHER PUBLICATIONS

International Preliminary Report in Patentability corresponding to International Patent Application No. PCT/EP2010/069665 dated Jun. 19, 2012.
International Search Report corresponding to International Patent Application No. PCT/EP2010/069665 dated Apr. 13, 2011.
International Preliminary Report on Patentability corresponding to International Patent Application No. PCT/EP2010/069674 dated Jun. 28, 2012.
Notification Concerning Transmittal of International Preliminary Report on Patentability (Chapter I of the Patent Cooperation Treaty) corresponding to International Patent Application No. PCT/EP2010/069666 dated Jun. 28, 2012.

(Continued)

*Primary Examiner* — David J Steadman
*Assistant Examiner* — Paul Holland
(74) *Attorney, Agent, or Firm* — Jenkins, Wilson, Taylor & Hunt, P.A.

(57) ABSTRACT

The present invention refers to novel hetero-multimeric proteins obtained from modified ubiquitin capable of binding the extradomain B of fibronectin (ED-B) with high affinity. Furthermore, the invention refers to fusion proteins comprising said recombinant protein fused to a pharmaceutically and/or diagnostically active component. The invention is further directed to the use of said proteins in medical treatment methods.

9 Claims, 32 Drawing Sheets
(21 of 32 Drawing Sheet(s) Filed in Color)

(56) References Cited

FOREIGN PATENT DOCUMENTS

| WO | WO2008/059011 | 5/2008 |
|---|---|---|
| WO | WO2008/096012 | 8/2008 |
| WO | WO2011/073208 | 6/2011 |
| WO | WO2011/073209 | 6/2011 |
| WO | WO2011/073214 | 6/2011 |

OTHER PUBLICATIONS

Notification of Transmittal of the International Search Report and the Written Opinion of the International Searching Authority, or the Declaration corresponding to International Patent Application No. PCT/EP2010/069665 dated Apr. 13, 2011.
Abedi et al, "Green fluorescent protein as a scaffold for intracellular presentation of peptides," Nucleic Acids Research. vol. 26, No. 2 pp. 623-630 (1998).
Advisory Action corresponding to U.S. Appl. No. 10/030,605 dated Oct. 13, 2006.
Advisory Action corresponding to U.S. Appl. No. 12/072,959 dated May 18, 2010.
Advisory Action corresponding to U.S. Appl. No. 11/732,632 dated Jun. 30, 2010.
Baker et al., "Protein Expression Using Cotranslational Fusion and Cleavage of Ubiquitin," The Journal of Biological Chemistry. vol. 269, No. 41 pp. 25381-25386 (1994).
Beal et al., "Surface hydrophobic residues of multiubiquitin chains essential for proteolytic targeting," PNAS. vol. 93 pp. 861-866 (1996).
Beste, et al., "Small antibody-like proteins with prescribed ligand specificities derived from the lipocalin fold," PNAS. vol. 96 pp. 1898-1903 (1999).
Bird et al., "Single-Chain Antigen-Binding Proteins," Science. vol. 242 pp. 423-426 (1988).
Bolton et al., "Structure and Properties of a Dimeric N-terminal Fragment of Human Ubiquitin," Journal of Molecular Biology. vol. 314 pp. 773-787 (2001).
Brinkmann et al., "A recombinant immunotoxin containing a disulfide-stabilized Fv-fragment," PNAS. vol. 90 pp. 7538-7542 (1993).
Brinkmann et al., "Stabilization of a Recombinant Fv Fragment by Base-Loop Interconnection and VH-VL Permutation," Journal of Molecular Biology. vol. 268 pp. 107-117 (1997).
Buchberger et al., "The UBX Domain: A Widespread Ubiquitin-Like Module," Journal of Molecular Biology. vol. 307, No. 1 pp. 17-24 (2001).
Burch, T.J., and Haas, A.L. "Site-directed mutagenesis of ubiquitin. Differential roles for arginine in the interaction with ubiquitin-activating enzyme," Biochemistry. vol. 33, No. 23, pp. 7300-7308 (1994) [Abstract].
Campion et al., "Biochemical Properties of Site-Directed Mutants of Human Epidermal Growth Factor: Importance of Solvent-Exposed Hydrophobic Residues of the Amino-Terminal Domain in Receptor Binding," Biochemistry. vol. 29, No. 42 pp. 9988-9993 (1990).
Connolly, "Solvent-Accessible Surfaces of Proteins and Nucleic Acids." Science. vol. 221, No. 4612 pp. 709-713 (1983).
Daugherty et al., "Antibody affinity maturation using bacterial surface display," Protein Engineering. vol. 11, No. 9 pp. 825-832 (1998).
de Kruif et al., "Selection and Application of Human Single Chain Fv Antibody Fragments from a Semi-synthetic Phage Antibody Display Library with Designed CDR3 Regions," Journal of Molecular Biology. vol. 248 pp. 97-105 (1995).
Ebersbach et al., "Affilin-Novel Binding Molecules Based on Human (—B-Crystallin, an All (—Sheet Protein," Journal of Molecular Biology. vol. 372 pp. 172-185 (2007).
Ecker et al., "Gene Synthesis, Expression, Structures, and Functional Activities of Site-specific Mutants of Ubiquitin," The Journal of Biological Chemistry, vol. 262, No. 29, pp. 14213-14221 (1987).
European Office Action corresponding to European Patent Application No. 00 944 034.8-2401 dated Oct. 7, 2004. [not in English; P13840].

European Patent Office Examination Report corresponding to European Patent Application No. 06118519.5-2401 dated Apr. 2, 2007. [not in English].
European Search Report corresponding to European Patent Application No. EP 10181802.9-2401 dated Feb. 10, 2011.
European Search Report corresponding to European Patent Application No. 09176574.3-2401 dated Jan. 18, 2010.[need English translation—ask for translation from client; clt. stated not material enough to translate].
Fiedler et al., "AffilinTM Molecules: Novel Ligands for Bioseparation," Trans IChemE, Part C, Food and Bioproducts Processing. vol. 84, No. C1 pp. 3-8 (2006).
Finucane et al., "Core-Directed Protein Design. I. An Experimental Method for Selecting Stable Proteins from Combinatorial Libraries," Biochemistry. vol. 38 pp. 11604-11612 (1999).
Finucane, et al., "Core-Directed Protein Design. II. Rescue of a Multiply Mutated and Destabilized Variant of Ubiquitin." Biochemistry. vol. 38, No. 36 pp. 11613-11623 (1999).
Gebauer, M., and Skerra, A., "Engineered protein scaffolds as next-generation antibody therapeutics," Current Opinion in Chemical Biology. vol. 13 pp. 245-255 (2009).
Grabulovski et al., "A Novel, Non-immunogenic Fyn SH3-derived Binding Protein with Tumor Vascular Targeting Properties," The Journal of Biological Chemistry. vol. 282, No. 5 pp. 3196-3204 (2007).
Guo et al., "Protein tolerance to random amino acid change," PNAS. vol. 101, No. 25 pp. 9205-9210 (2004).
Hanes, J., and Pluckthun, A., "In vitro selection and evolution of functional proteins by using ribosome display," PNAS. vol. 94 pp. 4937-4942 (1997).
Hanes et al., "Picomolar affinity antibodies from a fully synthetic naive library selected and evolved by ribosome display," Nature Biotechnology. vol. 18 pp. 1287-1292 (2000).
Hanes et al., "Ribosome display efficiently selects and evolves high-affinity antibodies in vitro from immune libraries," PNAS. vol. 95. pp. 14130-14135 (1998).
He and Taussig, "Antibody-ribosome-mRNA(ARM) complexes as efficient selection particles for in vitro display and evolution of antibody combining sites," Nucleic Acids Research. vol. 25, No. 24 pp. 5132-5134 (1997).
Hey et al., "Artificial, non-antibody binding proteins for pharmaceutical and industrial applications," Trends in Biotechnology. vol. 23, No. 10 pp. 514-522 (2005).
http://scop.mrc-lmb.cam.ac.uk/scop/data/scop.b.e.ca.html, "Fold: beta-Grasp (ubiquitin-like)," Mar. 15, 2004. [Abstract].
International Preliminary Report on Patentability corresponding to International Patent Application No. PCT/EP2004/005730 dated May 13, 2005. [not in English].
International Search Report corresponding to International Patent Application No. PCT/EP2004/005730 dated Oct. 5, 2004.
International Search Report corresponding to International Patent Application No. PCT/EP2000/006698 dated Feb. 2, 2001.
International Search Report corresponding to International Patent Application No. PCT/EP2005/010932 dated Apr. 11, 2006.
Jackson "Ubiquitin: a small protein folding paradigm." *Org. Biomol. Chem.* vol. 4(10) pp. 1845-1853 (2006).
Jentsch, S., and Pyrowolakis, G., "Ubiquitin and its kin: how close are the family ties?" Trends in Cell Biology. vol. 10 pp. 335-342 (2000).
Khorasanizadeh et al., "Folding and stability of a tryptophan-containing mutant of ubiquitin." *Biochemistry* 32(27): 7054-63 (1993).
Kiel, C., and Serrano, L., "The Ubiquitin Domain Superfold: Structure-based Sequence Alignments and Characterization of Binding Epitopes," J. Mol. Biol. vol. 355 pp. 821-844 (2006).
Knappik et al., "Fully Synthetic Human Combinatorial Antibody Libraries (HuCAL) Based on Modular Consensus Frameworks and CDRs Randomized with Trinucleotides," Journal of Molecular Biology. vol. 296 pp. 57-86 (2000).
Koide et al., "The Fibronectin Type III Domain as a Scaffold for Novel Binding Proteins," Journal of Molecular Biology. vol. 284 pp. 1141-1151 (1998).
Krantz et al., "Discerning the Structure and Energy of Multiple Transition States in Protein Folding using $\Psi$-Analysis," J. Mol. Biol. vol. 337 pp. 463-475 (2004).

(56) References Cited

OTHER PUBLICATIONS

Ku, J., and Schultz, P.G., "Alternate protein frameworks for molecular recognition," PNAS. vol. 92 pp. 6552-6556 (1995).
Larsen et al., "The Ubiquitin Superfamily: Members, Features, and Phylogenies," Journal of Proteome Research. vol. 1 pp. 411-419 (2002).
Laub et al., "Localized solution structure refinement of an F45W variant of ubiquitin using stochastic boundary molecular dynamics and NMR distance restraints," Protein Science. vol. 4 pp. 973-982 (1995).
Lazar, C.N., and Wang, H., "De novo design of the hydrophobic core of ubiquitin," Protein Science. vol. 6 pp. 1167-1178 (1997).
Lipovsek, D., and Pluckthun, A., "In-vitro protein evolution by ribosome display and mRNA display," J. Immunol. Methods. vol. 290 pp. 51-67 (2004).
Mayr et al., "Domain Interactions and Connecting Peptides in Lens Crystallins," Journal of Molecular Biology. vol. 235 pp. 84-88 (1994).
McConnell, S.J., and Hoess, R.H. "Tendamistat as a Scaffold for Conformationally Constrained Phage Peptide Libraries," The Journal of Molecular Biology. vol. 250 pp. 460-470 (1995).
Miura et al., "Characterization of the Binding Interface between Ubiquitin and Class I Human Ubiquitin-conjugating Enzyme 2b by Multidimensional Heteronuclear NMR Spectroscopy in Solution," Journal of Molecular Biology. vol. 290 pp. 213-228 (1999).
Müller et al., "SUMO, ubiquitin's mysterious cousin," Nat. Rev. Mol. Cell Biol. vol. 2 pp. 202-210 (2001).
Müller, H.N., and Skerra, A., "Grafting of a High-Affinity Zn(II)-Binding Site on the β-Barrel of Retional-Binding Protein Results in Enhanced Folding Stability and Enables Simplified Purification," Biochemistry. vol. 33, No. 47 pp. 14126-14135 (1994).
Nord et al., "Binding proteins selected from combinatorial libraries of an (-helical bacterial receptor domain," Nature Biotechnology. vol. 15 pp. 772-777 (1997).
Notice of Allowance corresponding to U.S. Appl. No. 10/030,605 dated Apr. 14, 2009.
Notice of Allowance corresponding to U.S. Appl. No. 11/732,632 dated Aug. 23, 2010.
Notification of Transmittal of Translation of the International Preliminary Report on Patentability (Chapter I of the Patent Cooperation Treaty) corresponding to International Patent Application No. PCT/EP2004/005730 dated Apr. 13, 2006.
Notification of Transmittal of Translarion of the International Preliminary Report on Patentability (Chapter I or Chapter II of the Patent Cooperation Treaty) corresponding to International Application No. PCT/EP2005/010932 dated May 3, 2007.
Notification of Transmittal of the International Search Report and the Written Opinion of the International Searching Authority, or the Declaraton corresponding to International Patent Application No. PCT/EP2010/069674 dated Jun. 17, 2011.
Nygren, P., and Uhien, M., "Scaffolds for engineering novel binding sites in proteins," Current Opinion in Structural Biology. vol. 7 pp. 463-469 (1997).
Official Action corresponding to U.S. Appl. No. 12/072,959 dated Jan. 27, 2009.
Official Action corresponding to U.S. Appl. No. 10/030,605 dated Sep. 21, 2004.
Official Action corresponding to U.S. Appl. No. 10/030,605 dated Feb. 15, 2005.
Official Action corresponding to U.S. Appl. No. 10/030,605 dated Aug. 10, 2005.
Official Action corresponding to U.S. Appl. No. 10/030,605 dated Apr. 12, 2006.
Official Action corresponding to U.S. Appl. No. 10/030,605 dated Feb. 28, 2007.
Official Action corresponding to U.S. Appl. No. 10/030,605 dated Nov. 16, 2007.
Official Action corresponding to U.S. Appl. No. 11/656,646 dated Sep. 1, 2009.
Official Action corresponding to U.S. Appl. No. 11/656,646 dated May 25, 2010.
Official Action corresponding to U.S. Appl. No. 10/030,605 dated Jul. 1, 2008.
Official Action corresponding to U.S. Appl. No. 11/656,646 dated Nov. 13, 2009.
Official Action corresponding to U.S. Appl. No. 11/283,332 dated Jan. 9, 2008.
Official Action corresponding to U.S. Appl. No. 11/283,332 dated May 30, 2008.
Official Action corresponding to U.S. Appl. No. 11/283,332 dated Nov. 28, 2008.
Official Action corresponding to U.S. Appl. No. 11/283,332 dated Sep. 4, 2009.
Official Action corresponding to U.S. Appl. No. 12/072,959 dated Jul. 24, 2008.
Official Action corresponding to U.S. Appl. No. 11/283,332 dated Mar. 3, 2010.
Official Action corresponding to U.S. Appl. No. 12/072,959 dated Jan. 5, 2010.
Official Action corresponding to U.S. Appl. No. 11/732,632 dated Jun. 3, 2009.
Official Action corresponding to U.S. Appl. No. 11/732,632 dated Aug. 21, 2009.
Official Action corresponding to U.S. Appl. No. 11/732,632 dated Mar. 19, 2010.
Official Action corresponding to U.S. Appl. No. 12/514,550 dated Aug. 3, 2011.
Official Action corresponding to U.S. Appl. No. 12/514,550 dated Sep. 15, 2011.
Official Action corresponding to U.S. Appl. No. 12/514,550 dated Mar. 12, 2012.
Ohashi et al., "Efficient protein selection based on ribosome display system with purified components," Biochem. Biophys. Res. Commun. vol. 352 pp. 270-276 (2007).
Pack, P., and Pluckthun, A., "Miniantibodies: Use of Amphipathic Helices to Produce Functional, Flexibly Linked Dimeric Fv Fragments with High Avidity in *Escherichia coli*," Biochemsitry. vol. 31, No. 6 pp. 1579-1584 (1992).
Paschke, M., and Höhne, W., "A twin-arginine translocation (Tat)-mediated phage display system," Gene. vol. 350, No. 1 pp. 79-88 (2005).
Richardson et al., "Looking at proteins: representations, folding, packing, and design," Biophysical Journal. vol. 63 pp. 1186-1209 (1992).
Riddle at al., "Functional rapidly folding proteins from simplified amino acid sequences," Nature Structural Biology. vol. 4, No. 10 pp. 805-809 (1997).
Schaffitzel et al., "In Vitro Selection and Evolution of Protein-Ligand Interactions by Ribosome Display," Protein-Protein Interactions, A Molecular Cloning Manual, E. Golemis, Ed. Cold Spring Harbor Laboratory Press, New York. Chapter 30 pp. 535-567 (2001).
Skerra and Plückthun, "Assembly of a Functional Immunoglobulin Fv Fragment in *Escherichia coli*,"Science vol. 240 pp. 1038-1041 (1988).
Smith et al., "Small Binding Proteins Selected from a Conbinatorial Repertoire of Knottins Displayed on Phage," Journal of Molecular Biology. vol. 277, No. 2 pp. 317-332 (1998).
Stemmer, "Rapid evolution of a protein in vitro by DNA shuffling," Nature. vol. 370 pp. 389-391 (1994).
Wells, "Additivity of Mutational Effects in Proteins," Biochemistry. vol. 29, No. 37 pp. 8509-8517.
Wells and Lowmann, "Rapid evolution of peptide and protein binding properties in vitro," Current Opinion in Biotechnology. vol. 3 pp. 355-362 (1992).
Winter, "Synthetic human antibodies and a strategy for protein engineering," FEBS Letters. vol. 430 pp. 92-94 (1998).
Yeh et al., "Ubiquitin-like proteins: new wines in new bottles," Gene. vol. 248, Nos. 1-2 pp. 1-14 (2000).
You, L., and Arnold, F.H., "Directed evolution of subtilisin E in *Bacillus subtilis* to enhance total activity in aqueous dimethylformamide," Protein Engineering. vol. 9, No. 1 pp. 77-83 (1994).

(56) References Cited

OTHER PUBLICATIONS

Young et al., "Thermal stabilization of a single-chain Fv antibody fragment by introduction of a disulphide bond," FEBS Letters. vol. 377 pp. 135-139 (1995).
Zahnd et al., "Ribosome display: selecting and evolving proteins in vitro that specifically bind to a target," Nature Methods. vol. 4, No. 3 pp. 269-279 (2007).
Zhang et al., "Directed evolution of a fucosidase from a galactosidase by DNA shuffling and screening," PNAS. vol. 94 pp. 4504-4509 (1997).
Bofill et al., "Engineering Stabilising beta-Sheet Interactions into a Conformationally Flexible Region of the Folding Transition State of Ubiquitin," Journal of Molecular Biology, London, GB, vol. 353, No. 2, pp. 373-384 (Oct. 21, 2005) XP005086541 ISSN: 0022-2836.
Ermolenko et al., "Noncharged amino acid residues at the solvent-exposed positions in the middle and at the C terminus of the alpha-helix have the same helical propensity," Protein Science, vol. 12, No. 6, pp. 1169-1176 (Jun. 2003), XP00243791 T ISSN: 0961-8368.
International Preliminary Report on Patentability corresponding to International Application No. PCT/EP2007/062375 dated May 19, 2009.
Loladze et al., "Both helical propensity and side-chain hydrophobicity at a partially exposed site in alpha-helix contribute to the thermodynamic stability of ubiquitin," Proteins, vol. 58, No. 1, pp. 1-6 (Jan. 1, 2005), XP002437914 ISSN: 1097-0134.
Skerra, "Engineered protein scaffolds for molecular recognition," Journal of Molecular Recognition. vol. 13, No. 4 pp. 167-187 (2000).
Yang et al., "Relationship between folding and function in a sequence-specific miniature DNA-binding protein," Biochemistry, vol. 44, No. 20, pp. 7469-7478 (May 24, 2005), XP002437916 ISSN: 0006-2960.
Brandon et al., "Introduction to Protein Structure," Garland Publishing Inc.:New York p. 247 (1991).
Deed of Grant corresponding to Australian Patent No. 2010332932 dated May 2, 2013.
Deed of Grant corresponding to Australian Patent No. 2010332938 dated Apr. 4, 2013.
Hershko, A., and Ciechanover, A., "The Ubiquitin System," Annu. Rev. Biochem. vol. 67 pp. 425-479 (1998).
Intent to Grant corresponding to European Patent Application No. EP 10 787 815.9-1410 dated Aug. 13, 2013.
International Preliminary Report on Patentability corresponding to International Patent Application No. PCT/EP2004/005730 dated May 13, 2005.
Notice of Allowance corresponding to U.S. Appl. No. 11/656,646 dated Aug. 27, 2013.
Official Action corresponding to Chinese Patent Application No. 201080056911.6 dated Jul. 31, 2013.
Official Action corresponding to Korean Patent Application No. 10-2011-7018847 dated Jan. 30, 2013.
Official Action corresponding to U.S. Appl. No. 11/283,332 dated Sep. 3, 2013.
Official Action corresponding to U.S. Appl. No. 12/072,959 dated Aug. 30, 2013.
Search Report corresponding to Chinese Patent Application No. 201080056911.6 dated Jun. 14, 2013.
Official Action corresponding to Japanese Patent Application No. 2012-542583 dated Apr. 22, 2014.

Occurrence of ED-B in Tumors

| Tumor | Stroma/Endothelium | Detection method | Literature |
|---|---|---|---|
| Glioblastoma multiforme (brain) | | IH with L19 | Pini 1998 |
| Breast | | | |
| Lungs | | I-Scinti with L19, mRNA | Oyama 1990 |
| Adenocarcinoma of the lungs | Stroma+Endoth. | IH with C6, mRNA | Balza 2009, Oyama 1990, Pedretti 2009 |
| Colorectal | Stroma | I-Scinti with L19 | Pujuguet 1996 |
| Mesothelioma | Stroma+Endoth. | IH with C6, IH with L19 | Balza 2009, Pedretti 2009 |
| Melanoma | Stroma+Endoth. | IH mit C6 | Balza 2009 |
| Squamous cell carcinoma | Stroma | mRNA | Oyama 1990, Pedretti 2009 |
| Liver | | mRNA | Oyama 1990 |
| Small cell carcinoma | | mRNA | Oyama 1990 |
| Large cell carcinoma | | mRNA | Oyama 1990 |
| Non-small cell lung cancer | | IH with L19 | Pedretti 2009 |
| Pancreas | | | Menrad & Menssen, 2005 |
| Hodgkin lymphoma | | 131I-L19SIP | Sauer et al 2009 |

| Variant | Target ED_B | | | | Target c-FN |
|---|---|---|---|---|---|
| | $K_D$ ELISA | Biacore | | | $K_D$ ELISA |
| | | $K_{on}$ (M$^{-1}$s$^{-1}$) | $K_{off}$ (s$^{-1}$) | $K_D$ (nM) | |
| 9E12 | 9,5 nM | Not determinable | Not determinable | Not determinable | 61,2 nM |
| 22D1 | 594 nM | - | - | - | 711 nM |
| 24H12 | 50,7 nM | - | - | - | 286 nM |
| 41B10 | 310 nM | 293 | 1,82·10$^{-4}$ | 623 nM | 280 nM |

*FIG. 6C*

```
1041-D11_TsX9      1   MQIFVWTWTGKTITLEVEPSDTIENVKAKIQDKEGIPPDQQRLIWAGKQLEDGRTLSDYN
Ub2_TsX9           1   MQIFVKTLTGKTITLEVEPSDTIENVKAKIQDKEGIPPDQQRLIWAGKQLEDGRTLSDYN
Ubi-Dimer wt (Pr   1   MQIFVKTLTGKTITLEVEPSDTIENVKAKIQDKEGIPPDQQRLIFAGKQLEDGRTLSDYN
Ubi-Monomer wt     1   MQIFVKTLTGKTITLEVEPSDTIENVKAKIQDKEGIPPDQQRLIFAGKQLEDGRTLSDYN 1041-D11_TsX9     61   IQRKFPLHLVLRLRGGGIGMRIFVTTQTGKTITLEVEPSDTIENVKAKIQDKEGIPPDQQ
Ub2_TsX9          61   IQKESTLHLVLRLRGGGIGMQIFVKTLTGKTITLEVEPSDTIENVKAKIQDKEGIPPDQQ
Ubi-Dimer wt (Pr  61   IQKESTLHLVLRLRGG---MQIFVKTLTGKTITLEVEPSDTIENVKAKIQDKEGIPPDQQ
Ubi-Monomer wt    61   IQKESTLHLVLRLRGG--------------------------------------------

1041-D11_TsX9    121   RLIWAGKQLEDGRTLSDYNIWSNWELHLVLRLRAA
Ub2_TsX9         121   RLIWAGKQLEDGRTLSDYNIQKESTLHLVLRLRAA
Ubi-Dimer wt (Pr 118   RLIFAGKQLEDGRTLSDYNIQKESTLHLVLRLRGG
Ubi-Monomer wt         -----------------------------------
```

*FIG. 9*

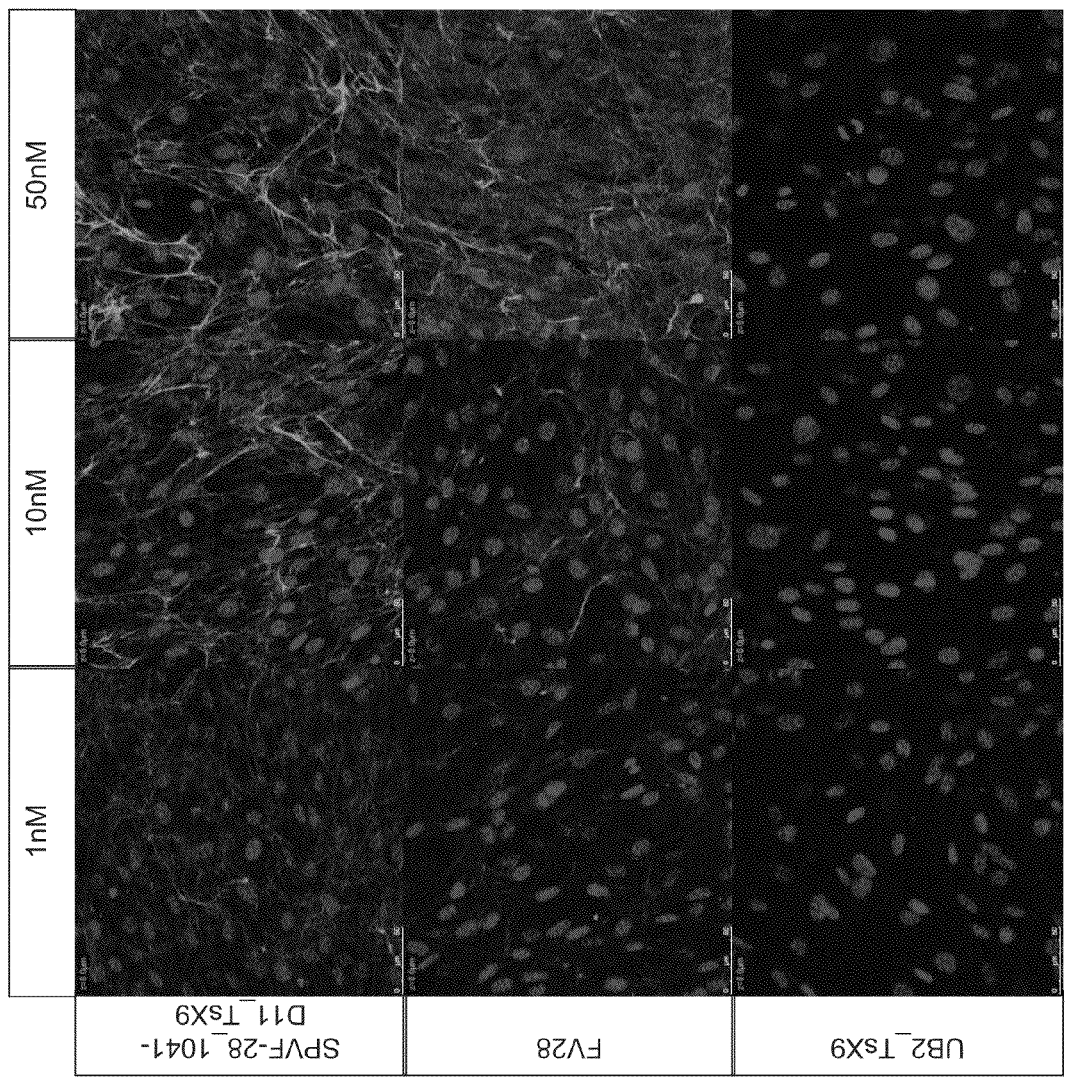

SEQUENCE LISTING

```
<160> NUMBER OF SEQ ID NOS: 80

<210> SEQ ID NO 1
<211> LENGTH: 76
<212> TYPE: PRT
<213> ORGANISM: Artificial Sequence
<220> FEATURE:
<223> OTHER INFORMATION: Ubiquitin Protein

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 91
<212> TYPE: PRT
<213> ORGANISM: Artificial Sequence
```

```
<220> FEATURE:
<223> OTHER INFORMATION: ED-B domain of oncofetal fibronectin

<400> SEQUENCE: 2

Glu Val Pro Gln Leu Thr Asp Leu Ser Phe Val Asp Ile Thr Asp Ser
1               5                   10                  15

Ser Ile Gly Leu Arg Trp Thr Pro Leu Asn Ser Ser Thr Ile Ile Gly
                20                  25                  30

Tyr Arg Ile Thr Val Val Ala Ala Gly Glu Gly Ile Pro Ile Phe Glu
            35                  40                  45

Asp Phe Val Asp Ser Ser Val Gly Tyr Tyr Thr Val Thr Gly Leu Glu
        50                  55                  60

Pro Gly Ile Asp Tyr Asp Ile Ser Val Ile Thr Leu Ile Asn Gly Gly
65                  70                  75                  80

Glu Ser Ala Pro Thr Thr Leu Thr Gln Gln Thr
                85                  90

<210> SEQ ID NO 3
<211> LENGTH: 76
<212> TYPE: PRT
<213> ORGANISM: Artificial Sequence
<220> FEATURE:
<223> OTHER INFORMATION: Ubiquitin variant 1H4

<400> SEQUENCE: 3

Met Trp Ile Lys Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Thr Leu Ser
        50                  55                  60

Arg Ser Leu His Leu Val Leu Arg Leu Arg Gly Gly
65                  70                  75

<210> SEQ ID NO 4
<211> LENGTH: 76
<212> TYPE: PRT
<213> ORGANISM: Artificial Sequence
<220> FEATURE:
<223> OTHER INFORMATION: Ubiquitin variant 4B10

<400> SEQUENCE: 4

Met Leu Ile Leu Val Leu Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Ala Thr Lys
        50                  55                  60

Pro Ile Leu His Leu Val Leu Arg Leu Arg Gly Gly
65                  70                  75

<210> SEQ ID NO 5
<211> LENGTH: 76
<212> TYPE: PRT
<213> ORGANISM: Artificial Sequence
<220> FEATURE:
```

-continued

<223> OTHER INFORMATION: Ubiquitin variant 5E1

<400> SEQUENCE: 5

Met Val Ile Asn Val Phe Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg Ser Thr
    50                  55                  60

Ser Lys Leu His Leu Val Leu Arg Leu Arg Gly Gly
65                  70                  75

<210> SEQ ID NO 6
<211> LENGTH: 164
<212> TYPE: PRT
<213> ORGANISM: Artificial Sequence
<220> FEATURE:
<223> OTHER INFORMATION: Ubiquitin dimer 46H9

<400> SEQUENCE: 6

Met Gly Ile Val Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Pro
    50                  55                  60

Thr Leu Leu His Leu Val Leu Arg Leu Arg Gly Gly Ser Gly Gly Gly
65                  70                  75                  80

Gly Ser Gly Gly Gly Gly Ile Gly Met Gln Ile Phe Val His Thr Met
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Lys Pro Ile Ala Glu Leu His Leu Val Leu Arg
145                 150                 155                 160

Leu Arg Gly Gly

<210> SEQ ID NO 7
<211> LENGTH: 164
<212> TYPE: PRT
<213> ORGANISM: Artificial Sequence
<220> FEATURE:
<223> OTHER INFORMATION: Ubiquitin dimer 9E12

<400> SEQUENCE: 7

Met Arg Ile Pro Val Tyr Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro Pro Phe
        50                  55                  60

Ala Arg Leu His Leu Val Arg Leu Arg Gly Ser Gly Gly
65                  70                  75                  80

Gly Ser Gly Gly Gly Ile Gly Met Gln Ile Phe Val Met Thr Arg
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
            115                 120                 125

Gln Arg Leu Ile Trp Ala Gly Lys Gln Leu Glu Asp Gly Arg Thr Leu
        130                 135                 140

Ser Asp Tyr Asn Ile Met Asn Ala Arg Leu Leu His Leu Val Leu Arg
145                 150                 155                 160

Leu Arg Gly Gly

<210> SEQ ID NO 8
<211> LENGTH: 164
<212> TYPE: PRT
<213> ORGANISM: Artificial Sequence
<220> FEATURE:
<223> OTHER INFORMATION: Ubiquitin dimer 22D1

<400> SEQUENCE: 8

Met Leu Ile Leu Val Arg Thr Leu Thr Asp Lys Thr Ile Thr Leu Glu
1               5                   10                  15

Val Glu Pro Ser Asp Thr Ile Gly Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Ser Val Gly
        50                  55                  60

Ala Met Leu His Leu Val Leu Arg Leu Arg Gly Ser Gly Gly Gly
65                  70                  75                  80

Gly Ser Gly Gly Gly Gly Ile Gly Met Gln Ile Phe Val Leu Thr Trp
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
            115                 120                 125

Gln Arg Leu Ile Trp Ala Gly Lys Gln Leu Glu Asp Gly Arg Thr Leu
        130                 135                 140

Ser Asp Tyr Asn Ile Arg Arg Leu Pro Pro Leu His Leu Val Leu Arg
145                 150                 155                 160

Leu Arg Gly Gly

<210> SEQ ID NO 9
<211> LENGTH: 65
<212> TYPE: DNA
<213> ORGANISM: Artificial Sequence
<220> FEATURE:
<223> OTHER INFORMATION: Primer WUBI(co)RD_xho

<400> SEQUENCE: 9
ggagaccaca acggtttccc tctagaaata attttgttta actttaagaa ggagatatac    60
atatg                                                                65

<210> SEQ ID NO 10
<211> LENGTH: 39
<212> TYPE: DNA
<213> ORGANISM: Artificial Sequence
<220> FEATURE:
<223> OTHER INFORMATION: Primer WUBI(co)RD_xho

<400> SEQUENCE: 10
aaaaaaaaac tcgagaccgc cacgcagacg cagaaccag                                39

<210> SEQ ID NO 11
<211> LENGTH: 834
<212> TYPE: DNA
<213> ORGANISM: Artificial Sequence
<220> FEATURE:
<223> OTHER INFORMATION: Construct H6-SUMO-TNFa

<400> SEQUENCE: 11
atgggcagca gccatcatca tcatcatcac ggcagcggcc tggtgccgcg cggcagcgct        60
agcatgtcgg actcagaagt caatcaagaa gctaagccag aggtcaagcc agaagtcaag       120
cctgagactc acatcaattt aaaggtgtcc gatggatctt cagagatctt cttcaagatc       180
aaaaagacca ctcctttaag aaggctgatg gaagcgttcg ctaaaagaca gggtaaggaa       240
atggactcct taagattctt gtacgacggt attagaattc aagctgatca gacccctgaa       300
gatttggaca tggaggataa cgatattatt gaggctcaca gagaacagat tggtggtgtg       360
cgtagcagca gccgtacccc gagcgataaa ccggtggcgc atgtggtggc gaatccgcag       420
gcggaaggcc agctgcagtg gctgaaccgt cgtgcgaatg cgctgctggc caacggcgtg       480
gaactgcgtg ataatcagct ggttgtgccg agcgaaggcc tgtatctgat ttatagccag       540
gtgctgttta aaggccaggg ctgcccgagc acccatgtgc tgctgaccca taccattagc       600
cgtattgcgg tgagctatca gaccaaagtg aacctgctgt ctgcgattaa agcccgtgc       660 cagcgtgaaa ccccggaagg cgcggaagcg aaaccgtggt atgaaccgat ttatctgggc       720
ggcgtgtttc agctggaaaa aggcgatcgt ctgagcgcgg aaattaaccg tccggattat       780
ctggattttg cggaaagcgg ccaggtgtat tttggcatta ttgcgctgta ataa            834

<210> SEQ ID NO 12
<211> LENGTH: 27
<212> TYPE: DNA
<213> ORGANISM: Artificial Sequence
<220> FEATURE:
<223> OTHER INFORMATION: Primer SUMO-EDB-TNFa-fw

<400> SEQUENCE: 12 tttttggat ccgtgcgtag cagcagc                                             27

<210> SEQ ID NO 13
<211> LENGTH: 28
<212> TYPE: DNA
<213> ORGANISM: Artificial Sequence
<220> FEATURE:
<223> OTHER INFORMATION: Primer SUMO-EDB-TNFa-rev

<400> SEQUENCE: 13
cttgtctctc gaggcggccg cttattac                                           28

<210> SEQ ID NO 14
<211> LENGTH: 33
<212> TYPE: DNA

```
<213> ORGANISM: Artificial Sequence
<220> FEATURE:
<223> OTHER INFORMATION: Primer SUMO-EDB-WUBI-fw

<400> SEQUENCE: 14
gttccaaggt ctcatggtat gcagatcttc gtg                           33

<210> SEQ ID NO 15
<211> LENGTH: 42
<212> TYPE: DNA
<213> ORGANISM: Artificial Sequence
<220> FEATURE:
<223> OTHER INFORMATION: Primer SUMO-EDB-Linker-rev

<400> SEQUENCE: 15
gtggtgggat ccaccgccac caccagaacc gccacgcaga cg                 42

<210> SEQ ID NO 16
<211> LENGTH: 33
<212> TYPE: DNA
<213> ORGANISM: Artificial Sequence
<220> FEATURE:
<223> OTHER INFORMATION: Primer SUMO-EDB-1H4-fw

<400> SEQUENCE: 16
gttccaaggt ctcatggtat gtggatcaag gtg                           33

<210> SEQ ID NO 17
<211> LENGTH: 33
<212> TYPE: DNA
<213> ORGANISM: Artificial Sequence
<220> FEATURE:
<223> OTHER INFORMATION: Primer SUMO-EDB-4B10-fw

<400> SEQUENCE: 17
gttccaaggt ctcatggtat gttgatcctg gtg                           33

<210> SEQ ID NO 18
<211> LENGTH: 33
<212> TYPE: DNA
<213> ORGANISM: Artificial Sequence
<220> FEATURE:
<223> OTHER INFORMATION: Primer SUMO-EDB-5E1-fw

<400> SEQUENCE: 18
gttccaaggt ctcatggtat ggttatcaat gtg                           33

<210> SEQ ID NO 19
<211> LENGTH: 42
<212> TYPE: DNA
<213> ORGANISM: Artificial Sequence
<220> FEATURE:
<223> OTHER INFORMATION: Primer Dimer-t0a-rev

<400> SEQUENCE: 19
gtggtgggat ccaccgccac caccagaacc accacgtaaa cg                 42

<210> SEQ ID NO 20
<211> LENGTH: 33
<212> TYPE: DNA
<213> ORGANISM: Artificial Sequence
<220> FEATURE:
<223> OTHER INFORMATION: Primer SUMO-EDB-WUBI-fw

<400> SEQUENCE: 20
gttccaaggt ctcatggtat gcagatcttc gtg                           33
```

```
<210> SEQ ID NO 21
<211> LENGTH: 33
<212> TYPE: DNA
<213> ORGANISM: Artificial Sequence
<220> FEATURE:
<223> OTHER INFORMATION: Primer 9E12-t0a-fw

<400> SEQUENCE: 21
gttccaaggt ctcatggtat gcgtatccct gtg                                  33

<210> SEQ ID NO 22
<211> LENGTH: 33
<212> TYPE: DNA
<213> ORGANISM: Artificial Sequence
<220> FEATURE:
<223> OTHER INFORMATION: Primer 24H12-t0a-fw

<400> SEQUENCE: 22
gttccaaggt ctcatggtat ggttatcaag gtg                                  33

<210> SEQ ID NO 23
<211> LENGTH: 33
<212> TYPE: DNA
<213> ORGANISM: Artificial Sequence
<220> FEATURE:
<223> OTHER INFORMATION: Primer 15G7-t0a-fw

<400> SEQUENCE: 23
gttccaaggt ctcatggtat ggagatcggt gtg                                  33

<210> SEQ ID NO 24
<211> LENGTH: 33
<212> TYPE: DNA
<213> ORGANISM: Artificial Sequence
<220> FEATURE:
<223> OTHER INFORMATION: Primer 22D1-t0a-fw

<400> SEQUENCE: 24
gttccaaggt ctcatggtat gcttatcttg gtg                                  33

<210> SEQ ID NO 25
<211> LENGTH: 164
<212> TYPE: PRT
<213> ORGANISM: Artificial Sequence
<220> FEATURE:
<223> OTHER INFORMATION: Variant 46-H4

<400> SEQUENCE: 25
```

Met Gly Ile Val Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Pro
    50                  55                  60

Thr Leu Leu His Leu Val Leu Arg Leu Arg Gly Gly Ser Gly Gly Gly
65                  70                  75                  80

Gly Ser Gly Gly Gly Gly Ile Gly Met Gln Ile Phe Val Gly Thr Trp
                85                  90                  95

Thr Gly Lys Thr Ile Thr Leu Glu Val Glu Pro Ser Asp Thr Ile Glu
            100                 105                 110

-continued

```
Asn Val Lys Ala Lys Ile Gln Asp Lys Glu Gly Ile Pro Pro Asp Gln
            115                 120                 125

Gln Arg Leu Ile Trp Ala Gly Lys Gln Leu Glu Asp Gly Arg Thr Leu
        130                 135                 140

Ser Asp Tyr Asn Ile Thr Gln Ala Thr Arg Leu His Leu Val Leu Arg
145                 150                 155                 160

Leu Arg Gly Gly
```

<210> SEQ ID NO 26
<211> LENGTH: 164
<212> TYPE: PRT
<213> ORGANISM: Artificial Sequence
<220> FEATURE:
<223> OTHER INFORMATION: Variant 45-H9

<400> SEQUENCE: 26

```
Met Arg Ile Pro Val Tyr Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro Pro Phe
    50                  55                  60

Ala Arg Leu His Leu Val Leu Arg Leu Arg Gly Gly Ser Gly Gly Gly
65                  70                  75                  80

Gly Ser Gly Gly Gly Ile Gly Met Gln Ile Phe Val Leu Thr Met
            85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
            115                 120                 125

Gln Arg Leu Ile Trp Ala Gly Lys Gln Leu Glu Asp Gly Arg Thr Leu
        130                 135                 140

Ser Asp Tyr Asn Ile Leu Ala Phe Ala Thr Leu His Leu Val Leu Arg
145                 150                 155                 160

Leu Arg Gly Gly
```

<210> SEQ ID NO 27
<211> LENGTH: 164
<212> TYPE: PRT
<213> ORGANISM: Artificial Sequence
<220> FEATURE:
<223> OTHER INFORMATION: Variant 46-A5

<400> SEQUENCE: 27

```
Met Gly Ile Val Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Pro
    50                  55                  60

Thr Leu Leu His Leu Val Leu Arg Leu Arg Gly Gly Ser Gly Gly Gly
65                  70                  75                  80
```

Gly Ser Gly Gly Gly Ile Gly Met Gln Ile Phe Val Leu Thr Met
             85                  90                  95

Thr Gly Lys Thr Ile Thr Leu Glu Val Glu Pro Ser Asp Thr Ile Glu
        100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
        130                 135                 140

Ser Asp Tyr Asn Ile Leu Ala Phe Ala Thr Leu His Leu Val Leu Arg
145                 150                 155                 160

Leu Arg Gly Gly

<210> SEQ ID NO 28
<211> LENGTH: 164
<212> TYPE: PRT
<213> ORGANISM: Artificial Sequence
<220> FEATURE:
<223> OTHER INFORMATION: Variant 50-G11

<400> SEQUENCE: 28

Met Gly Ile Val Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Pro
    50                  55                  60

Thr Leu Leu His Leu Val Leu Arg Leu Arg Gly Gly Ser Gly Gly Gly
65                  70                  75                  80

Gly Ser Gly Gly Gly Gly Ile Gly Met Gln Ile Phe Val Met Thr Arg
                85                  90                  95

Thr Gly Lys Thr Ile Thr Leu Glu Val Glu Pro Ser Asp Thr Ile Glu
        100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
        130                 135                 140

Ser Asp Tyr Asn Ile Met Asn Ala Arg Leu Leu His Leu Val Leu Arg
145                 150                 155                 160

Leu Arg Gly Gly

<210> SEQ ID NO 29
<211> LENGTH: 164
<212> TYPE: PRT
<213> ORGANISM: Artificial Sequence
<220> FEATURE:
<223> OTHER INFORMATION: Variant 52-B3

<400> SEQUENCE: 29

Met Arg Ile Pro Val Tyr Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro Pro Phe

```
Ala Arg Leu His Leu Val Leu Arg Leu Arg Gly Gly Ser Gly Gly
 65                  70                  75                  80

Gly Ser Gly Gly Gly Ile Gly Met Gln Ile Phe Val His Thr Met
                 85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
            115                 120                 125

Gln Arg Leu Ile Trp Ala Gly Lys Gln Leu Glu Asp Gly Arg Thr Leu
            130                 135                 140

Ser Asp Tyr Asn Ile Lys Pro Ile Ala Glu Leu His Leu Val Leu Arg
145                 150                 155                 160

Leu Arg Gly Gly
```

<210> SEQ ID NO 30
<211> LENGTH: 164
<212> TYPE: PRT
<213> ORGANISM: Artificial Sequence
<220> FEATURE:
<223> OTHER INFORMATION: Variant 52-D10

<400> SEQUENCE: 30

```
Met Val Ile Cys Val Arg Thr Leu Thr Gly Lys Thr Ile Thr Leu Glu
 1               5                  10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
             35                  40                  45

Gln Leu Glu Asp Gly Arg Thr Leu Ser Asp Tyr Asn Ile Thr Ala Pro
 50                  55                  60

Gly Asp Leu His Leu Val Leu Arg Leu Arg Gly Gly Ser Gly Gly Gly
 65                  70                  75                  80

Gly Ser Gly Gly Gly Ile Gly Met Gln Ile Phe Val His Thr Met
                 85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
            115                 120                 125

Gln Arg Leu Ile Trp Ala Gly Lys Gln Leu Glu Asp Gly Arg Thr Leu
            130                 135                 140

Ser Asp Tyr Asn Ile Lys Pro Ile Ala Glu Leu His Leu Val Leu Arg
145                 150                 155                 160

Leu Arg Gly Gly
```

<210> SEQ ID NO 31
<211> LENGTH: 8
<212> TYPE: PRT
<213> ORGANISM: Artificial Sequence
<220> FEATURE:
<223> OTHER INFORMATION: H-Tag

<400> SEQUENCE: 31

```
Leu Glu His His His His His His
 1               5
```

<210> SEQ ID NO 32

```
<211> LENGTH: 12
<212> TYPE: PRT
<213> ORGANISM: Artificial Sequence
<220> FEATURE:
<223> OTHER INFORMATION: Glycine/Serine linker

<400> SEQUENCE: 32

Ser Gly Gly Gly Gly Ser Gly Gly Gly Gly Ile Gly
1               5                   10

<210> SEQ ID NO 33
<211> LENGTH: 155
<212> TYPE: PRT
<213> ORGANISM: Artificial Sequence
<220> FEATURE:
<223> OTHER INFORMATION: Ubiquitin dimer SPVF-28_1041-D11_TsX9

<400> SEQUENCE: 33

Met Gln Ile Phe Val Trp Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Arg Lys
    50                  55                  60

Phe Pro Leu His Leu Val Arg Leu Arg Gly Gly Ile Gly Met
65                  70                  75                  80

Arg Ile Phe Val Thr Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Trp Ser Asn Trp
    130                 135                 140

Glu Leu His Leu Val Leu Arg Leu Arg Ala Ala
145                 150                 155

<210> SEQ ID NO 34
<211> LENGTH: 155
<212> TYPE: PRT
<213> ORGANISM: Artificial Sequence
<220> FEATURE:
<223> OTHER INFORMATION: Ubiquitin dimer SPVF-28_1045-D10_TsX9

<400> SEQUENCE: 34

Met Gln Ile Phe Val Trp Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Arg Lys
    50                  55                  60

Phe Pro Leu His Leu Val Leu Arg Leu Arg Gly Gly Ile Gly Met
65                  70                  75                  80

Gln Ile Phe Val Thr Thr Gln Thr Gly Lys Thr Ile Thr Leu Glu Val
                85                  90                  95
```

```
Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Trp Ser Asn Trp
130                 135                 140

Glu Leu His Leu Val Leu Arg Leu Arg Ala Ala
145                 150                 155

<210> SEQ ID NO 35
<211> LENGTH: 319
<212> TYPE: PRT
<213> ORGANISM: Artificial Sequence
<220> FEATURE:
<223> OTHER INFORMATION: fusion Protein SPVF-28_1041-D11_T0aX9

<400> SEQUENCE: 35

Met Gln Ile Phe Val Trp Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Arg Lys
50                  55                  60

Phe Pro Leu His Leu Val Leu Arg Leu Arg Gly Gly Ile Gly Met
65                  70                  75                  80

Arg Ile Phe Val Thr Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Trp Ser Asn Trp
130                 135                 140

Glu Leu His Leu Val Leu Arg Leu Arg Ala Ala Ser Gly Gly Gly Gly
145                 150                 155                 160

Gly Ser Val Arg Ser Ser Arg Thr Pro Ser Asp Lys Pro Val Ala
            165                 170                 175

His Val Val Ala Asn Pro Gln Ala Glu Gly Gln Leu Gln Trp Leu Asn
        180                 185                 190

Arg Arg Ala Asn Ala Leu Leu Ala Asn Gly Val Glu Leu Arg Asp Asn
        195                 200                 205

Gln Leu Val Val Pro Ser Glu Gly Leu Tyr Leu Ile Tyr Ser Gln Val
    210                 215                 220

Leu Phe Lys Gly Gln Gly Cys Pro Ser Thr His Val Leu Leu Thr His
225                 230                 235                 240

Thr Ile Ser Arg Ile Ala Val Ser Tyr Gln Thr Lys Val Asn Leu Leu
                245                 250                 255

Ser Ala Ile Lys Ser Pro Cys Gln Arg Glu Thr Pro Glu Gly Ala Glu
            260                 265                 270

Ala Lys Pro Trp Tyr Glu Pro Ile Tyr Leu Gly Gly Val Phe Gln Leu
        275                 280                 285

Glu Lys Gly Asp Arg Leu Ser Ala Glu Ile Asn Arg Pro Asp Tyr Leu
    290                 295                 300
```

<210> SEQ ID NO 36
<211> LENGTH: 318
<212> TYPE: PRT
<213> ORGANISM: Artificial Sequence
<220> FEATURE:
<223> OTHER INFORMATION: fusion Protein SPVF-28_1041-D11_T0uX9

<400> SEQUENCE: 36

```
Met Gln Ile Phe Val Trp Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Arg Lys
    50                  55                  60

Phe Pro Leu His Leu Val Leu Arg Leu Arg Gly Gly Ile Gly Met
65                  70                  75                  80

Arg Ile Phe Val Thr Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Trp Ser Asn Trp
    130                 135                 140

Glu Leu His Leu Val Leu Arg Leu Arg Ala Ala Ser Gly Gly Gly Gly
145                 150                 155                 160

Gly Ser Leu Arg Ser Ser Gln Asn Ser Ser Asp Lys Pro Val Ala
                165                 170                 175

His Val Val Ala Asn His Gln Val Glu Glu Gln Leu Glu Trp Leu Ser
            180                 185                 190

Gln Arg Ala Asn Ala Leu Leu Ala Asn Gly Met Asp Leu Lys Asp Asn
        195                 200                 205

Gln Leu Val Val Pro Ala Asp Gly Leu Tyr Leu Val Tyr Ser Gln Val
    210                 215                 220

Leu Phe Lys Gly Gln Gly Cys Pro Asp Tyr Val Leu Leu Thr His Thr
225                 230                 235                 240

Val Ser Arg Phe Ala Ile Ser Tyr Gln Glu Lys Val Asn Leu Leu Ser
                245                 250                 255

Ala Val Lys Ser Pro Cys Pro Lys Asp Thr Pro Glu Gly Ala Glu Leu
            260                 265                 270

Lys Pro Trp Tyr Glu Pro Ile Tyr Leu Gly Gly Val Phe Gln Leu Glu
        275                 280                 285

Lys Gly Asp Gln Leu Ser Ala Glu Val Asn Leu Pro Lys Tyr Leu Asp
    290                 295                 300

Phe Ala Glu Ser Gly Gln Val Tyr Phe Gly Val Ile Ala Leu
305                 310                 315
```

<210> SEQ ID NO 37
<211> LENGTH: 155
<212> TYPE: PRT
<213> ORGANISM: Artificial Sequence
<220> FEATURE:

<223> OTHER INFORMATION: Ubiquitin dimer SPVF-28_1048-E10_TsX9

<400> SEQUENCE: 37

Met Gln Ile Phe Val Trp Thr His Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly His Thr Leu Ser Asp Tyr Asn Ile Pro Arg Arg
    50                  55                  60

Ser Trp Leu His Leu Val Leu Arg Leu Arg Gly Gly Ile Gly Met
65                  70                  75                  80

Gln Ile Phe Val Ser Thr Thr Gly Glu Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Ala Asp Pro Arg
    130                 135                 140

Trp Leu His Leu Val Leu Arg Leu Arg Ala Ala
145                 150                 155

<210> SEQ ID NO 38
<211> LENGTH: 155
<212> TYPE: PRT
<213> ORGANISM: Artificial Sequence
<220> FEATURE:
<223> OTHER INFORMATION: Ubiquitin dimer SPVF-28_1041-E6_TsX9

<400> SEQUENCE: 38

Met Gln Ile Phe Val Trp Thr His Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro Arg Arg
    50                  55                  60

Ser Trp Leu His Leu Val Leu Arg Leu Arg Gly Gly Ile Gly Met
65                  70                  75                  80

Gln Ile Phe Val Ser Thr Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Arg
        115                 120                 125

Leu Glu Asp Gly Arg Thr Leu Ser Asp Tyr Asn Ile Ala Asp Pro Arg
    130                 135                 140

Trp Leu His Leu Val Leu Arg Leu Arg Ala Ala
145                 150                 155

<210> SEQ ID NO 39
<211> LENGTH: 155
<212> TYPE: PRT
<213> ORGANISM: Artificial Sequence

```
<220> FEATURE:
<223> OTHER INFORMATION: Ubiquitin dimer SPVF-28_1041-H10_TsX9

<400> SEQUENCE: 39

Met Gln Ile Phe Val Trp Thr Asn Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Glu His Gly
    50                  55                  60

Lys Trp Leu His Leu Val Leu Arg Leu Arg Gly Gly Ile Gly Met
65                  70                  75                  80

Gln Ile Phe Val Asn Thr Thr Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Phe Ile Gly His
    130                 135                 140

Trp Leu His Leu Val Leu Arg Leu Arg Ala Ala
145                 150                 155

<210> SEQ ID NO 40
<211> LENGTH: 158
<212> TYPE: PRT
<213> ORGANISM: Artificial Sequence
<220> FEATURE:
<223> OTHER INFORMATION: Ubiquitin dimer SPVF-28_1056-B6_TsX6

<400> SEQUENCE: 40

Met Gln Ile Phe Val His Thr His Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Arg Asp
    50                  55                  60

Lys Arg Leu His Leu Val Leu Arg Leu Arg Ala Ala Ser Gly Gly Gly
65                  70                  75                  80

Gly Ile Gly Met Gln Ile Phe Val Asn Thr Asn Thr Gly Glu Thr Ile
                85                  90                  95

Thr Leu Glu Val Glu Pro Ser Asp Thr Ile Glu Asn Val Lys Ala Lys
            100                 105                 110

Ile Gln Asp Lys Glu Gly Ile Pro Pro Asp Gln Gln Arg Leu Ile Trp
        115                 120                 125

Ala Gly Lys Arg Leu Glu Asp Gly Arg Thr Leu Ser Asp Tyr Asn Ile
    130                 135                 140

Asp Trp Arg Trp Leu His Leu Val Leu Arg Leu Arg Ala Ala
145                 150                 155

<210> SEQ ID NO 41
<211> LENGTH: 154
<212> TYPE: PRT
```

<213> ORGANISM: Artificial Sequence
<220> FEATURE:
<223> OTHER INFORMATION: Ubiquitin dimer SPVF-28_1051-B7_TsX9

<400> SEQUENCE: 41

```
Met Gln Ile Phe Val His Thr Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Thr Leu Thr
    50                  55                  60

Pro Thr Leu His Leu Val Leu Arg Leu Arg Gly Gly Ile Gly Met
65                  70                  75                  80

Gln Ile Phe Val Leu Thr Leu Thr Gly Lys Thr Ile Thr Leu Glu Val
                85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Asp Trp Arg Trp
        130                 135                 140

Leu His Leu Val Leu Arg Leu Arg Ala Ala
145                 150
```

<210> SEQ ID NO 42
<211> LENGTH: 155
<212> TYPE: PRT
<213> ORGANISM: Artificial Sequence
<220> FEATURE:
<223> OTHER INFORMATION: Ubiquitin dimer SPVF-28_1035-E6_TsX9

<400> SEQUENCE: 42

```
Met Gln Ile Phe Val His Thr Phe Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile His Glu Arg
    50                  55                  60

Glu Ile Leu His Leu Val Leu Arg Leu Arg Gly Gly Ile Gly Met
65                  70                  75                  80

Gln Ile Phe Val Ser Thr Pro Thr Gly Lys Thr Ile Thr Leu Glu Val
                85                  90                  95

Glu Pro Ser Asp Thr Ile Glu Asn Val Lys Ala Lys Ile Gln Asp Lys
                100                 105                 110

Glu Gly Ile Pro Pro Asp Gln Gln Arg Leu Ile Trp Ala Gly Lys Gln
            115                 120                 125

Leu Glu Asp Gly Arg Thr Leu Ser Asp Tyr Asn Ile Gly Val Glu Met
        130                 135                 140

Leu Leu His Leu Val Leu Arg Leu Arg Ala Ala
145                 150                 155
```

<210> SEQ ID NO 43
<211> LENGTH: 154

```
<212> TYPE: PRT
<213> ORGANISM: Artificial Sequence
<220> FEATURE:
<223> OTHER INFORMATION: Ubiquitin dimer SPVF-28_1049-D4_TsX9

<400> SEQUENCE: 43
```

Met Gln Ile Phe Val His Thr Asp Thr Gly Lys Thr Ile Thr Leu Glu
1               5                   10                  15

Val Glu Pro Ser Asp Thr Ile Glu Asn Val Lys Ala Glu Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile His Asn Trp
50                  55                  60

Arg Asn Leu His Leu Val Leu Arg Leu Arg Gly Gly Ile Gly Met
65                  70                  75                  80

Gln Ile Phe Val Ile Thr Ile Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Lys Asp Gly Arg Thr Leu Ser Asp Tyr Asn Ile Asp Trp Arg Trp
130                 135                 140

Leu His Leu Val Leu Arg Leu Arg Ala Ala
145                 150

```
<210> SEQ ID NO 44
<211> LENGTH: 164
<212> TYPE: PRT
<213> ORGANISM: Artificial Sequence
<220> FEATURE:
<223> OTHER INFORMATION: Ubiquitin dimer SPWF-28_1071-C8_TsX2

<400> SEQUENCE: 44
```

Met Trp Ile Arg Val Pro Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile His Met Pro
50                  55                  60

Asp Ile Leu His Leu Val Leu Arg Leu Arg Gly Gly Ser Gly Gly Gly
65                  70                  75                  80

Gly Ser Gly Gly Gly Ile Gly Met Gln Ile Phe Val Trp Thr Met
            85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
            115                 120                 125

Gln Arg Leu Ile Trp Ala Gly Lys Gln Leu Glu Asp Gly Arg Thr Leu
        130                 135                 140

Ser Asp Tyr Asn Ile His Leu His Met Arg Leu His Leu Val Leu Arg
145                 150                 155                 160

Leu Arg Gly Gly

```
<210> SEQ ID NO 45
<211> LENGTH: 164
<212> TYPE: PRT
<213> ORGANISM: Artificial Sequence
<220> FEATURE:
<223> OTHER INFORMATION: Ubiquitin dimer SPWF-28_1071-C12_TsX2

<400> SEQUENCE: 45

Met Thr Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Phe Lys
    50                  55                  60

Leu Ser Leu His Leu Val Leu Arg Leu Arg Gly Gly Ser Gly Gly Gly
65                  70                  75                  80

Gly Ser Gly Gly Gly Gly Ile Gly Met Gln Ile Phe Val Ser Thr Phe
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile His Tyr Leu Pro Lys Leu His Leu Val Leu Arg
145                 150                 155                 160

Leu Arg Gly Gly

<210> SEQ ID NO 46
<211> LENGTH: 172
<212> TYPE: PRT
<213> ORGANISM: Artificial Sequence
<220> FEATURE:
<223> OTHER INFORMATION: Ubiquitin dimer SPWF-28_1071-H7_TsX2

<400> SEQUENCE: 46

Met Trp Ile Arg Val Pro Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Arg Arg Val
    50                  55                  60

Asn Tyr Leu His Leu Val Leu Arg Leu Arg Gly Gly Ser Gly Gly Gly
65                  70                  75                  80

Gly Ser Gly Gly Gly Gly Ile Gly Met Gln Ile Phe Val Trp Thr Ser
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140
```

```
Ser Asp Tyr Asn Ile Tyr Thr Tyr Met Arg Leu His Leu Val Leu Arg
145                 150                 155                 160

Leu Arg Gly Gly Leu Glu His His His His His His
                165                 170
```

<210> SEQ ID NO 47
<211> LENGTH: 164
<212> TYPE: PRT
<213> ORGANISM: Artificial Sequence
<220> FEATURE:
<223> OTHER INFORMATION: Ubiquitin dimer with linker SGGGGSGGGGIG
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (150)..(154)
<223> OTHER INFORMATION: Xaa can be any naturally occurring amino acid

<400> SEQUENCE: 47

```
Met Thr Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Asn Phe Lys
50                  55                  60

Leu Ser Leu His Leu Val Leu Arg Leu Arg Gly Gly Ser Gly Gly Gly
65                  70                  75                  80

Gly Ser Gly Gly Gly Gly Ile Gly Met Gln Ile Phe Val Xaa Thr Xaa
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Xaa Xaa Xaa Xaa Xaa Leu His Leu Val Leu Arg
145                 150                 155                 160

Leu Arg Gly Gly
```

<210> SEQ ID NO 48
<211> LENGTH: 5
<212> TYPE: PRT
<213> ORGANISM: Artificial Sequence
<220> FEATURE:
<223> OTHER INFORMATION: Glycine/Serine linker

<400> SEQUENCE: 48

```
Ser Gly Gly Gly Gly
1               5
```

<210> SEQ ID NO 49
<211> LENGTH: 7
<212> TYPE: PRT
<213> ORGANISM: Artificial Sequence
<220> FEATURE:

```
<223> OTHER INFORMATION: Glycine/Serine linker

<400> SEQUENCE: 49

Ser Gly Gly Gly Gly Ile Gly
1               5

<210> SEQ ID NO 50
<211> LENGTH: 10
<212> TYPE: PRT
<213> ORGANISM: Artificial Sequence
<220> FEATURE:
<223> OTHER INFORMATION: Glycine/Serine linker

<400> SEQUENCE: 50

Ser Gly Gly Gly Gly Ser Gly Gly Gly Gly
1               5                   10

<210> SEQ ID NO 51
<211> LENGTH: 164
<212> TYPE: PRT
<213> ORGANISM: Artificial Sequence
<220> FEATURE:
<223> OTHER INFORMATION: Embodiment of ubiquitin dimer with linker
      SGGGGSGGGGIG
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (150)..(154)
<223> OTHER INFORMATION: Xaa can be any naturally occurring amino acid

<400> SEQUENCE: 51

Met Thr Ile Trp Val His Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asn Phe Lys
    50                  55                  60

Leu Ser Leu His Leu Val Leu Arg Leu Arg Gly Gly Ser Gly Gly Gly
65                  70                  75                  80

Gly Ser Gly Gly Gly Ile Gly Met Gln Ile Phe Val Xaa Thr Xaa
                85                  90                  95

Thr Gly Lys Thr Ile Thr Leu Glu Val Glu Pro Ser Asp Thr Ile Glu
            100                 105                 110

Asn Val Lys Ala Lys Ile Gln Asp Lys Glu Gly Ile Pro Pro Asp Gln
        115                 120                 125

Gln Arg Leu Ile Trp Ala Gly Lys Gln Leu Glu Asp Gly Arg Thr Leu
    130                 135                 140

Ser Asp Tyr Asn Ile Xaa Xaa Xaa Xaa Xaa Leu His Leu Val Leu Arg
145                 150                 155                 160

Leu Arg Gly Gly

<210> SEQ ID NO 52
<211> LENGTH: 5
<212> TYPE: PRT
```

```
<213> ORGANISM: Artificial Sequence
<220> FEATURE:
<223> OTHER INFORMATION: Artifical consensus region

<400> SEQUENCE: 52

Asn Phe Lys Leu Ser
1               5

<210> SEQ ID NO 53
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 53

Gly Trp Leu Ala Pro
1               5

<210> SEQ ID NO 54
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 54

Asp Trp Leu Pro Ala
1               5

<210> SEQ ID NO 55
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 55

Asp Ser His Asp Val
1               5

<210> SEQ ID NO 56
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 56

His Tyr Leu Pro Lys
1               5

<210> SEQ ID NO 57
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 57

Trp His His Asp Phe
1               5

<210> SEQ ID NO 58
<211> LENGTH: 5
<212> TYPE: PRT
<213> ORGANISM: Artificial Sequence
```

```
<220> FEATURE:
<223> OTHER INFORMATION: Amino acid 141-145 variant

<400> SEQUENCE: 58

Gly Trp Gln Ser Pro
1               5

<210> SEQ ID NO 59
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 59

Gly Trp Gln Ala Pro
1               5

<210> SEQ ID NO 60
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 60

Trp Ser Gly Glu Phe
1               5

<210> SEQ ID NO 61
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 61

Gly Phe Gln Ser Pro
1               5

<210> SEQ ID NO 62
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 62

Gly Trp Gln Ser Pro
1               5

<210> SEQ ID NO 63
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 63

Ala Thr Leu Pro Asn
1               5

<210> SEQ ID NO 64
<211> LENGTH: 5
<212> TYPE: PRT
<213> ORGANISM: Artificial Sequence
<220> FEATURE:
```

-continued

```
<223> OTHER INFORMATION: Amino acid 141-145 variant

<400> SEQUENCE: 64

Trp His His Asp Met
1               5

<210> SEQ ID NO 65
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 65

Trp Pro Gly Asp Met
1               5

<210> SEQ ID NO 66
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 66

Gly Arg Leu Pro Lys
1               5

<210> SEQ ID NO 67
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 67

Gly Tyr Met Ala Pro
1               5

<210> SEQ ID NO 68
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 68

Gly Tyr Gln Ala Pro
1               5

<210> SEQ ID NO 69
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 69

Gly Tyr Gln Val Pro
1               5

<210> SEQ ID NO 70
<211> LENGTH: 5
<212> TYPE: PRT
<213> ORGANISM: Artificial Sequence
<220> FEATURE:
<223> OTHER INFORMATION: Amino acid 141-145 variant
```

```
<400> SEQUENCE: 70

Trp Thr Arg Asp Trp
1               5

<210> SEQ ID NO 71
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 71

Asp Arg Leu Pro Val
1               5

<210> SEQ ID NO 72
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 72

Glu Arg Leu Pro Gln
1               5

<210> SEQ ID NO 73
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 73

Trp Gln His Asp Phe
1               5

<210> SEQ ID NO 74
<211> LENGTH: 5
<212> TYPE: PRT
<213> ORGANISM: Artificial Sequence
<220> FEATURE:
<223> OTHER INFORMATION: Amino acid 141-145 variant

<400> SEQUENCE: 74

His His Leu Pro Thr
1               5

<210> SEQ ID NO 75
<211> LENGTH: 164
<212> TYPE: PRT
<213> ORGANISM: Artificial Sequence
<220> FEATURE:
<223> OTHER INFORMATION: Artifical ubiquitin variant WubiHub-Protein

<400> SEQUENCE: 75

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60
```

```
Ser Thr Leu His Leu Val Leu Arg Leu Arg Gly Ser Gly Gly Gly
 65                  70                  75                  80

Gly Ser Gly Gly Gly Gly Ile Gly Met Gln Ile Phe Val Lys Thr Leu
                 85                  90                  95

Thr Gly Lys Thr Ile Thr Leu Glu Val Glu Pro Ser Asp Thr Ile Glu
                100                 105                 110

Asn Val Lys Ala Lys Ile Gln Asp Lys Glu Gly Ile Pro Pro Asp Gln
            115                 120                 125

Gln Arg Leu Ile Trp Ala Gly Lys Gln Leu Glu Asp Gly Arg Thr Leu
        130                 135                 140

Ser Asp Tyr Asn Ile Gln Lys Glu Ser Thr Leu Met Leu Val Leu Arg
145                 150                 155                 160

Leu Arg Gly Gly

<210> SEQ ID NO 76
<211> LENGTH: 164
<212> TYPE: PRT
<213> ORGANISM: Artificial Sequence
<220> FEATURE:
<223> OTHER INFORMATION: Artificial ubiquitin hetero-dimeric variant
      pPR-IBAi-46H9_Ts

<400> SEQUENCE: 76

Met Gly Ile Val Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Pro His Pro
    50                  55                  60

Thr Leu Leu His Leu Val Leu Arg Leu Arg Gly Gly Ser Gly Gly Gly
 65                 70                  75                  80

Gly Ser Gly Gly Gly Gly Ile Gly Met Gln Ile Phe Val His Thr Met
                 85                  90                  95

Thr Gly Lys Thr Ile Thr Leu Glu Val Glu Pro Ser Asp Thr Ile Glu
                100                 105                 110

Asn Val Lys Ala Lys Ile Gln Asp Lys Glu Gly Ile Pro Pro Asp Gln
            115                 120                 125

Gln Arg Leu Ile Trp Ala Gly Lys Gln Leu Glu Asp Gly Arg Thr Leu
        130                 135                 140

Ser Asp Tyr Asn Ile Lys Pro Ile Ala Glu Leu Met Leu Val Leu Arg
145                 150                 155                 160

Leu Arg Gly Gly

<210> SEQ ID NO 77
<211> LENGTH: 155
<212> TYPE: PRT
<213> ORGANISM: Artificial Sequence
<220> FEATURE:
<223> OTHER INFORMATION: Artificial ubiquitin hetero-dimeric variant
      1041-D11

<400> SEQUENCE: 77

Met Gln Ile Phe Val Trp Thr Trp Thr Gly Lys Thr Ile Thr Leu Glu
1               5                   10                  15

Val Glu Pro Ser Asp Thr Ile Glu Asn Val Lys Ala Lys Ile Gln Asp
```

```
                    20                  25                  30
Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Gln Arg Lys
        50                  55                  60

Phe Pro Leu His Leu Val Arg Leu Arg Gly Gly Ile Gly Met
65                  70                  75                  80

Arg Ile Phe Val Thr Thr Gln Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Trp Ser Asn Trp
    130                 135                 140

Glu Leu His Leu Val Leu Arg Leu Arg Ala Ala
145                 150                 155

<210> SEQ ID NO 78
<211> LENGTH: 155
<212> TYPE: PRT
<213> ORGANISM: Artificial Sequence
<220> FEATURE:
<223> OTHER INFORMATION: Artificial ubiquitin hetero-dimeric variant
      UB2_TxX9

<400> SEQUENCE: 78

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ile Gly Met
65                  70                  75                  80

Gln Ile Phe Val Lys Thr Leu Thr Gly Lys Thr Ile Thr Leu Glu Val
                85                  90                  95

Glu Pro Ser Asp Thr Ile Glu Asn Val Lys Ala Lys Ile Gln Asp Lys
            100                 105                 110

Glu Gly Ile Pro Pro Asp Gln Gln Arg Leu Ile Trp Ala Gly Lys Gln
        115                 120                 125

Leu Glu Asp Gly Arg Thr Leu Ser Asp Tyr Asn Ile Gln Lys Glu Ser
    130                 135                 140

Thr Leu His Leu Val Leu Arg Leu Arg Ala Ala
145                 150                 155

<210> SEQ ID NO 79
<211> LENGTH: 152
<212> TYPE: PRT
<213> ORGANISM: Artificial Sequence
<220> FEATURE:
<223> OTHER INFORMATION: Artifical human ubiquitin dimer

<400> SEQUENCE: 79

Met Gln Ile Phe Val Lys Thr Leu Thr Gly Lys Thr Ile Thr Leu Glu
1               5                   10                  15
```

-continued

```
Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                      70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Phe Ala Gly Lys Gln Leu Glu Asp
            115                 120                 125

Gly Arg Thr Leu Ser Asp Tyr Asn Ile Gln Lys Glu Ser Thr Leu His
            130                 135                 140

Leu Val Leu Arg Leu Arg Gly Gly
145                 150

<210> SEQ ID NO 80
<211> LENGTH: 76
<212> TYPE: PRT
<213> ORGANISM: Homo sapiens

<400> SEQUENCE: 80

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                      70                  75
```

US 8,921,304 B2

MODIFIED UBIQUITIN PROTEINS HAVING A SPECIFIC BINDING ACTIVITY FOR THE EXTRADOMAIN B OF FIBRONECTIN

FIELD OF THE INVENTION

The present invention refers to novel hetero-multimeric proteins capable of binding the extradomain B of fibronectin (ED-B). Furthermore, the invention refers to fusion proteins comprising said hetero-multimeric binding protein fused to a pharmaceutically and/or diagnostically active component. The invention is further directed to a method for the generation of such a hetero-multimeric binding protein or fusion protein and to pharmaceutical and/or diagnostic compositions containing said hetero-multimeric binding proteins. In addition, the invention refers to libraries containing DNA encoding for said proteins.

In further embodiments, the invention is directed to polynucleotides coding for said hetero-multimeric binding protein or fusion protein, vectors comprising said polynucleotide and host cells comprising said protein, fusion protein, vector and/or polynucleotide. In a preferred embodiment, said hetero-multimeric binding protein or fusion protein is included in a medicament or a diagnostic agent. Additionally, methods for producing said recombinant protein or fusion protein as well as use of said proteins in medical treatment methods are described.

BACKGROUND OF THE INVENTION

There is a growing demand for binding molecules consisting of amino acids which are not immunoglobulins. While until now antibodies represent the best-established class of binding molecules there is still a need for new binding molecules in order to target ligands with high affinity and specificity since immunoglobulin molecules suffer from major drawbacks. Although they can be produced quite easily and may be directed to almost any target, they have a quite complex molecular structure. There is an ongoing need to substitute antibodies by smaller molecules which can be handled in an easy way. These alternative binding agents can be beneficially used for instance in the medical fields of diagnosis, prophylaxis and treatment of diseases.

Proteins having relatively defined 3-dimensional structures, commonly referred to as protein scaffolds, may be used as starting material for the design of said alternative binding agents. These scaffolds typically contain one or more regions which are amenable to specific or random sequence variation, and such sequence randomisation is often carried out to produce a library of proteins from which the specific binding molecules may be selected. Molecules with a smaller size than antibodies and a comparable or even better affinity towards a target antigen are expected to be superior to antibodies in terms of pharmacokinetic properties and immunogenicity.

A number of previous approaches do use protein scaffolds as starting material of binding proteins. For example, in WO 99/16873 modified proteins of the lipocalin family (so-called Anticalins) exhibiting binding activity for certain ligands were developed. The structure of peptides of the lipocalin family is modified by amino acid replacements in their natural ligand binding pocket using genetic engineering methods. Like immunoglobulins, the Anticalins can be used to identify or bind molecular structures. In a manner analogously to antibodies, flexible loop structures are modified; these modifications enable the recognition of ligands different from the natural ones.

WO 01/04144 describes the artificial generation of a binding domain on the protein surface in beta sheet structural proteins per se lacking a binding site. By means of this de novo generated artificial binding domain e.g. variations in γ-crystallin—an eye lens structural protein—can be obtained which interact with ligands with high affinity and specificity. In contrast to the modification of binding sites which are already present and formed from flexible loop structures as mentioned above for Anticalins, these binding domains are generated de novo on the surface of beta sheets. However, WO 01/04144 only describes the alteration of relatively large proteins for the generation of novel binding properties. Due to their size the proteins according to WO 01/04144 can be modified on the genetic engineering level only by methods which require some effort. Furthermore, in the proteins disclosed so far only a relatively small proportion by percentage of the total amino acids was modified in order to maintain the overall structure of the protein. Therefore, only a relatively small region of the protein surface is available which can be utilized for the generation of binding properties that did not exist previously. Moreover, WO 01/04144 discloses only the generation of a binding property to γ-crystallin.

WO 04/106368 describes the generation of artificial binding proteins on the basis of ubiquitin proteins. Ubiquitin is a small, monomeric, and cytosolic protein which is highly conserved in sequence and is present in all known eukaryotic cells from protozoans to vertebrates. In the organism, it plays a crucial role in the regulation of the controlled degradation of cellular proteins. For this purpose, the proteins destined for degradation are covalently linked to ubiquitin or polyubiquitin chains during their passage through a cascade of enzymes and are selectively degraded because of this label. According to recent results, ubiquitin or the labelling of proteins by ubiquitin, respectively, plays an important role also in other cellular processes such as the import of several proteins or the gene regulation thereof.

Besides the clarification of its physiological function, ubiquitin is a research object primarily because of its structural and protein-chemical properties. The polypeptide chain of ubiquitin consists of 76 amino acids folded in an extraordinarily compact α/β structure (Vijay-Kumar, 1987): almost 87% of the polypeptide chain is involved in the formation of the secondary structural elements by means of hydrogen bonds. Secondary structures are three and a half alpha-helical turns as well as an antiparallel β sheet consisting of four strands. The characteristic arrangement of these elements—an antiparallel β sheet exposed of the protein surface onto the back side of which an alpha helix is packed which lies vertically on top of it—is generally considered as so-called ubiquitin-like folding motif. A further structural feature is a marked hydrophobic region in the protein interior between the alpha helix and the β sheet.

Because of its small size, artificial preparation of ubiquitin can be carried out both by chemical synthesis and by means of biotechnological methods. Due to the favourable folding properties, ubiquitin can be produced by genetic engineering using microorganisms such as *Escherichia coli* in relatively large amounts either in the cytosol or in the periplasmic space. Because of the oxidizing conditions predominating in the periplasm the latter strategy generally is reserved for the production of secretory proteins. Due to the simple and efficient bacterial preparation ubiquitin can be used as a fusion partner for other foreign proteins to be prepared for which the production is problematic. By means of fusion to ubiquitin an improved solubility and thereby an improved production yield can be achieved.

Compared to antibodies or other alternative scaffolds, artificial binding proteins on the basis of ubiquitin proteins (also referred to as AFFILIN®) have many advantages: small size, high stability, high affinity, high specificity, cost effective microbial manufacturing, and adjustment of serum half life. However, there is still a need to further develop those proteins in terms of new therapeutic approaches with high affinities to specific targets. While WO 05/05730 generally describes the use of ubiquitin scaffolds in order to obtain artificial binding proteins, no solution is provided on how to modify an ubiquitin protein in order to obtain a specific and high affinity binding to the ED-B of fibronectin.

WO 2008/022759 describes recombinant binding proteins wherein the Src homology 3 domain (SH3) of the FYN kinase is used for obtaining new binding proteins. It was found that the target specificity can be designed by mutating the RT loop and/or the Src loop in order to develop protein therapeutics and/or diagnostics. Like in lipocalins used as scaffold, the amino acid residues to be mutagenized lie within the variable and flexible loop regions mimicking the principle underlying the antibody/antigen binding function. This overall flexibility of the interaction site by which antibodies bind the epitope is a mainly enthalpically driven process; this process, however, leads to an unfavorable entropic contribution by loss of mobility upon association of the flexible complementarity determining region. Contrary thereto, using ubiquitin as a scaffold, the present inventors did not change amino acid residues primarily within the flexible loop regions but within the rigid and inflexible β strands of a β sheet region or closely adjacent to the beta strands. The advantage of selecting amino acid residues within the inflexible and rigid β strands or closely adjacent to the beta strands of ubiquitin as binding regions for ED-B is inter alia the following: The binding partners are thought to already present a complementary geometry appropriate for tight binding. Consequently, these interactions involve complementarity in shape, charge and hydrophilic/hydrophobic elements of the more rigid structures of the binding partners. These rigid body interactions optimize the interface and accommodate biological function.

Fibronectins (FN) are an important class of high molecular weight extracellular matrix glycoproteins abundantly expressed in healthy tissues and body fluids. Their main role consists in facilitating the adhesion of cells to a number of different extracellular matrices. The presence of fibronectins on the surface of non-transformed cells in culture as well as their absence in the case of transformed cells resulted in the identification of fibronectins as important adhesion proteins. They interact with numerous various other molecules, e.g. collagen, heparan sulphate-proteoglycans and fibrin and thus regulate the cell shape and the creation of the cytoskeleton. In addition, they are responsible for cell migration and cell differentiation during embryogenesis. They also play an important role in wound healing, in which they facilitate the migration of macrophages and other immune cells and in the formation of blood clots by enabling the adhesion of blood platelets to damaged regions of the blood vessels.

The extra-domain B (ED-B) of fibronectin is a small domain which is inserted by alternative splicing of the primary RNA transcript into the fibronectin molecule. The molecule is either present or omitted in fibronectin molecules of the extracellular matrix and represents a one of the most selective markers associated with angiogenesis and tissue remodelling, as it is abundantly expressed around new blood vessels, but undetectable in virtually all normal adult tissues (except for uterus and ovaries). ED-B is known to be involved primarily in cancer. High levels of ED-B expression were detected in primary lesions as well as metastatic sites of many human solid cancer entities, including breast, non-small cell lung, colorectal, pancreatic, human skin, hepatocellular, intracraneal meningeoma, glioblastoma (Menrad u. Menssen, 2005). Furthermore, ED-B can be bound to diagnostic agents and be favorably used as diagnostic tool. One example is its use in molecular imaging of e.g. atherosclerotic plaques and detection of cancer, e.g. by immunoscintigraphy of cancer patients. Plenty of further diagnostic uses are conceivable.

The amino acid sequence of 91 amino acids of human extra-domain B (ED-B) of fibronectin is shown in SEQ ID NO: 2. For expression of the protein, a start methionin has to be added. ED-B is abundant in mammals, e.g. in rodents, cattle, primates, carnivore, human etc. Examples of animals in which there is a 100% sequence identity to human ED-B are *Rattus norvegicus, Bos taurus, Mus musculus, Equus caballus, Macaca mulatta, Canis lupus familiaris*, and *Pan troglodytes*.

ED-B specifically accumulates in neo-vascular structures and represents a target for molecular intervention in cancer. A number of antibodies or antibody fragments to the ED-B domain of fibronectin are known in the art as potential therapeutics for cancer and other indications (see, for example, WO 97/45544, WO 07/054,120, WO 99/58570, WO 01/62800). Human single chain Fv antibody fragment ScFvL19 (also referred to as L19) is specific to the ED-B domain of fibronectin and has been verified to selectively target tumor neovasculature, both in experimental tumor models and in patients with cancer. Furthermore, conjugates comprising an anti-ED-B antibody or an anti-ED-B antibody fragment with cytokines such as IL-12, IL-2, IL-10, IL-15, IL-24, or GM-CSF have been described for targeting drugs for the manufacture of a medicament for inhibiting particularly cancer, angiogenesis, or neoplastic growth (see, for example, WO06/119897, WO07/128,563, WO01/62298). The selective targeting of neovasculature of solid tumors with anti-ED-B antibodies or anti-ED-B antibody fragments such as L19 conjugated to an appropriate effector function such as a cytotoxic or an immunostimulating agent has proven to be successful in animal experiments. For the therapy of pancreatic cancer, fusion proteins comprising an Interleukin-2 part (IL-2) and an anti-ED-B antibody part were combined with the small molecule Gemcitabine (2'-deoxy-2',2'-difluorocytidine) (see, for example, WO 07/115,837).

The above-discussed prior art documents describe the use of various protein scaffolds including antibodies to generate new ED-B binding proteins. Targeting ED-B with currently available compounds has certain disadvantages. Smaller molecules (such as hetero-multimeric ubiquitin-based ED-B binding proteins of this invention) with a comparable or even higher affinity towards the ED-B antigen are expected to have significant advantages to antibodies or other binding proteins.

Since cancer represents one of the leading causes for death worldwide, there is a growing need for improved agents for treating cancer. Current chemotherapeutic agents and radiation treatment suffer from poor selectivity and most chemotherapeutic agents do not accumulate at the tumor site and thus fail to achieve adequate levels within the tumor. There is a strong medical need to effectively treat cancer.

It is thus an object of the present invention to provide hetero-multimeric binding proteins based on ubiquitin being able to bind specifically with very high affinity to the extracellular domain of fibronectin (ED-B). It is a further object of the present invention to identify and provide novel binding proteins with very high binding specificity to ED-B for example for use in the treatment of cancer. Furthermore, a method shall be provided in order to produce said hetero-multimeric binding molecules.

The above-described objects are solved by the subject-matter of the enclosed independent claims. Preferred embodiments of the invention are included in the dependent claims as well as in the following description, examples and figures.

DESCRIPTION OF THE INVENTION

More specifically, the inventors provide a protein capable of binding the ED-B of human fibronectin, comprising a modified hetero-dimeric ubiquitin protein wherein two monomeric ubiquitins (ubiquitin units) are linked together in a head-to-tail arrangement, wherein each monomer of said dimeric protein is differently modified by substitutions of at least 6 amino acids in positions 2, 4, 6, 8, 62, 63, 64, 65, 66 and 68 of SEQ ID NO: 1 wherein said substitutions comprise (1) in the first monomeric unit substitutions at least in amino acid positions 6, 8, 63, 64, 65, and 66; and
in the second monomeric unit substitutions at least in amino acid positions 6, 8, 62, 63, 64, 65, and 66; optionally additionally 2, or (2) in the first monomeric unit substitutions at least in amino acid positions 2, 4, 6, 62, 63, 64, 65, and 66; and
in the second monomeric unit substitutions at least in amino acid positions 6, 8, 62, 63, 64, 65, and 66; optionally additionally 2, and optionally further modifications, preferably substitutions of other amino acids, said modified monomeric ubiquitin unit having an amino acid identity to SEQ ID NO: 1 of at least one of the group of 80%, at least 83%, at least 85%, at least 83% and at least 90%, said protein having a specific binding affinity to said ED-B domain of fibronectin of $Kd=10^{-7}-10^{-12}$ M and exhibits a monovalent binding activity with respect to said extradomain B (ED-B) of fibronectin.

In a preferred embodiment, the protein is recombinant.

In further embodiments of the invention, 7, 8, 9 or all of the amino acids in positions 2, 4, 6, 8, 62, 63, 64, 65, 66, and 68 of SEQ ID NO: 1 are modified in each monomeric ubiquitin unit.

It is to be understood that the present invention allows a combination of each of these variations in each monomeric units, i.e. in the first and the second unit. For instance the first monomeric unit can comprise 6 modifications while the second unit comprises 7 or 8 modifications, the first unit may comprise 8 modifications and the second unit 7 modifications etc. Each of the amino acids listed above can be selected in the first and second unit and both units are then combined. Preferred substitutions are described herein below.

DEFINITIONS OF IMPORTANT TERMS USED IN THE APPLICATION

The term "extra-domain B of fibronectin" or briefly designated as "ED-B" comprises all proteins which show a sequence identity to SEQ ID NO: 2 of at least 70%, optionally 75%, further optionally 80%, 85%, 90%, 95%, 96% or 97% or more, or 100% and having the above defined functionality of ED-B.

The terms "protein capable of binding" or "binding protein" refer to an ubiquitin protein comprising a binding domain to ED-B as further defined below. Any such binding protein based on ubiquitin may comprise additional protein domains that are not binding domains, such as, for example, multimerization moieties, polypeptide tags, polypeptide linkers and/or non-proteinaceous polymer molecules. Some examples of non-proteinaceous polymer molecules are hydroxyethyl starch, polyethylene glycol, polypropylene glycol, or polyoxyalkylene.

Antibodies and fragments thereof are well known to the person skilled in the art. The binding protein of the invention is not an antibody or a fragment thereof, such as Fab or scFv fragments. Further, the binding domain of the invention does not comprise an immunoglobulin fold as present in antibodies.

In the present specification, the terms "ligand" and "target" and "binding partner" are used synonymously and can be exchanged. A ligand is any molecule capable of binding with an affinity as defined herein to the hetero-multimeric modified ubiquitin protein.

The term "ubiquitin protein" covers the ubiquitin in accordance with SEQ ID NO: 1 and modifications thereof according to the following definition. Ubiquitin is highly conserved in eukaryotic organisms. For example, in all mammals investigated up to now ubiquitin has the identical amino acid sequence. Particularly preferred are ubiquitin molecules from humans, rodents, pigs, and primates. Additionally, ubiquitin from any other eukaryotic source can be used. For instance ubiquitin of yeast differs only in three amino acids from the sequence of SEQ ID NO: 1. Generally, the ubiquitin proteins covered by said term "ubiquitin protein" show an amino acid identity of more than 70%, preferably more than 75% or more than 80%, of more than 85%, of more than 90%, of more than 95%, of more than 96% or up to a sequence identity of 97% to SEQ ID NO: 1.

The term "a modified ubiquitin protein" refers to modifications of the ubiquitin protein any one of substitutions, insertions or deletions of amino acids or a combination thereof while substitutions are the most preferred modifications which may be supplemented by any one of the modifications described above. The number of modifications is strictly limited as said modified monomeric ubiquitin units have an amino acid identity to SEQ ID NO: 1 of at least one of the group of 80%, at least 83%, at least 85%, at least 83% and at least 90%. At the most, the overall number of substitutions in a monomeric unit is, therefore, limited to 15 amino acids corresponding to 80% amino acid identity. The total number of modified amino acids in the hetero-dimeric ubiquitin molecule is 30 amino acids corresponding to 20% amino acid modifications based on the hetero-dimeric protein. The amino acid identity of the dimeric modified ubiquitin protein compared to a dimeric unmodified ubiquitin protein with a basic monomeric sequence of SEQ ID NO: 1 is selected from at least one of the group of 80%, at least 83%, at least 85%, at least 83% and at least 90%.

For determining the extent of sequence identity of a derivative of the ubiquitin to the amino acid sequence of SEQ ID NO: 1, for example, the SIM Local similarity program (Xiaoquin Huang and Webb Miller, "Advances in Applied Mathematics, vol. 12: 337-357, 1991) or Clustal, W. can be used (Thompson et al., Nucleic Acids Res., 22(22): 4673-4680, 1994.).

Preferably, the extent of the sequence identity of the modified protein to SEQ ID NO: 1 is determined relative to the complete sequence of SEQ ID NO: 1.

The "hetero-dimeric fusion protein" or "hetero-dimeric protein" of the invention is considered as a protein which comprises two differently modified monomeric ubiquitin proteins with two interacting binding domain regions providing together a monovalent binding property (binding domain) for ED-B as the specific binding partner. A hetero-dimer is accomplished by fusing two monomeric ubiquitin molecules wherein both of these molecules are differently modified as described herein.

An advantage of multimerization of differently modified ubiquitin monomers in order to generate hetero-multimeric binding proteins (here: hetero-dimeric proteins) with monovalent binding activity lies in the increase of the total number of amino acid residues that can be modified to generate a new high affinity binding property to ED-B. The main advantage is that while even more amino acids are modified, the protein-chemical integrity is maintained without decreasing the overall stability of the scaffold of said newly created binding protein to ED-B. The total number of residues which can be modified in order to generate a novel binding site for ED-B is increased as the modified residues can be allocated to two monomeric ubiquitin proteins. The number of modifications can so be two corresponding to the number of modified monomeric ubiquitin molecules. A modular structure of the ubiquitin-based ED-B binding protein allows increasing the overall number of modified amino acids as said modified amino acids are included on two monomeric ubiquitin molecules. The present method provides for the identification of hetero-dimeric ubiquitin molecules having one monovalent specificity (for one single epitope) for ED-B.

Thus, the use of hetero-dimers having a common binding site for binding partners opens up the possibility to introduce an increased number of modified residues which do not unduly influence the protein-chemical integrity of the final binding molecule, since the overall amount of those modified residues is distributed over the two monomeric units which form the dimer. Said hetero-dimeric modified ubiquitin proteins binding to ED-B are present in a library of proteins.

"Monovalent" has to be understood as the capability that both binding regions created in the first and the second monomeric unit of the modified dimeric ubiquitin together bind ED-B in a synergistic and combined manner, i.e. both binding regions act together to form a monovalent binding activity. Taking each binding region of both the first and the second modified ubiquitin in said hetero-dimeric molecule separately will apparently bind ED-B with a much lower efficiency and affinity than the dimeric molecule. Both binding regions form a unique binding site which is formed as a contiguous region of amino acids on the surface of the hetero-dimeric modified ubiquitin protein so that said modified ubiquitin is feasible to bind much more efficient to ED-B than each monomeric protein taken alone. It is particularly important that according to the present invention the two monomeric proteins are not linked together after having screened the most potent binding ubiquitin molecules but that already the screening process is performed in the presence of the hetero-dimeric ubiquitins. After having received the sequence information on the most potent binding ubiquitin molecules, these molecules may be obtained by any other method, e.g. by chemical synthesis or by genetic engineering methods, e.g. by linking the two already identified monomeric ubiquitin units together.

According to the invention, the two differently modified ubiquitin monomers which bind to one ligand are to be linked by head-to-tail fusion to each other using e.g. genetic methods. The differently modified fused ubiquitin monomers bind in a monovalent manner and are only effective if both "binding domain regions" ("BDR") act together. A "binding domain region" is defined herein as region on a ubiquitin monomer that has modified amino acids in at least 6 amino acids of positions 2, 4, 6, 8, 62, 63, 64, 65, 66, 68 of SEQ ID NO:1 which are involved in binding the target.

The modified and linked ubiquitin monomers which form the hetero-dimeric protein bind to the same epitope via a single contiguous binding region. This contiguous region of the heteromer is formed by both binding determining regions of the two modules formed by two differently modified ubiquitin monomers.

A "head to-tail fusion" is to be understood as fusing two proteins together by connecting them in the direction N—C—N—C— depending on the number of units contained in the dimer. In this head-to-tail fusion, the ubiquitin monomers may be connected directly without any linker.

Alternatively, the fusion of ubiquitin monomers can be performed via linkers, for example, a linker having at least the amino acid sequence GIG or having at least the amino acid sequence SGGGG (SEQ ID NO: 48) or any other linker, for example GIG, SGGGG (SEQ ID NO: 48), SGGGGIG (SEQ ID NO: 49), SGGGGSGGGGIG (SEQ ID NO: 32) or SGGGGSGGGG (SEQ ID NO: 50). Also other linkers for the genetic fusion of two ubiquitin monomers are known in the art and can be used.

The modified ubiquitin proteins of the invention are engineered proteins with novel binding affinities to ED-B as target or ligand (which expressions are used herein interchangeably). The term "substitution" comprises also the chemical modification of amino acids by e.g. substituting or adding chemical groups or residues to the original amino acid. The substitution of amino acids in at least one surface-exposed region of the protein comprising amino acids located in at least one beta sheet strand of the beta sheet region or positioned up to 3 amino acids adjacent to the beta sheet strand is crucial.

The substitution of amino acids for the generation of the novel binding domain specific to the ED-B can be performed according to the invention with any desired amino acid, i.e. for the modification to generate the novel binding property to ED-B it is not mandatory to take care that the amino acids have a particular chemical property or a side chain, respectively, which is similar to that of the amino acids substituted so that any amino acid desired can be used for this purpose.

The step of modification of the selected amino acids is performed according to the invention preferably by mutagenesis on the genetic level by random mutagenesis, i.e. a random substitution of the selected amino acids. Preferably, the modification of ubiquitin is carried out by means of methods of genetic engineering for the alteration of a DNA belonging to the respective protein. Preferably, expression of the ubiquitin protein is then carried out in prokaryotic or eukaryotic organisms.

Substitutions are performed particularly in surface-exposed amino acids of the four beta strands of the beta sheets or surface exposed amino acids up to 3 amino acids adjacent to the beta sheet strand of ubiquitin protein. Each beta strand consists usually of 5-7 amino acids. With reference to SEQ ID NO:1, for example, the beta strands usually cover amino acid residues 2-7, 12-16, 41-45 and 65-71. Regions which may be additionally and preferably modified include positions up to 3 amino acids (i.e. 1, 2, or 3) adjacent to the beta sheet strand. The preferred regions which may be additionally and preferably modified include in particular amino acid residues 8-11, 62-64 and 72-75. The preferred regions include beta turns which link two beta strands together. One preferred beta-turn includes amino residues 62-64. A most preferred amino acid which is closely adjacent to the beta sheet strand is the amino acid in position 8. In addition, further preferred examples for amino acid substitutions are positions 36, 44, 70, and/or 71. For example, those regions which may be additionally and preferably modified include amino acids 62, 63, and 64 (3 amino acids), or 72, 73 (2 amino acids), or 8 (1 amino acid).

In preferred embodiments, the amino acid residues are altered by amino acid substitutions. However, also deletions and insertions are allowable. The number of amino acids which may be added or deleted is limited to 1, 2, 3, 4, 5, 6, 7, or 8 amino acids in a monomeric ubiquitin subunit, and accordingly 1, 2, 3, 4, 5, 6, 7, 8, 9, 10, 11, 12, 13, 14, 15, 16 amino acids with respect to the dimeric ubiquitin protein. In one embodiment, no amino acid insertions are made. In a still further embodiment, no deletions have been performed.

Provided that the modified ubiquitin protein of the present invention comprises additionally to said substitutions specified in the claims and explained herein also deletions and/or additions of one or more amino acids, the amino acid positions given for wild type human ubiquitin (SEQ ID NO: 1) have to be aligned with the modified ubiquitin in order to allot the corresponding proteins to each other. In case of fusion proteins (see below), the numbering (and alignment) of each of the monomeric ubiquitin subunits is done in the same way, i.e. an alignment of, for example, a dimer is started at amino acid position 1 for each respective subunit.

In monomeric ubiquitin, preferably from mammals, e.g. human, at least 10% of the amino acids present in beta strands or positions up to 3 amino acids adjacent to the beta sheet strand, preferably at least 20%, further preferably at least 25%, can be modified, preferably substituted, according to the present invention to generate a binding property that did not exist previously. At a maximum, preferably about 50% of the amino acids present in beta strands or positions up to 3 amino acids adjacent to the beta sheet strand, further preferably at a maximum about 40% or about 35% or up to about 30% or up to about 25% are modified, preferably substituted. In one beta strand, generally one to four amino acids are modified. In one embodiment, three of six amino acids in preferably the first and the fourth beta strand, e.g. region of amino acid residues 2-7 or 65-71, are modified.

A modified monomeric ubiquitin according to the invention used as building unit for a hetero-dimer accounts for in total up to 20% of amino acids. Considering this, there is a sequence identity to SEQ ID NO:1 of the modified ubiquitin protein to at least 80%. In further embodiments of the invention, the sequence identity on amino acid level is at least 83%, at least 85%, at least 87% and furthermore at least 90% at least 92% or at least 95% sequence identity to the amino acid sequence of SEQ ID NO: 1. The invention covers also amino acid sequence identities of more than 97% of the modified ubiquitin protein compared to the amino acid sequence of SEQ ID NO: 1.

In a further embodiment of the invention, an ubiquitin is modified in 3 or 4 or 5 or 6 or 7 amino acids in positions 2, 4, 6, 8, 62, 63, 64, 65, 66, and/or 68 of SEQ ID NO: 1. In another embodiment, the ubiquitin to be modified in these positions, was already pre-modified. For example, further modifications could comprise modifications at amino acids 74 and 75 or at amino acid 45 to generate better stability or protein-chemical properties. A modified ubiquitin monomer is obtainable wherein in total up to 9, 10, 11, 12, 13, 14 and a maximum of 15 amino acids of the ubiquitin of SEQ ID NO: 1 are modified, preferably substituted. According to an example, a modified monomeric ubiquitin could be obtained having 14 substitutions and a deletion. Based on the total number of amino acids of ubiquitin this corresponds to a percentage of about 20%. This was extraordinarily surprising and could not be expected since usually a much lower percentage is already sufficient to disturb the folding of the protein.

In one embodiment of the invention, those amino acids are modified for the generation of a region having the novel ED-B binding properties which form a contiguous region on the surface of the protein. In this manner, a contiguous region can be generated which has a binding property to the ED-B. "Contiguous region" according to the invention refers to the following: due to the charge, the spatial structure and the hydrophobicity/hydrophilicity of their side chains, amino acids interact with their environment in the corresponding manner. The environment can be the solvent, generally water, or other molecules, e.g. spatially close amino acids. By means of structural information about the protein as well as the respective software the surface of the proteins can be characterized. For example, the interface region between the atoms of the protein and the solvent can be visualized in this way including the information about how this interface region is structured, which surface areas are accessible to the solvent or how the charges are distributed on the surface. A contiguous region can be revealed for example by visualization of this type using suitable software. Such methods are known to those skilled in the art. According to the invention, basically, also the whole surface-exposed region can be used as the contiguous region on the surface to be modified for the generation of novel binding properties. In one embodiment, for this purpose a modification can also comprise the α-helical region. In a hetero-dimeric modified ubiquitin protein, a binding-determining region comprises two of the surface-exposed regions forming together one contiguous region which comprises two times the length of one binding determining region.

The modification of amino acids in at least one surface-exposed region of the protein comprising at least one beta strand of the beta sheet region or positions up to 3 amino acids adjacent to the beta sheet strand is crucial. The "beta sheet structure" is defined by being essentially sheet-like and almost completely stretched. In contrast to alpha helices which are formed from an uninterrupted segment of the polypeptide chain, beta sheets can be formed by different regions of the polypeptide chain. In this way, regions spaced further apart in the primary structure can get into close proximity with each other. A beta strand typically has a length of 5-10 amino acids (usually 5-6 residues in ubiquitin) and has an almost completely stretched conformation. The beta strands come so close to each other that hydrogen bonds form between the C—O group of one strand and the NH group of the other strand and vice versa. Beta-sheets can be formed from several strands and have a sheet-like structure wherein the position of the C alpha atoms alternates between above or below the sheet-like plane. The amino acid side chains follow this pattern and, thus, alternatively point towards the top or towards the bottom. Depending on the orientation of the beta strands the sheets are classified into parallel and antiparallel sheets. According to the invention both can be mutated and used for the preparation of the proteins claimed.

For the mutagenesis of the beta strands and the beta-sheet structure, a beta strand or positions up to 3 amino acids adjacent to the beta strand (which is a strand of the beta sheet) are selected in the ubiquitin that are close to the surface. Surface-exposed amino acids can be identified with respect to the available X-ray crystallographic structure. If no crystal structure is available attempts can be made by means of computer analysis to predict surface-exposed beta sheet regions and the accessibility of individual amino acid positions with respect to the available primary structure or to model the 3d protein structure and to obtain information about potential surface-exposed amino acids in this manner. Further disclosure thereof can be taken e.g. from J. Mol. Biol., 1987 Apr. 5; 194(3):531-44. Vijay-Kumar S, Bugg C. E., Cook W. J.

It is, however, also possible to carry out modifications in the beta sheet or of positions up to 3 amino acids adjacent to the beta strand for which the time-consuming pre-selection of amino acid positions to be mutagenized can be omitted. Those DNA regions encoding the beta sheet structures or up to 3 amino acids adjacent to the beta sheet strand are isolated from their DNA environment, subjected to random mutagenesis and are afterwards re-integrated into the DNA coding for the protein from which they were removed previously. This is followed by a selection process for mutants with the desired binding properties.

In another embodiment of the invention the beta strands or up to 3 amino acids adjacent to the beta strand close to the surface are selected as already explained above and the amino acid positions to be mutagenized within these selected regions are identified. The amino acid positions selected in this way can then be mutagenized on the DNA level either by site-directed mutagenesis, i.e. a codon coding for a specific amino acid is substituted by a codon encoding another previously selected specific amino acid, or this substitution is carried out in the context of a random mutagenesis wherein the amino acid position to be substituted is defined but not the codon encoding the novel, not yet determined amino acid.

"Surface-exposed amino acids" are amino acids that are accessible to the surrounding solvent. If the accessibility of the amino acids in the protein is more than 8% compared to the accessibility of the amino acid in the model tripeptide Gly-X-Gly, the amino acids are called "surface-exposed". These protein regions or individual amino acid positions, respectively, are also preferred binding sites for potential binding partners for which a selection shall be carried out according to the invention. In addition, reference is made to Caster et al., 1983 Science, 221, 709-713, and Shrake & Rupley, 1973 J. Mol. Biol. 79(2):351-371, which for complete disclosure are incorporated by reference in this application.

Variations of ubiquitin protein scaffold differing by amino acid substitutions in the region of the de novo generated artificial binding site from the parental protein and from each other can be generated by a targeted mutagenesis of the respective sequence segments. In this case, amino acids having certain properties such as polarity, charge, solubility, hydrophobicity or hydrophilicity can be replaced or substituted, respectively, by amino acids with respective other properties. Besides substitutions, the terms "mutagenesis" and "modified" and "replaced" comprise also insertions and deletions. On the protein level the modifications can also be carried out by chemical alteration of the amino acid side chains according to methods known to those skilled in the art.

Methods of Mutagenesis of Ubiquitin

As a starting point for the mutagenesis of the respective sequence segments, for example the cDNA of ubiquitin which can be prepared, altered, and amplified by methods known to those skilled in the art can be used. For site-specific alteration of ubiquitin in relatively small regions of the primary sequence (about 1-3 amino acids) commercially available reagents and methods are on hand ("Quick Change", Stratagene; "Mutagene Phagemid in vitro Mutagenesis Kit", Biorad). For the site-directed mutagenesis of larger regions specific embodiments of e.g. the polymerase chain reaction (PCR) are available to those skilled in the art. For this purpose a mixture of synthetic oligodeoxynucleotides having degenerated base pair compositions at the desired positions can be used for example for the introduction of the mutation. This can also be achieved by using base pair analogs which do not naturally occur in genomic DNA, such as e.g. inosine.

Starting point for the mutagenesis of one or more beta strands of the beta sheet region or positions up to 3 amino acids adjacent to the beta sheet strand can be for example the cDNA of ubiquitin or also the genomic DNA. Furthermore, the gene coding for the ubiquitin protein can also be prepared synthetically.

Different procedures known per se are available for mutagenesis are methods for site-specific mutagenesis, methods for random mutagenesis, mutagenesis using PCR or similar methods.

In a preferred embodiment of the invention the amino acid positions to be mutagenized are predetermined. The selection of amino acids to be modified is carried out to meet the limitations of present claim 1 with respect to those amino acids which have to be modified. In each case, a library of different mutants is generally established which is screened using methods known per se. Generally, a pre-selection of the amino acids to be modified can be particularly easily performed as sufficient structural information is available for the ubiquitin protein to be modified.

Methods for targeted mutagenesis as well as mutagenesis of longer sequence segments, for example by means of PCR, by chemical mutagenesis or using bacterial mutator strains also belong to the prior art and can be used according to the invention.

In one embodiment of the invention the mutagenesis is carried out by assembly of DNA oligonucleotides carrying the amino acid codon NNK. It should be understood, however, that also other codons (triplets) can be used. The mutations are performed in a way that the beta sheet structure is preferably maintained. Generally, the mutagenesis takes place on the outside of a stable beta sheet region exposed on the surface of the protein. It comprises both site-specific and random mutagenesis. Site-specific mutagenesis comprising a relatively small region in the primary structure (about 3-5 amino acids) can be generated with the commercially available kits of Stratagene® (QuickChange®) or Bio-Rad® (Mutagene® phagemid in vitro mutagenesis kit) (cf. U.S. Pat. No. 5,789,166; U.S. Pat. No. 4,873,192).

If more extended regions are subjected to site-specific mutagenesis a DNA cassette must be prepared wherein the region to be mutagenized is obtained by the assembly of oligonucleotides containing the mutated and the unchanged positions (Nord et al., 1997 Nat. Biotechnol. 8, 772-777; McConell and Hoess, 1995 J. Mol. Biol. 250, 460-470.). Random mutagenesis can be introduced by propagation of the DNA in mutator strains or by PCR amplification (error-prone PCR) (e.g. Pannekoek et al., 1993 Gene 128, 135 140). For this purpose, a polymerase with an increased error rate is used. To enhance the degree of the mutagenesis introduced or to combine different mutations, respectively, the mutations in the PCR fragments can be combined by means of DNA shuffling (Stemmer, 1994 Nature 370, 389-391). A review of these mutagenesis strategies with respect to enzymes is provided in the review of Kuchner and Arnold (1997) TIBTECH 15, 523-530. To carry out this random mutagenesis in a selected DNA region also a DNA cassette must be constructed which is used for mutagenesis.

Random modification is performed by methods well-established and well-known in the art. A "randomly modified nucleotide or amino acid sequence" is a nucleotide or amino acid sequence which in a number of positions has been subjected to insertion, deletion or substitution by nucleotides or amino acids, the nature of which cannot be predicted. In many cases the random nucleotides (amino acids) or nucleotide (amino acid) sequences inserted will be "completely random" (e.g. as a consequence of randomized synthesis or PCR-mediated mutagenesis). However, the random sequences can also include sequences which have a common functional feature (e.g. reactivity with a ligand of the expression product) or the random sequences can be random in the sense that the ultimate expression product is of completely random sequence with e.g. an even distribution of the different amino acids.

In order to introduce the randomized fragments properly into the vectors, it is according to the invention preferred that the random nucleotides are introduced into the expression vector by the principle of site directed PCR-mediated mutagenesis. However, other options are known to the skilled person, and it is e.g. possible to insert synthetic random sequence libraries into the vectors as well.

To generate mutants or libraries by fusion PCR, for example three PCR reactions may carried out. Two PCR reactions are performed to generate partially overlapping intermediate fragments. A third PCR reaction is carried out to fuse the intermediate fragments.

The method for construction the library or mutant variants may include constructing a first set of primers around a desired restriction site (restriction site primer), a forward and reverse restriction primer and a second set of primers around, e.g., upstream and downstream of the codon of interest (the mutagenic primers), a forward and reverse mutagenic primer. In one embodiment, the primers are constructed immediately upstream and downstream respectively of the codon of interest. The restriction and mutagenic primers are used to construct the first intermediate and second intermediate fragments. Two PCR reactions produce these linear intermediate fragments. Each of these linear intermediate fragments comprises at least one mutated codon of interest, a flanking nucleotide sequence and a digestion site. The third PCR reaction uses the two intermediate fragments and the forward and reverse restriction primers to produce a fused linear product. The opposite, here to for unattached ends of the linear product are digested with a restriction enzyme to create cohesive ends on the linear product. The cohesive ends of the linear product are fused by use of a DNA ligase to produce a circular product, e.g. a circular polynucleotide sequence.

To construct the intermediate fragments, the design and synthesis of two sets of forward and reverse primers are performed, a first set containing a restriction enzymes digestion site together with its flanking nucleotide sequence, and the second set contains at least one variant codon of interest (mutagenic primers). Those skilled in the art will recognize that the number of variants will depend upon the number of variant amino acid modifications desired. It is contemplated by the inventor that if other restriction enzymes are used in the process, the exact location of this digestion site and the corresponding sequence of the forward and reverse primers may be altered accordingly. Other methods are available in the art and may be used instead.

Apart from having the randomized fragment of the expression product introduced into a scaffold in accordance with the present invention, it is often necessary to couple the random sequence to a fusion partner by having the randomized nucleotide sequence fused to a nucleotide sequence encoding at least one fusion partner. Such a fusion partner can e.g. facilitate expression and/or purification/isolation and/or further stabilization of the expression product.

Random substitution of amino acids according to one example of the present invention of at least 6 amino acids at positions 2, 4, 6, 8, 62, 63, 64, 65, 66, and/or 68 of monomeric ubiquitin can be performed particularly easily by means of PCR since the positions mentioned are localized close to the amino or the carboxy terminus of the protein. Accordingly, the codons to be manipulated are at the 5' and 3' end of the corresponding cDNA strand. Thus, the first oligodeoxynucleotide used for a mutagenic PCR reaction apart from the codons at positions 2, 4, 6, and/or 8 to be mutated—corresponds in sequence to the coding strand for the amino terminus of ubiquitin. Accordingly, the second oligodeoxynucleotide—apart from the codons of positions 62, 63, 64, 65, 66, and/or 68 to be mutated—at least partially corresponds to the non-coding strand of the polypeptide sequence of the carboxy terminus. By means of both oligodeoxynucleotides a polymerase chain reaction can be performed using the DNA sequence encoding the monomeric ubiquitin as a template.

Furthermore, the amplification product obtained can be added to another polymerase chain reaction using flanking oligodeoxynucleotides which introduce for example recognition sequences for restriction endonucleases. It is preferred according to the invention to introduce the gene cassette obtained into a vector system suitable for use in the subsequent selection procedure for the isolation of ubiquitin variations having binding properties to a predetermined hapten or antigen.

Regions to be Modified in Ubiquitin

The regions for modification can be basically selected as to whether they can be accessible for ED-B as binding partner and whether the overall structure of the protein will presumably show tolerance to a modification.

Besides modifications in surface-exposed beta strands also modifications in other surface-exposed regions of the protein can be carried out, preferably in positions up to 3 amino acids adjacent to the beta strand. These modified regions are involved in the newly generated binding with high affinity to ED-B.

In another optional embodiment of the present invention amino acids in one or two, preferably two of the four beta strands in the protein or positions up to 3 amino acids adjacent to preferably two of the four beta strands are modified to generate a novel binding property. Also optional is a modification in three or four of the four beta strands or positions up to 3 amino acids adjacent to three or four of the beta strands for the generation of an ED-B binding.

It is particularly preferred that amino acids in the amino-terminal and carboxy-terminal strand or in positions up to 3 amino acids adjacent to the amino-terminal and carboxy-terminal strand are modified, preferably substituted, to generate a novel binding site to ED-B. In this respect, it is particularly preferred that up to 4 amino acids adjacent to the carboxy-terminal beta sheet strand are modified, preferably substituted, and up to 1 amino acid adjacent to the amino-terminal beta sheet strand is modified, preferably substituted.

Particularly preferred is a modification, preferably a substitution, in at least three surface-exposed amino acids of the following positions of a mammalian ubiquitin, preferably human ubiquitin: 2, 4, 6, 8, 62, 63, 64, 65, 66, 68. These at least four amino acids from said group of amino acids form a contiguous surface-exposed region on the surface of ubiquitin which was found to be particularly suitable for the generation of modified proteins having a binding affinity that did not exist previously with respect to the ED-B as binding partner. At least 3 of these amino acid residues have to be modified. Optionally 3, 4, 5, 6, 7, 8, 9 or 10 of said amino acid residues are modified, optionally in combination with additional amino acid residues.

After having made the modifications above, the inventors have found the amino acid modified ubiquitin sequences described in the examples which bind ED-B with very high affinity (Kd values up to $10^{-9}$).

Fusion Proteins

In another preferred embodiment, the invention relates to a fusion protein comprising a binding protein of the invention fused to a pharmaceutically and/or diagnostically active component.

In a still further aspect, the invention relates to a fusion protein comprising a hetero-dimericbinding protein of the invention fused to a pharmaceutically and/or diagnostically active component. A fusion protein of the invention may comprise non-polypeptide components, e.g. non-peptidic linkers, non-peptidic ligands, e.g. for therapeutically or diagnostically relevant radionuclides. It may also comprise small organic or non-amino acid based compounds, e.g. a sugar, oligo- or polysaccharide, fatty acid, etc. In one preferred embodiment of the invention, the heteromeric ubiquitin-based ED-B binding molecule is covalently or non-covalently conjugated to a protein or peptide having therapeutically or diagnostically relevant properties.

The following gives some examples on how to obtain ubiquitin-based fusion proteins with ED-B binding capacity.
 a) conjugation of the protein via Lysine residues present in ubiquitin;
 b) conjugation of the heterodimeric ubiquitin-based binding protein via Cysteine residues—can be located C-terminal, or at any other position (e.g. amino acid residue 24 or 57); conjugation with maleimid selectable components;
 c) peptidic or proteinogenic conjugations—genetic fusions (preferred C- or N-terminal);
 d) "Tag"-based fusions—A protein or a peptide located either at the C- or N-terminus of the target protein ED-B. Fusion "tags", e.g. poly-histidine (particularly relevant for radio labeling).

These and other methods for covalently and non-covalently attaching a protein of interest to a support are well known in the art, and are thus not described in further detail here.

Optionally, said active component is a cytokine, preferably a cytokine selected from the group consisting of tumor necrosis factors (e.g. TNF alpha, TNF beta), interleukins (e.g. IL-2, IL-12, IL-10, IL-15, IL-24, IL-3, IL-4, IL-5, IL-6, IL-7, IL-9, IL-11, IL-13, IL-8, IL-1 alpha, IL-1beta), interferons (e.g. IFN alpha, IFN beta, IFN gamma), GM-CSF, GRO (GRO alpha, GRO beta, GRO gamma,), MIP (MIP-1-alpha, MIP-1 beta, MIP-3 alpha, MIP-3 beta), TGF-beta LIFT CD80, CD-40 ligand, B70, LT-beta, Fas-ligand, ENA-78, LDGF-PBP, GCP-2, PF4, Mig, IP-10, SDF-1 alpha/beta, BUNZO/STRC33, I-TAC, BLC/BCA-1, MDC, TECK, TARC, RANTES, HCC-1, HCC-4, DC-CK1, MCP-1-5, Eotaxin, Eotaxin-2, I-309, MPIF-1, 6Ckine, CTACK, MEC, Lymphotactin, Fractalkine, and others.

One of the most preferred cytokines for use in the present invention is TNF alpha. The inflammatory cytokine TNF has multiple activities in the mammalian body including an anti-tumor effect that is currently clinically irrelevant due to unacceptable toxicity of effective doses in humans. Currently, TNF is therapeutically used in combination with cytostatic substances like Melphalan.

Further optionally, said active component that can be conjugated to the hetero-multimeric ubiquitin-based binding protein is a toxic compound, preferably a small organic compound or a polypeptide, optionally a toxic compound, for example, selected from the group consisting of saporin, truncated *Pseudomonas* exotoxin A, recombinant gelonin, Ricin-A chain, calicheamicin, neocarzinostatin, esperamicin, dynemicin, kedarcidin, maduropeptin, doxorubicin, daunorubicin, auristatin, cholera toxin, modeccin, diphtheria toxin.

In a further embodiment of the invention the hetero-multimeric ubiquitin-based binding protein according to the invention may contain artificial amino acids.

In further embodiments of the fusion protein of the present invention said active component is a fluorescent dye, preferably a component selected from the groups of a radionuclide either from the group of gamma-emitting isotopes, preferably $99_{Tc}$, $123_I$, $111_{In}$, or from the group of positron emitters, preferably $18_F$, $64_{Cu}$, $68_{Ga}$, $86_Y$, $124_I$, or from the group of beta-emitter, preferably $131_I$, $90_Y$, $177_{Lu}$, $67_{Cu}$, or from the group of alpha-emitter, preferably $213_{Bi}$, $211_{At}$; Alexa Fluor or Cy dyes (Berlier et al., J Histochem Cytochem. 51 (12): 1699-1712, 2003); a photosensitizer; a pro-coagulant factor, preferably tissue factor (e.g. tTF truncated tissue factor); an enzyme for pro-drug activation, preferably an enzyme selected from the group consisting of carboxy-peptidases, glucuronidases and glucosidases; and/or a functional Fc domain, preferably a human functional Fc domain.

A further embodiment relates to fusion proteins according to the invention, further comprising a component modulating serum half-life, preferably a component selected from the group consisting of polyethylene glycol, albumin-binding peptides, and immunoglobulin.

Binding Specificities (Dissociation Constants)

The binding specificities of the fusion proteins according to the invention are as defined above for the non-fusion protein given in Kd. In accordance with the invention, the term "Kd" defines the specific binding affinity which is in accordance with the invention in the range of $10^{-7}$-$10^{-12}$ M. A value of $10^{-5}$ M and below can be considered as a quantifiable binding affinity. Depending on the application a value of $10^{-7}$ M to $10^{-11}$ M is preferred for e.g. chromatographic applications or $10^{-9}$ to $10^{-12}$ M for e.g. diagnostic or therapeutic applications. Further preferred binding affinities are in the range of $10^{-7}$ to $10^{-10}$ M, preferably to $10^{-11}$ M.

The methods for determining the binding affinities are known per se and can be selected for instance from the following methods: ELISA, Surface Plasmon Resonance (SPR) based technology (offered for instance by BIACORE®), fluorescence spectroscopy, isothermal titration calorimetry (ITC), analytical ultracentrifugation, FACS.

After having made the modifications above, the inventors have found the amino acid modified ubiquitin sequences described in the examples which bind their targets with very high affinity (Kd values up to $10^{-10}$ M).

Dimerization of Ubiquitin

A "dimer" is considered as a protein in this invention which comprises two monomeric ubiquitin proteins. If the dimer comprises two differently modified monomers, it is called a "heteromeric-dimer" or "hetero-dimer". Thus, the "hetero-dimer" of the invention is considered as a fusion of two differently modified monomeric ubiquitin proteins exhibiting a combined monovalent binding property for the specific binding partner ED-B. It is emphasized that the modified hetero-dimeric ED-B binding ubiquitin protein of the invention is not obtained by separately screening each monomeric ubiquitin protein and combining two of them afterwards but by screening for hetero-dimeric proteins consisting of a first and a second monomeric unit which exhibit together a monovalent binding activity of said ED-B ligand. It is to be expected that each of said subunits exhibit a quite limited binding affinity towards ED-B while only the combined dimeric modified ubiquitin protein will have the excellent binding properties described herein (see, for example, FIGS. 4A and 4B).

According to the invention two differently modified ubiquitin monomers genetically linked by head-to-tail fusion bind to the same epitope of ED-B and are only effective if both binding domain regions act together. The BDRs of the monomers form a single contiguous binding region.

Thus, the ubiquitin protein modified in accordance with the invention to efficiently bind ED-B of fibronectin is dimerized.

The monomers can be connected directly or via linkers, as discussed above. Many conceivable linkers can be used.

Each monomeric ubiquitin shows modifications in at least six of amino acids 2, 4, 6, 8, 62, 63, 64, 65, 66, 68. The monomeric proteins are genetically fused to each other. The binding to the target is mediated by said BDRs in collaboration, i.e. the BDRs cooperate and form a single and common binding region capable of binding to said ED-B domain of fibronectin in a monovalent manner.

Modified Ubiquitin Hetero-Dimers Bind to ED-B

The hetero-dimer of ubiquitin according to the invention binding to ED-B with $Kd=10^{-7}\text{-}10^{-12}M$ and exhibiting a monovalent binding activity with respect to said extradomain B (ED-B) of fibronectin is selected from the following two alternatives:

(1) in the first monomeric unit substitutions at least in amino acid positions 6, 8, 63, 64, 65, and 66; and
in the second monomeric unit substitutions at least in amino acid positions 6, 8, 62, 63, 64, 65, and 66; optionally additionally 2, and
(2) in the first monomeric unit substitutions at least in amino acid positions 2, 4, 6, 62, 63, 64, 65, and 66; and
in the second monomeric unit substitutions at least in amino acid positions 6, 8, 62, 63, 64, 65, and 66; optionally additionally 2.

In an embodiment, the fusion protein is a genetically fused hetero-dimer of said ubiquitin monomer having amino acids substitutions in positions 6, 8, 63-66 of the first ubiquitin monomer and substitutions in amino acid residues in positions 6, 8, 62-66, and optionally in position 2 of the second ubiquitin monomer, preferably in the first ubiquitin monomer substitutions
Lysine (K) to Tryptophane (W) or Phenylalanine (F) in position 6,
Leucine (L) to Tryptophane or Phenylalanine (W, F) in position 8,
Lysine (K) to Arginine (R) or Histidine (H) in Position 63,
Glutamic acid (E) to Lysine (K), Arginine (R) or Histidine (H) in position 64,
Serine (S) to Phenylalanine (F) or Tryptophane (W) in position 65 and
Threonine (T) to Proline (P) in position 66;
in the second ubiquitin monomer, the substitutions
Lysine (K) to Threonine (T), Asparagine (N), Serine (S) or Glutamine (Q) in position 6,
Leucine (L) to Glutamine (Q) or Threonine (T) or Asparagine (N) or Serine (S) in position 8,
Glutamine (Q) to Trytophane (W) or Phenylalanine (F) in position 62,
Lysine (K) to Serine (S), Threonine (T), Asparagine (N) or Glutamine (Q) in position 63,
Glutamic acid (E) to Asparagine (N), Serine (S), Threonine (T), or Glutamine (Q) in position 64,
Serine (S) to Phenylalanine (F) or Tryptophane (W) in position 65, and
Threonine (T) to Glutamic acid (E) or Aspartic acid (D) in position 66, and
Optionally Glutamine (Q) to Arginine (R), Histidine (H) or Lysine (K) in position 2 are preferred.

These alternative substitutions in each monomer can be combined with each other without any limitations provided that the resulting modified ubiquitin hetero-dimers show a specific binding affinity to said extradomain B (ED-B) of fibronectin of $Kd=10^{-7}\text{-}10^{-12}$ M and exhibit a monovalent binding activity with respect to said extradomain B (ED-B) of fibronectin and provided that the structural stability of the ubiquitin protein is not destroyed or hampered.

Most preferred are the following substitutions:
(1) in the first monomeric unit at least—K6W, L8W, K63R, E64K, S65F, and T66P; and in the second monomeric unit at least—K6T, L8Q, Q62W, K63S, E64N, S65W, and T66E; optionally additionally Q2R, or
(2) in the first monomeric unit at least Q2T, F4W, K6H, Q62N, K63F, E64K, S65L, and T66S.;
and in the second monomeric unit at least—K6X, L8x, Q62X, K63X, E64X, S65X, and T66X; optionally additionally Q2X, wherein X can be any amino acid (see FIG. 2).

Particularly preferred are the following substitutions in the first ubiquitin monomer to generate binding proteins for ED-B
2: Q→T, 4: F→W, 6: K→H, 62: Q→N, 63: K→F, 64: E→K, 65: S→L, 66: T→S Either no linker or any linker can be used to connect the two monomers head-to-tail. Preferred linkers are those of SEQ ID NO: 32 or the sequence GIG or SGGGGIG (SEQ ID NO: 49) or SGGGGSGGGGIG (SEQ ID NO: 32).

In a preferred embodiment, a ubiquitin hetero-dimer with two binding determining regions (BDR) acting together for binding ED-B comprises the amino acid sequence of SEQ ID NO: 33 or 34. A further preferred protein is provided by the following sequence wherein X may be any amino acid (SEQ ID NO: 47). As linker, SGGGGSGGGGIG (SEQ ID NO: 32) was used here: It is to be understood that also other kind of linkers or no linker are feasible alternatives.

```
                                            (SEQ ID NO: 51)
MTIWVHTLTGKTITLEVEPSDTIENVKAKIQDKEGIPPDQQRLIWAGKQL

EDGRTLSDYNINFKLSLHLVLRLRGGSGGGGSGGGGIGMQIFVXTXTGKT

ITLEVEPSDTIENVKAKIQDKEGIPPDQQRLIWAGKQLEDGRTLSDYNIX

XXXXLHLVLRLRGG
```

The consensus sequences of examples of proteins with these sequences are shown in FIG. 2.

A preferred fusion protein of the invention comprising TNF-alpha as a pharmaceutically active component has the sequence of SEQ ID NO: 35 or 36.

In a further aspect of the invention, the present invention covers also polynucleotides which encode for a protein or fusion protein as described before. Additionally, vectors comprising said polynucleotide are covered by the invention.

In an additional aspect of the present invention, host cells are covered which comprise a protein or a fusion protein described herein and/or a polynucleotide coding for said recombinant protein or fusion protein of the invention or a vector containing said polynucleotide.

Uses of the Proteins of the Invention, e.g. Hetero-Dimeric Ubiquitin Based Binding Proteins Specifically for ED-B Fused to an Effector Such as TNF Alpha The modified ubiquitin ED-B binding proteins of the invention are to be used for instance for preparing diagnostic means for in vitro or in vivo use as well as therapeutic means. The proteins according to the invention can be used e.g. as direct effector molecules (modulator, antagonist, agonist) or antigen-recognizing domains. Examples of tumors with abundant appearance of ED-B antigen are shown in the table of FIG. 1.

Depending on the selected fusion partner the pharmaceutical composition of the invention is adapted to be directed to the treatment of cancer, e.g. breast and colorectal cancers, or any other tumor diseases in which ED-B is abundant (cf. examples thereof listed in FIG. 1).

The compositions are adapted to contain a therapeutically effective dose. The quantity of the dose to be administered depends on the organism to be treated, the type of disease, the age and weight of the patient and further factors known per se.

The compositions contain a pharmaceutically or diagnostically acceptable carrier and optionally can contain further auxiliary agents and excipients known per se. These include for example but not limited to stabilizing agents, surface-active agents, salts, buffers, colouring agents etc.

The pharmaceutical composition can be in the form of a liquid preparation, a cream, a lotion for topical application, an aerosol, in the form of powders, granules, tablets, suppositories, or capsules, in the form of an emulsion or a liposomal preparation. The compositions are preferably sterile, non-pyrogenic and isotonic and contain the pharmaceutically conventional and acceptable additives known per se. Additionally, reference is made to the regulations of the U.S. Pharmacopoeia or Remington's Pharmaceutical Sciences, Mac Publishing Company (1990).

In the field of human and veterinary medical therapy and prophylaxis pharmaceutically effective medicaments containing at least one heteromeric ED-B binding ubiquitin protein modified in accordance with the invention can be prepared by methods known per se. Depending on the galenic preparation these compositions can be administered parentally by injection or infusion, systemically, rectally, intraperitoneally, intramuscularly, subcutaneously, transdermally or by other conventionally employed methods of application. The type of pharmaceutical preparation depends on the type of disease to be treated, the severity of the disease, the patient to be treated and other factors known to those skilled in the art of medicine.

In an embodiment, the pharmaceutical composition contains a protein or a fusion protein of the invention or a combination thereof and further comprises one or more chemotherapeutic agents, preferably selected from the following table:

| Substance Class | Examples |
| --- | --- |
| Alkylating agents (ATC L01A) | melphalan, cyclophosphamide |
| Antimetabolites (ATC L01B) | 5-fluorouracil, gemcitabine |
| Taxanes (ATC L01CD) | Paclitaxel |
| Cytotoxic antibiotics (ATC L01D) | doxorubicin, liposomal doxorubicin |
| Platinum compounds (ATC L01XA) | Cisplatin |

In a preferred embodiment, the chemotherapeutic agent is selected from melphalan, doxorubicin, cyclophosphamide, dactinomycin, fluorodesoxyuracil, cisplatin, paclitaxel, and gemcitabine; or from the group of kinase inhibitors.

A "pharmaceutical composition" according to the invention may be present in the form of a composition, wherein the different active ingredients and diluents and/or carriers are in admixed with each other, or may take the form of a combined preparation, where the active ingredients are present in partially or totally distinct form. An example for such a combination or combined preparation is a kit-of-parts.

A "composition" according to the present invention comprises at least two pharmacologically active compounds. These compounds can be administered simultaneously or separately with a time gap of one minute to several days. The compounds can be administered via the same route or differently; e.g. oral administration of one active compound and parenteral administration of another are possible. Also, the active compounds may be formulated in one medicament, e.g. in one infusion solution or as a kit comprising both compounds formulated separately. Also, it is possible that both compounds are present in two or more packages.

A particularly preferred combination is a fusion protein according to the invention and melphalan, and/or (liposomal) doxorubicin. Apart from antineoplastic agents from the ATC class L01, the TNF-fusion protein of the invention can be combined with other antineoplastic substances including cytokines and derivatives thereof, radiopharmaceuticals, cell based therapeutics and nanoparticles.

Due to its tumor permeabilisation activity, the TNF-fusion protein of the invention (but also the other recombinant proteins/fusion proteins of the present invention) can be combined with all antineoplastic agents as listed under L01 in the Anatomical Therapeutic Chemical Classification System (ATC) provided by the World Health Organisation.

It surprisingly turned out that a fusion protein of a ubiquitin hetero-dimer fused to TNF-alpha, wherein the fusion protein preferably has the sequence of SEQ ID NO: 35 or 36, can be advantageously applied in therapy. TNF-alpha is highly toxic and, thus, may only be administered in low dosages, which usually lie below the minimum therapeutic threshold (and thus are therapeutically inactive). Due to this toxicity of TNF-alpha, in order to reach a therapeutically effective concentration, the isolated limb perfusion approach presently is selected when using TNF-alpha. Limb perfusion is a medical technique that may be used to deliver anticancer drugs directly to an arm or leg. The flow of blood to and from the limb is temporarily stopped with a tourniquet, and anticancer drugs are put directly into the blood of the limb. This allows the patient to receive a high dose of TNF-alpha in the area where the cancer occurred.

However, by applying the TNF-alpha fusion proteins of the present invention, it is possible to administer TNF-alpha in a non-toxic, but still therapeutically effective concentration. Since TNF-alpha is coupled to the (binding) fusion protein of the present invention, it can be directly active at the disease site (for example, tumor site) and, thus, the amount of "free" TNF-alpha can be drastically reduced.

The systemic side effects of TNF-alpha can be remarkably reduced by administering TNF-alpha as a fusion protein according to the present invention. By using a TNF-alpha fusion protein of the invention, the overall dosage of TNF-alpha to reach a therapeutic effect thus can be reduced to a large extent and can be advantageously used for systemic tumor treatment (without the necessity and restrictions of limb perfusion) in particular in combination with chemotherapeutic agents (see above).

In a further embodiment, the pharmaceutical composition is in the form of a kit of parts, providing separated entities for the recombinant ubiquitin protein/fusion protein of the invention and for the one or more chemotherapeutic agents.

Method of Production of the Hetero-Dimeric ED-B Binding Proteins of the Invention ED-B binding proteins according to the invention may be prepared by any of the many conventional and well known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

In another aspect of the present invention, a method for generating a recombinant modified ubiquitin protein is provided. The method comprises at least the following steps:
  a) providing a population of differently modified dimeric ubiquitin proteins originating from monomeric ubiquitin proteins, said population comprising dimeric ubiquitin proteins comprising two modified ubiquitin monomers linked together in a head-to-tail arrangement wherein each monomer of said dimeric protein is differently modified by substitutions of at least 6 amino acids in positions 2, 4, 6, 8, 62, 63, 64, 65, 66 and 68 of SEQ ID NO: 1
wherein said substitutions comprise
(1) in the first monomeric unit substitutions at least in amino acid positions 6, 8, 63, 64, 65, and 66; and
in the second monomeric unit substitutions at least in amino acid positions 6, 8, 62, 63, 64, 65, and 66; optionally additionally 2; or
(2) in the first monomeric unit substitutions at least in amino acid positions 2, 4, 6, 62, 63, 64, 65, and 66; and
in the second monomeric unit substitutions at least in amino acid positions 6, 8, 62, 63, 64, 65, and 66; optionally additionally 2
b) providing the extradomain B (ED-B) of fibronectin as potential ligand;
c) contacting said population of differently modified proteins with said extradomain B (ED-B) of fibronectin;
d) identifying a modified dimeric ubiquitin protein by a screening process, wherein said modified dimeric ubiquitin protein binds to said the extradomain B (ED-B) of fibronectin with a specific binding affinity of Kd in a range of $10^{-7}$-$10^{-12}$M and exhibits a monovalent binding activity with respect to said extradomain B (ED-B) of fibronectin, and optionally
e) isolating said modified dimeric ubiquitin protein with said binding affinity.

Optionally, the modification may be performed by genetic engineering on the DNA level and expression of the modified protein in prokaryotic or eukaryotic organisms or in vitro.

In a further embodiment, said modification step includes a chemical synthesis step.

In one aspect of the invention, said population of differently modified proteins is obtained by genetically fusing two DNA libraries encoding each for differently modified monomeric ubiquitin proteins.

In a still further aspect, said method is adapted in order that said modified hetero-dimeric ubiquitin protein is fused with a pharmaceutically active component, optionally a cytokine, preferably TNF-alpha, or a diagnostic component, or wherein said recombinant modified hetero-dimeric ubiquitin protein is formed via said pharmaceutically active component which is optionally TNF-alpha, or via said diagnostic component.

According to the invention, a modified protein can further be prepared by chemical synthesis. In this embodiment the steps c) to d) of claim 1 are then performed in one step.

In a further aspect, the present invention is directed to a library containing DNA encoding for modified monomeric ubiquitin proteins as defined above which form the basis for providing the hetero-dimeric ubiquitin proteins of the invention.

In a still further aspect of the invention, a fusion library containing DNA obtained by fusing two libraries as specified above is provided each library encoding for differently modified monomeric ubiquitin protein units in order to obtain hetero-dimeric ubiquitin fusion proteins, the monomeric units thereof being linked together in a head-to-tail arrangement, said library encoding for hetero-dimeric fusion proteins of ubiquitin exhibiting a monovalent binding activity with respect to said extradomain B (ED-B) of fibronectin. Said linking together is performed either by using anyone of the linkers known by the skilled artisan or a linker described herein. In one embodiment of the invention TNF-alpha is used as linker acting simultaneously as pharmaceutically active compound.

Example 1 outlines the production of a complex library. However, care must be taken as regards the quality of such a library. Quality of a library in scaffold technology is in the first place dependent from its complexity (number of individual variants) as well as functionality (structural and protein-chemical integrity of the resulting candidates). Both characteristics, however, may exert negative influences on each other: enhancing the complexity of a library by increasing the number of modified positions on the scaffold might lead to a deterioration of the protein-chemical characteristics of the variants. This might result in a decreased solubility, aggregation and/or low yields. A reason for this is the larger deviation from native scaffolds having an energetically favourable protein packaging.

Therefore, it is a balancing act to construct such a scaffold library suitably between the extreme positions of introducing as many variations as possible into the original sequence in order to optimize it for a target and, on the other hand, of conserving the original primary sequence as much as possible in order to avoid negative protein-chemical effects.

It is noted that the present disclosure encompasses also each conceivable combination of the features described herein in view of the aspects or embodiments of the invention. Selection of the Modified Ubiquitin Proteins with Binding Affinity with Respect to the Target ED-B and Determination of the Modified Amino Acids Responsible for the Binding Affinity After e.g. at least two different DNA libraries encoding for hetero-dimeric modified ubiquitin proteins have been established by differently modifying selected amino acids in each of the monomeric ubiquitin units, these libraries are genetically fused by e.g. linker technology to obtain DNA molecules encoding for hetero-dimeric modified ubiquitin proteins. The DNA of these libraries is expressed into proteins and the modified dimeric proteins obtained thereby are contacted according to the invention with the ED-B to optionally enable binding of the partners to each other if a binding affinity does exist.

It is a crucial aspect of the invention that the contacting and screening process is performed already with respect to the hetero-dimeric ubiquitin protein. This process enables screening on those ubiquitin proteins which provide a monovalent binding activity to ED-B.

Contacting according to the invention is preferably performed by means of a suitable presentation and selection method such as the phage display, ribosomal display, mRNA display or cell surface display, yeast surface display or bacterial surface display methods, preferably by means of the phage display method. For complete disclosure, reference is made also to the following references: Hoess, Curr. Opin. Struct. Biol. 3 (1993), 572-579; Wells and Lowmann, Curr. Opin. Struct. Biol. 2 (1992), 597-604; Kay et al., Phage Display of Peptides and Proteins-A Laboratory Manual (1996), Academic Press. The methods mentioned above are known to those skilled in the art and can be used according to the invention including modifications thereof.

The determination whether the modified protein has a quantifiable binding affinity with respect to a predetermined binding partner can be performed according to the invention preferably by one or more of the following methods: ELISA, plasmon surface resonance spectroscopy, fluorescence spectroscopy, FACS, isothermal titration calorimetry and analytical ultracentrifugation.

Phage Display Selection Method

One type of phage display procedure adapted to this application is described in the following as an example for a selection procedure according to the invention with respect to variations of ubiquitin which show binding properties. In the same manner e.g. methods for the presentation on bacteria (bacterial surface display; Daugherty et al., 1998, Protein Eng. 11(9):825-832) or yeast cells (yeast surface display; Kieke et al., 1997 Protein Eng. 10(11):1303-10) or cell-free selection systems such as the ribosome display (Hanes and Plückthun, 1997 Proc Natl Acad Sci USA. 94(10):4937-4942; He and Taussig, 1997 Nucleic Acids Res. 25(24):5132-5134) or the cis display (Odegrip et al., 2004 Proc Natl Acad Sci USA. 101(9):2806-2810) or the mRNA display can be applied. In the latter case a transient physical linkage of genotype and phenotype is achieved by coupling of the protein variation to the appropriate mRNA via the ribosome.

In the phage display procedure described herein recombinant variations of ubiquitin are presented on a filamentous phage while the coding DNA of the presented variation is present at the same time packed in a single-stranded form in the phage envelope. Thus, in the frame of an affinity enrichment variations having certain properties can be selected from a library and their genetic information can be amplified by infection of suitable bacteria or added to another cycle of enrichment, respectively. Presentation of the mutated ubiquitin on the phage surface is achieved by genetic fusion to an amino-terminal signal sequence-preferably the Pe1B signal sequence- and a capsid or surface protein of the phage-preferred is the carboxyterminal fusion to the capsid protein pIII or a fragment thereof. Furthermore, the encoded fusion protein can contain further functional elements such as e.g. an affinity tag or an antibody epitope for detection and/or purification by affinity chromatography or a protease recognition sequence for specific cleavage of the fusion protein in the course of the affinity enrichment. Furthermore, an amber stop codon can be present for example between the gene for the ubiquitin variation and the coding region of the phage capsid protein or the fragment thereof which is not recognized during translation in a suitable suppressor strain partially due to the introduction of one amino acid.

The bacterial vector suitable for the selection procedure in the context of the isolation of ubiquitin variations with binding properties to ED-B and into which the gene cassette for the fusion protein described is inserted is referred to as phagemid. Among others, it contains the intergenic region of a filamentous phage (e.g. M13 or f1) or a portion thereof which in the case of a superinfection of the bacterial cell carrying the phagemid by means of helper phages such as e.g. M13K07 results in the packaging of a closed strand of phagemid DNA into a phage capsid. The phagemids generated in this manner are secreted by the bacterium and present the respective ubiquitin variation encoded-due to its fusion to the capsid protein pIII or the fragment thereof-on their surface. Native pIII capsid proteins are present in the phagemid so that its ability to re-infect suitable bacterial strains and therefore the possibility to amplify the corresponding DNA is retained. Thus, the physical linkage between the phenotype of the ubiquitin variation—i.e. its potential binding property—and its genotype is ensured.

Phagemids obtained can be selected with respect to the binding of the ubiquitin variation presented thereon to ED-B by means of methods known to those skilled in the art. For this purpose, the presented ubiquitin variations can be transiently immobilized to target substance bound e.g. on microtiter plates and can be specifically eluted after non-binding variations have been separated. The elution is preferably performed by basic solutions such as e.g. 100 mM triethylamine. Alternatively, the elution can be performed under acidic conditions, by proteolysis or direct addition of infected bacteria. The phagemids obtained in this manner can be re-amplified and enriched by successive cycles of selection and amplification of ubiquitin variations with binding properties to ED-B.

Further characterization of the ubiquitin variations obtained in this way can be performed in the form of the phagemid, i.e. fused to the phage, or after cloning of the corresponding gene cassette into a suitable expression vector in the form of a soluble protein. The appropriate methods are known to those skilled in the art or described in the literature. The characterization can comprise e.g. the determination of the DNA sequence and thus of the primary sequence of the variations isolated. Furthermore, the affinity and specificity of the variations isolated can be detected e.g. by means of biochemical standard methods such as ELISA or plasmon surface resonance spectroscopy, fluorescence spectroscopy, FACS, isothermal titration calorimetry, analytical ultracentrifugation or others. In view of the stability analysis, for example spectroscopic methods in connection with chemical or physical unfolding are known to those skilled in the art.

Ribosomal Display Selection Method

In a further embodiment of the invention ribosomal display procedure variations of ubiquitin are prepared by means of a cell-free transcription/translation system and presented as a complex with the corresponding mRNA as well as the ribosome. For this purpose, a DNA library as described above is used as a basis in which the genes of variations are present in form of fusions with the corresponding regulatory sequences for expression and protein biosynthesis. Due to the deletion of the stop codon at the 3' end of the gene library as well as suitable experimental conditions (low temperature, high $Mg^{2+}$ concentration) the ternary complex consisting of the nascent protein, the mRNA and the ribosome is maintained during in vitro transcription/translation.

After a protein library containing hetero-dimeric modified ubiquitin proteins has been established by differently modifying of selected amino acids in each of the monomeric ubiquitin units, the modified dimeric proteins are contacted according to the invention with the ED-B to enable binding of the partners to each other if a binding affinity does exist. These protein libraries may be in the form of a display method library displaying or using any other method presenting the modified proteins in a manner enabling the contact between the modified proteins and the ED-B target protein, wherein said display method is optionally a phage display, ribosomal display, TAT phage display, yeast display, bacterial display or mRNA display method.

Selection of the modified ubiquitin variations with respect to their binding activities to ED-B with a specific binding affinity of Kd in a range of $10^{-7}$-$10^{-12}$M can be performed by means of methods known to those skilled in the art. For this purpose, the ubiquitin variations presented e.g. on the ribosomal complexes can be transiently immobilized to target substance bound e.g. on microtiter plates or can be bound to magnetic particles after binding in solution, respectively. Following separation of non-binding variations the genetic information of variations with binding activity can be specifically eluted in the form of the mRNA by destruction of the ribosomal complex. The elution is preferably carried out with 50 mM EDTA. The mRNA obtained in this manner can be isolated and reverse transcribed into DNA using suitable methods (reverse transcriptase reaction), and the DNA obtained in this manner can be re-amplified.

By means of successive cycles of in vitro transcription/translation, selection, and amplification ubiquitin variations with binding properties for a predetermined hapten or antigen can be enriched.

Characterization of the EDB-Binding Proteins

The further characterization of the ubiquitin variations obtained in this manner can be performed in the form of a soluble protein as detailed above after cloning of the corresponding gene cassette into a suitable expression vector. The appropriate methods are known to those skilled in the art or described in the literature.

Preferably, the step of detection of the proteins having a binding affinity with respect to a predetermined binding partner is followed by a step of isolation and/or enrichment of the detected protein.

Following the expression of the ubiquitin protein modified according to the invention, it can be further purified and enriched by methods known per se. The selected methods depend on several factors known per se to those skilled in the art, for example the expression vector used, the host organism, the intended field of use, the size of the protein and other factors. For simplified purification the protein modified according to the invention can be fused to other peptide sequences having an increased affinity to separation materials. Preferably, such fusions are selected that do not have a detrimental effect on the functionality of the ubiquitin protein or can be separated after the purification due to the introduction of specific protease cleavage sites. Such methods are also known per se to those skilled in the art.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 1 shows a Table listing the occurrence of ED-B in various tumors.

FIG. 2 shows the consensus positions and amino acid substitutions of 16 further sequences which have been found to have surprisingly strong binding affinities to ED-B. The consensus amino acid positions are in the first monomeric binding determining region 2, 4, 6, 62, 63, 64, 65, 66 while the consensus amino acid substitutions are Q2T, F4W, K6H, Q62N, K63F, E64K, S65L, and T66S. As can be taken from FIG. 2, 4 families of sequences could be enriched (consensus sequences, size of the letters correspond to the frequency of occurrence of the amino acids). Positions 85 and 87 are positions in the hetero-dimeric protein; with reference to the second monomer, the corresponding positions are 6 and 8; 141-145 correspond to positions 62-64). TWH NFKLS (SEQ ID NO: 52) depicted in dark-blue colour originates from 1071-C12. Residues marked with red colour belong to one of the said four families of sequences. Residues marked in red have been enriched predominantly (178/457 sequences) and include according to HIT ELISAs the strongest binding molecules. Amino acid sequences that were identified at amino acid positions 141-145 include GWLAP (SEQ ID NO: 53), DWLPA (SEQ ID NO: 54), DSHDV (SEQ ID NO: 55), HYLPK (SEQ ID NO: 56), WHHDF (SEQ ID NO: 57), GWQSP (SEQ ID NO: 58), GWQAP (SEQ ID NO: 59), WSGEF (SEQ ID NO: 60), GFQSP (SEQ ID NO: 61), GWQSP (SEQ ID NO: 62), ATLPN (SEQ ID NO: 63), WHHDM (SEQ ID NO: 64), WPGDM (SEQ ID NO: 65), GRLPK (SEQ ID NO: 66), GYMAP (SEQ ID NO: 67), GYQAP (SEQ ID NO: 68), GYVP (SEQ ID NO: 69), WTRDW (SEQ ID NO: 70), DRLPV (SEQ ID NO: 71), ERLPQ (SEQ ID NO: 72), WHDF (SEQ ID NO: 73), and HHLPT (SEQ ID NO: 74).

FIG. 4A shows a binding affinity of Kd=9.45 µM for the monomer 41B10 (primary selection of SPW28-41B10).

FIG. 4B shows that a binding affinity of a Kd=131 nM for 41B10 combined with a different second monomer resulting in 46H9 (SPW28-41B10).

FIG. 5A is a schematic drawing of a modified ubiquitin based ED-B binding-effector-fusion protein; in green (structure on top)—effector, e.g. a cytokine, preferably TNF-alpha: red regions on effector; brown: light brown: structure of the modified ubiquitin monomers (AFFILIN®).

FIG. 5B shows that the modified ubiquitin effector conjugate 5E1-TNF-conjugate has pro-apoptotic activity (as measured in an L929 apoptosis assay).

FIG. 5C shows high affinity binding of 1H4-TNFalpha-fusion to ED-B (Kd=15.1 nM) (closed circles connected by a fitted line). The binding to BSA is plotted as a control (closed circles not connected by a line).

FIGS. 6A-6E show the affinity and activity of a modified ubiquitin based ED-B binding hetero-dimer molecule fused to a cytokine, for example, TNFalpha.

Apotosis inducing activity of modified ubiquitin based ED-B binding cytokine fusion: $EC_{50}$ 0.78±0.24 pM Apoptosis inducing activity of free cytokine: $EC_{50}$ 3.14±3.59 pM FIG. 6A shows the high affinity of modified ubiquitin based ED-B binding hetero-dimer 24H12 (Kd 50.7 nM).

FIG. 6B shows the increased affinity of modified ubiquitin based ED-B binding heterodimer 24H12 genetically fused to cytokine TNFalpha to result in a multimerisation of the hetero-dimer 24H12 (Kd=5.6 nM).

FIG. 6C shows an analysis of exemplary candidates from a hetero-dimeric modified ubiquitin library selection, for example hetero-dimer clones 9E12, 22D1, 24H12, and 41B10. The Kd ELISA values were increased for the target ED-B compared to cytosolic fibronectin used as control, confirming a specific binding to the target.

FIG. 6D shows results of an analysis of the modified hetero-dimeric ubiquitin molecule 9E12 via label-free interaction assays using BIACORE®. Different concentrations of the hetero-dimeric ubiquitin variants were analyzed (see figure legend: 0-15 microM of 9E12) for binding to ED-B immobilized on a chip (BIACORE®) to analyze the interaction between the hetero-dimeric variant 9E12 and ED-B. A Kd could not be determined from analyzing the association and dissociation curves.

FIG. 6E shows results of an analysis of the modified hetero-dimeric ubiquitin molecule 41B10 via label-free interaction assays using BIACORE®. Different concentrations of the hetero-dimeric ubiquitin variants were analyzed (see figure legend: 0-15 microM of 41B10) for binding to ED-B immobilized on a chip (BIACORE®) to analyze the interaction between the hetero-dimeric variant 41B10 and ED-B. Analyzing the association and dissociation curves resulted in a Kd of 623 nM ($623 \times 10^{-9}$ M, $6.2 \times 10^{-7}$ M).

FIG. 3 shows different combinations of monomers resulting in modified ubiquitin-heterodimers. Hetero-dimeric variants 46-A5, 50-G11 and 46-H4 have all the same first (front) modified monomer with BDR1 (labeled with the letter "a" in the figure), but a second (rear) ubiquitin monomer modified in different positions with BDR2. Variants 52-D10 and 52-B3 have a different first (front) modified monomer compared to 46-H9 with BDR1, but the same second (rear) ubiquitin monomer with BDR2 (labeled with the letter "e").

The modified ubiquitin hetero-dimers have the following sequences: 46-H4: SEQ ID NO: 25, 45-H9: SEQ ID NO: 26, 46-A5: SEQ ID NO: 27, 50-G11: SEQ ID NO: 28, 52-B3: SEQ ID NO: 29, 52-D10: SEQ ID NO: 30

The above described sequences were modified in the course of the experiments by adding a His-Tag with the sequence LEHHHHHH (SEQ ID NO: 31).

Figure 3:
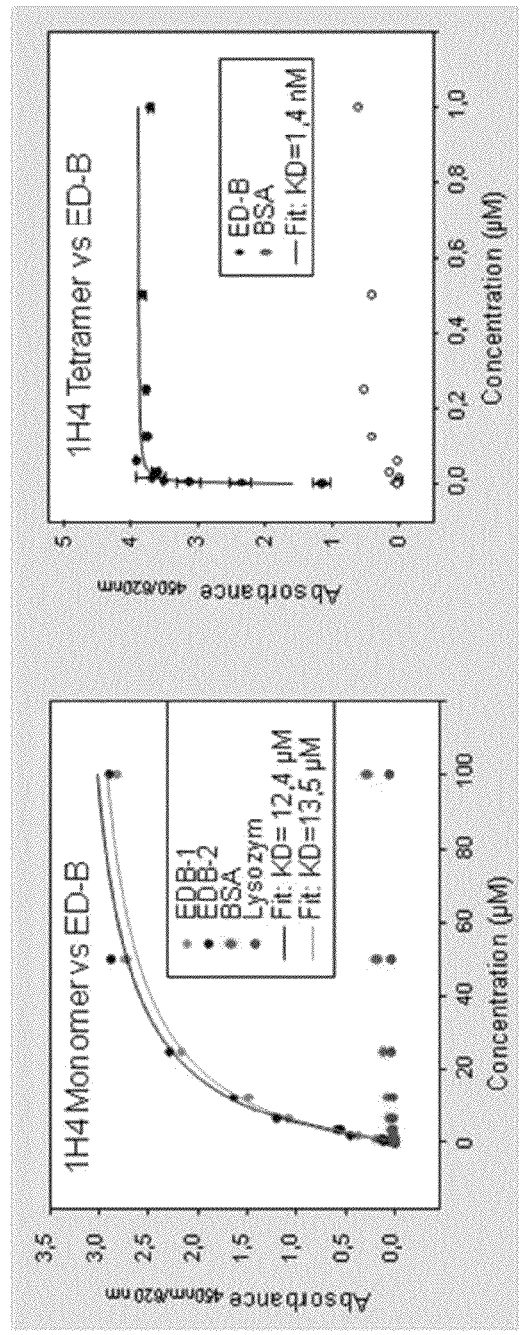
FIG. 3 shows that tetramerization leads to an increase in affinity. The table shows the Kd values of modified ubiquitin monomers compared to tetramers consisting of modified ubiquitin monomers. Shown are ubiquitin variants 5E1 and 1H4 as examples. The ED-B binding is compared to binding to c-FN (cellular fibronectin). The figures demonstrate the significant higher affinity in binding of the tetrameric variant (for example, 56 nM for 5E1 or 1.4 nM for 1H4) to the target ED-B compared to the monomer (4.51 microM for 5E1 or 9.98 microM for 1H4).
Figure 4A:
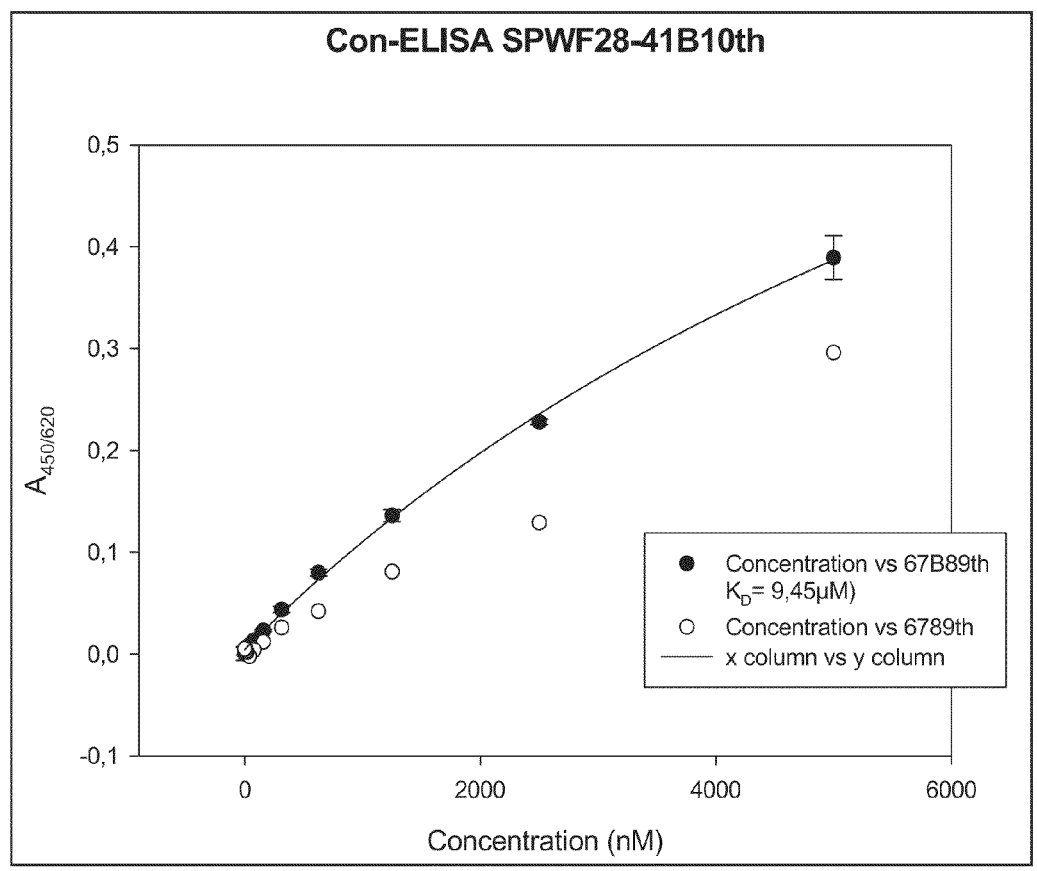
FIGS. 4A and 4B show that the recombination of a front (first) modified ubiquitin monomer (having a BDR1; clone 41B10) with a different modified rear (second) ubiquitin monomer (having a BDR2) to generate a hetero-dimer results in a significant increase of affinity as well as specificity. The modified ubiquitin molecules are analyzed via BIACORE®, fluorescence anisotropy, binding on cells and tissue sections. Shown are concentration dependent ELISAs (conc.-ELISA) of the binding of several variants to human ED-B.
Figure 4B:
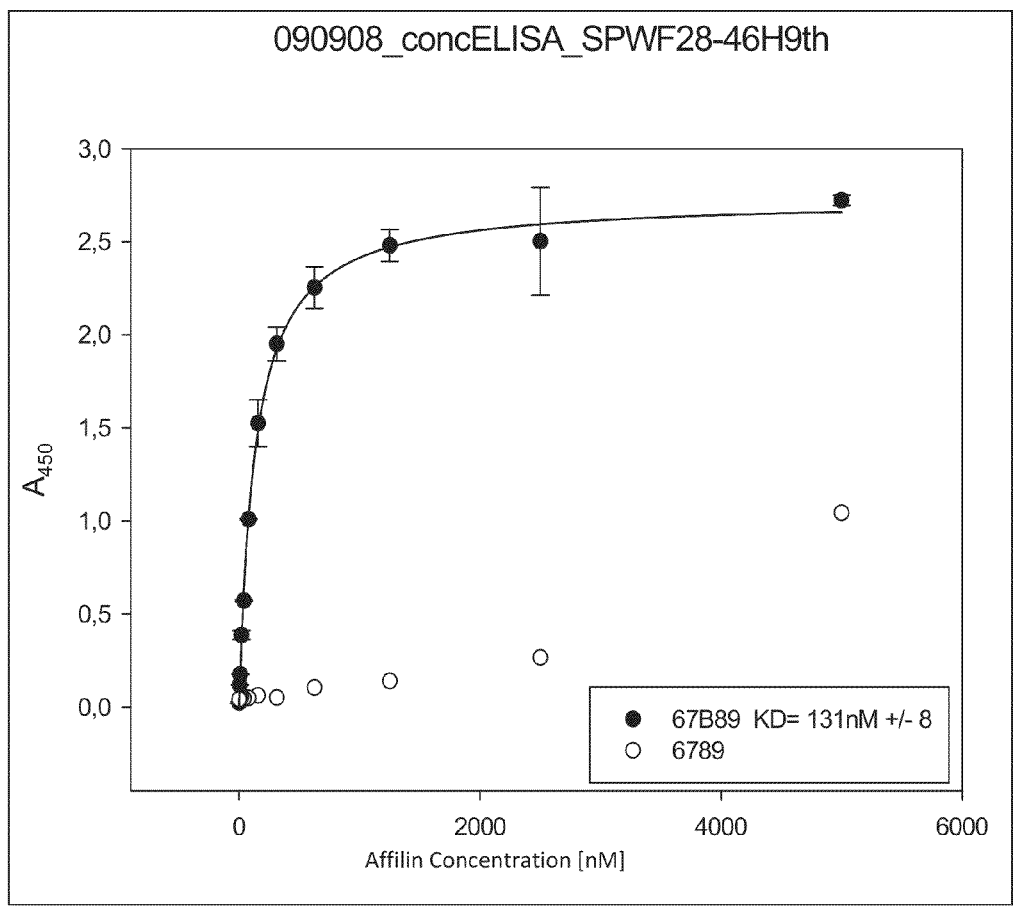
Figure 5A:
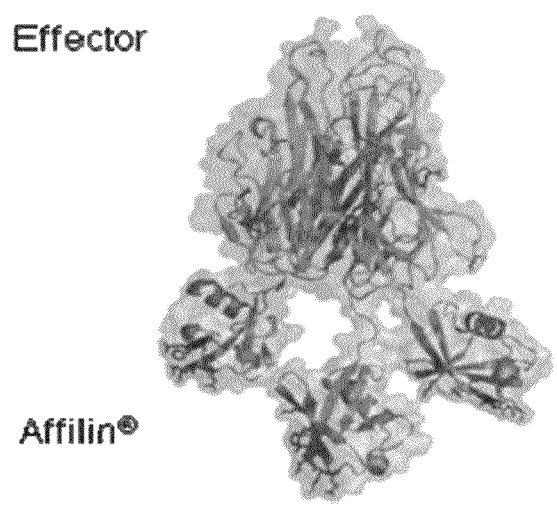
FIGS. 5A-5C show modified ubiquitin-based ED-B binding with specific variants fused to a cytokine (for example, TNFalpha). The TNFalpha fusion proteins trimerize the modified ubiquitin monomer and are biologically active molecules.
Figure 5B:
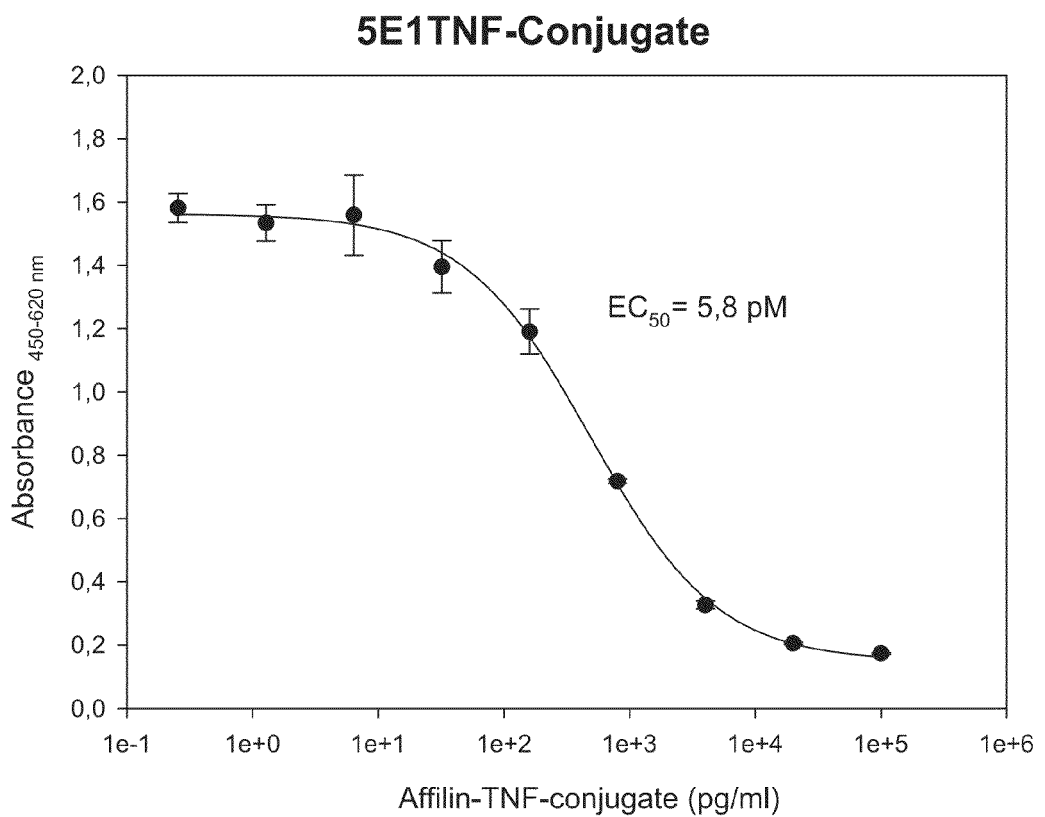
Figure 5C:
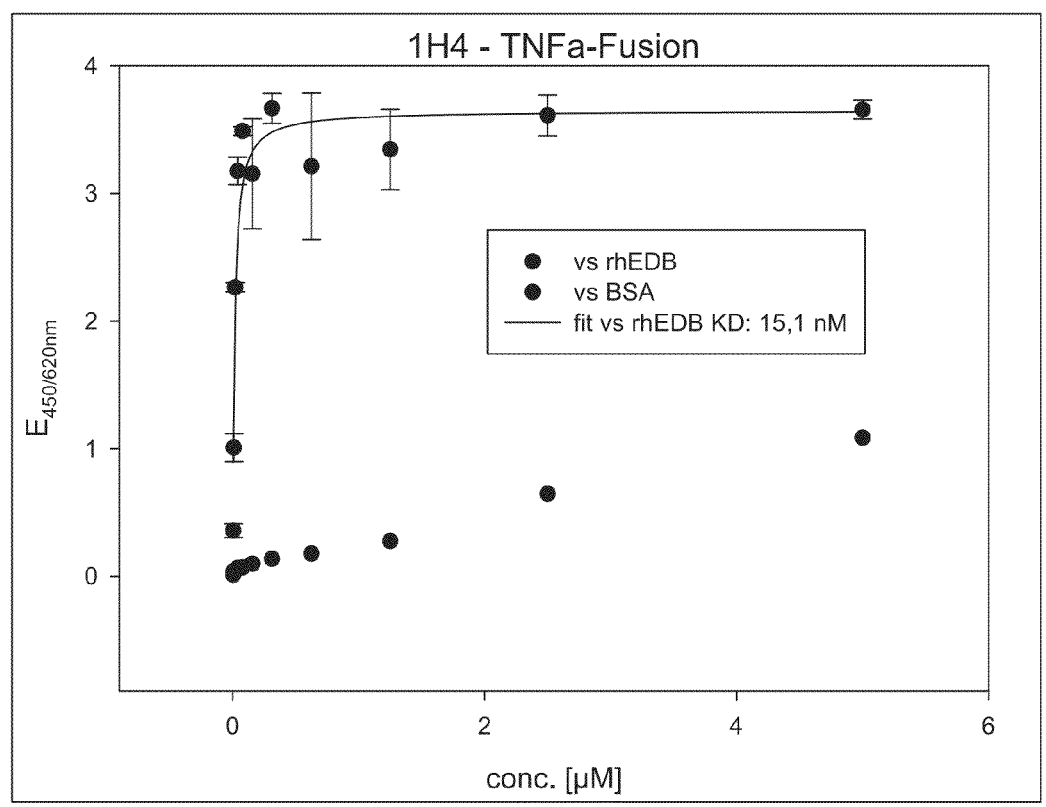
Figure 6A:
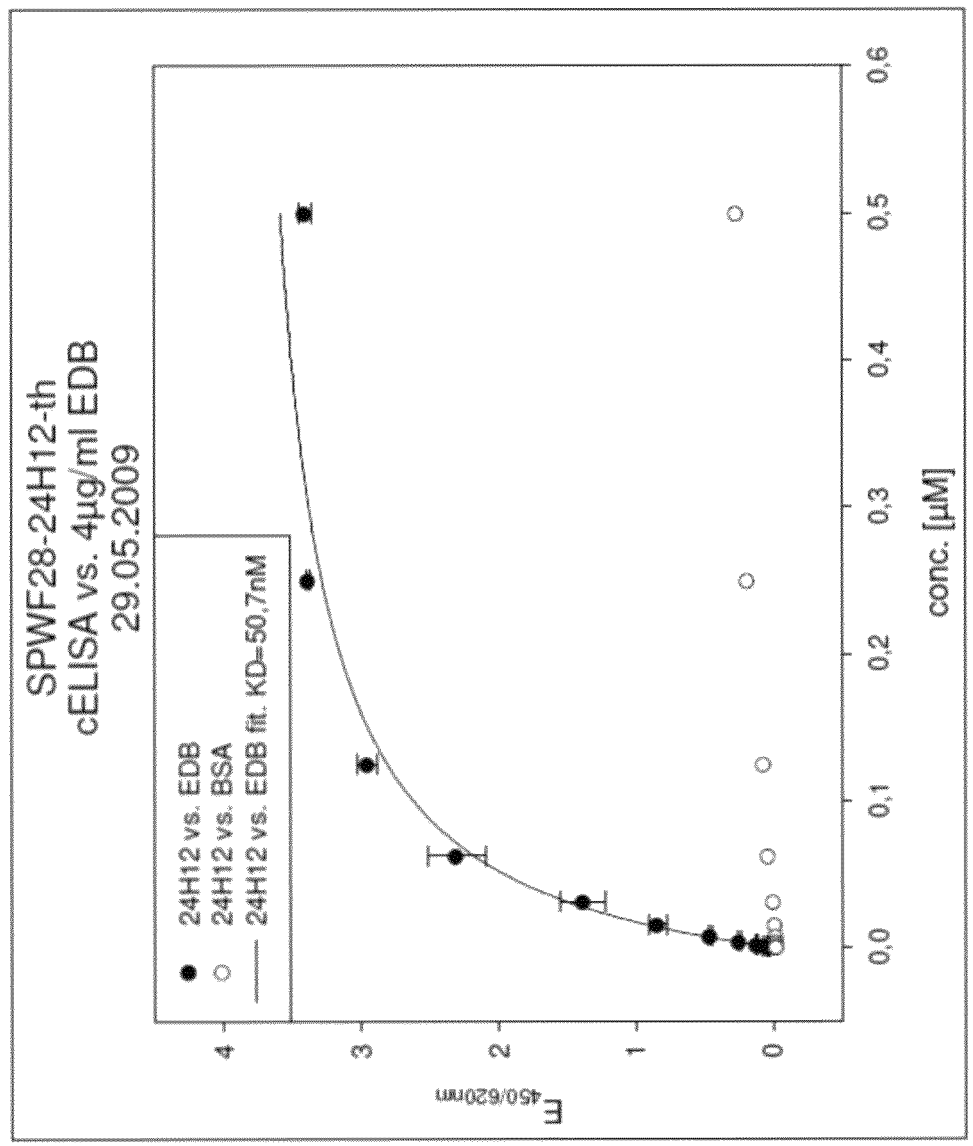
Figure 6B:
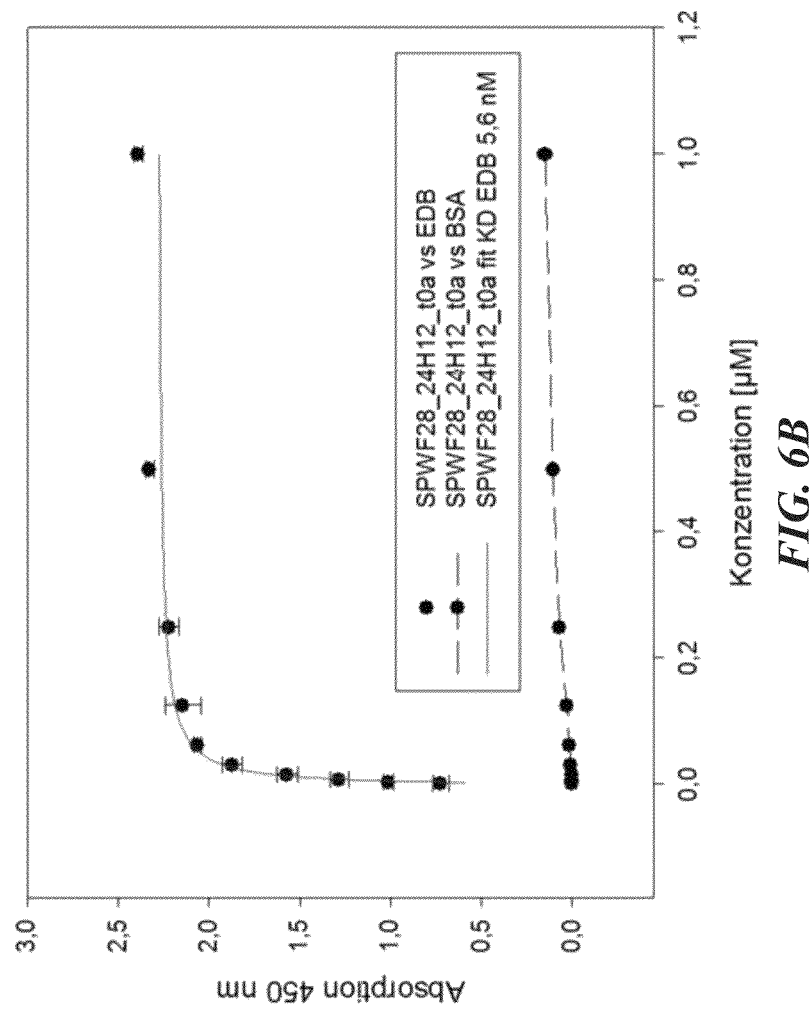
Figure 6D:
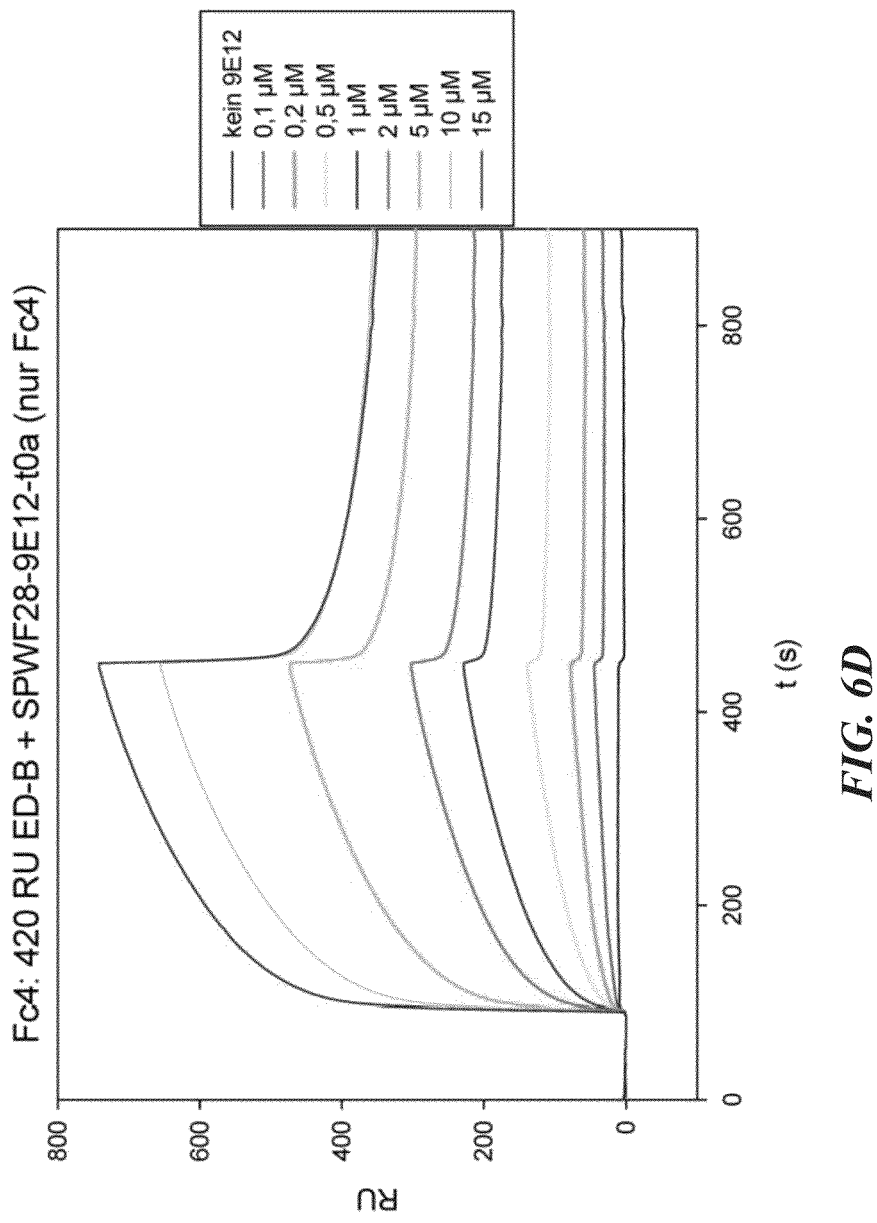
Figure 6E:
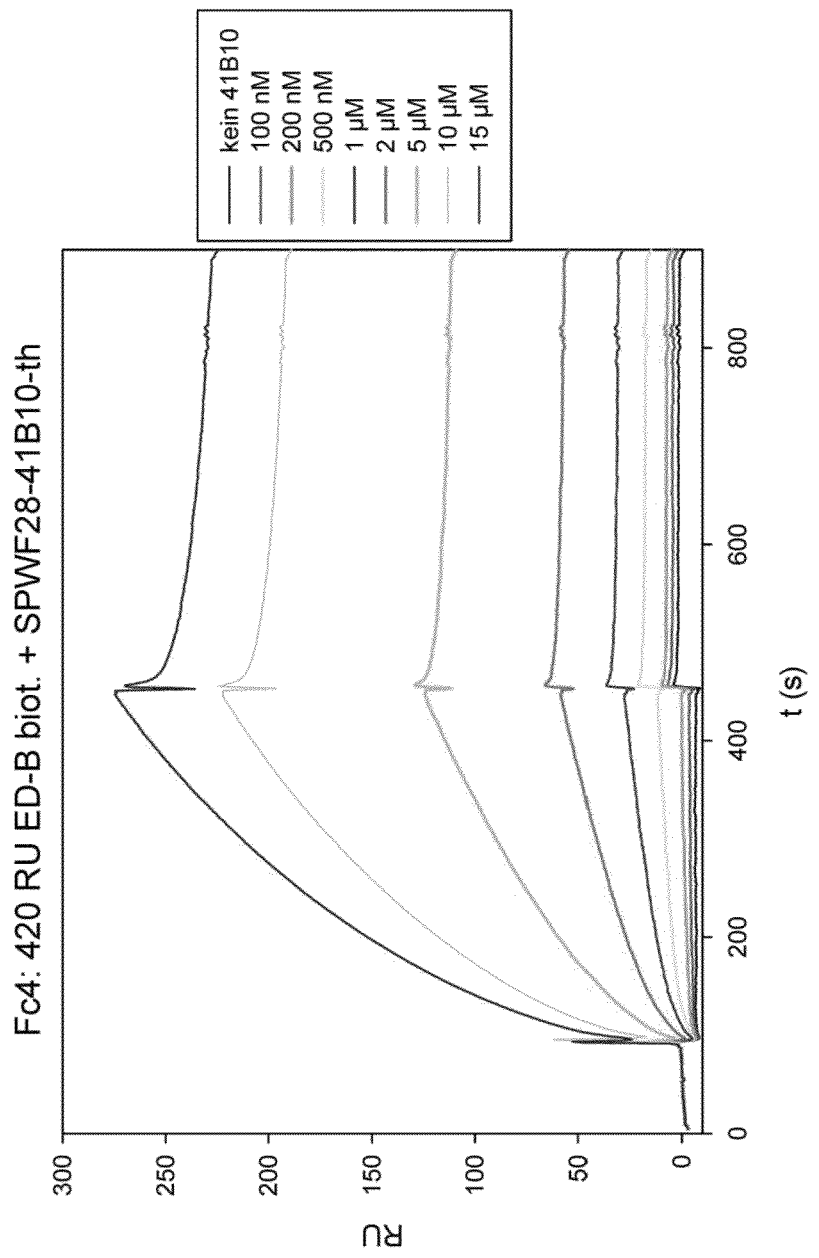
Figure 7:
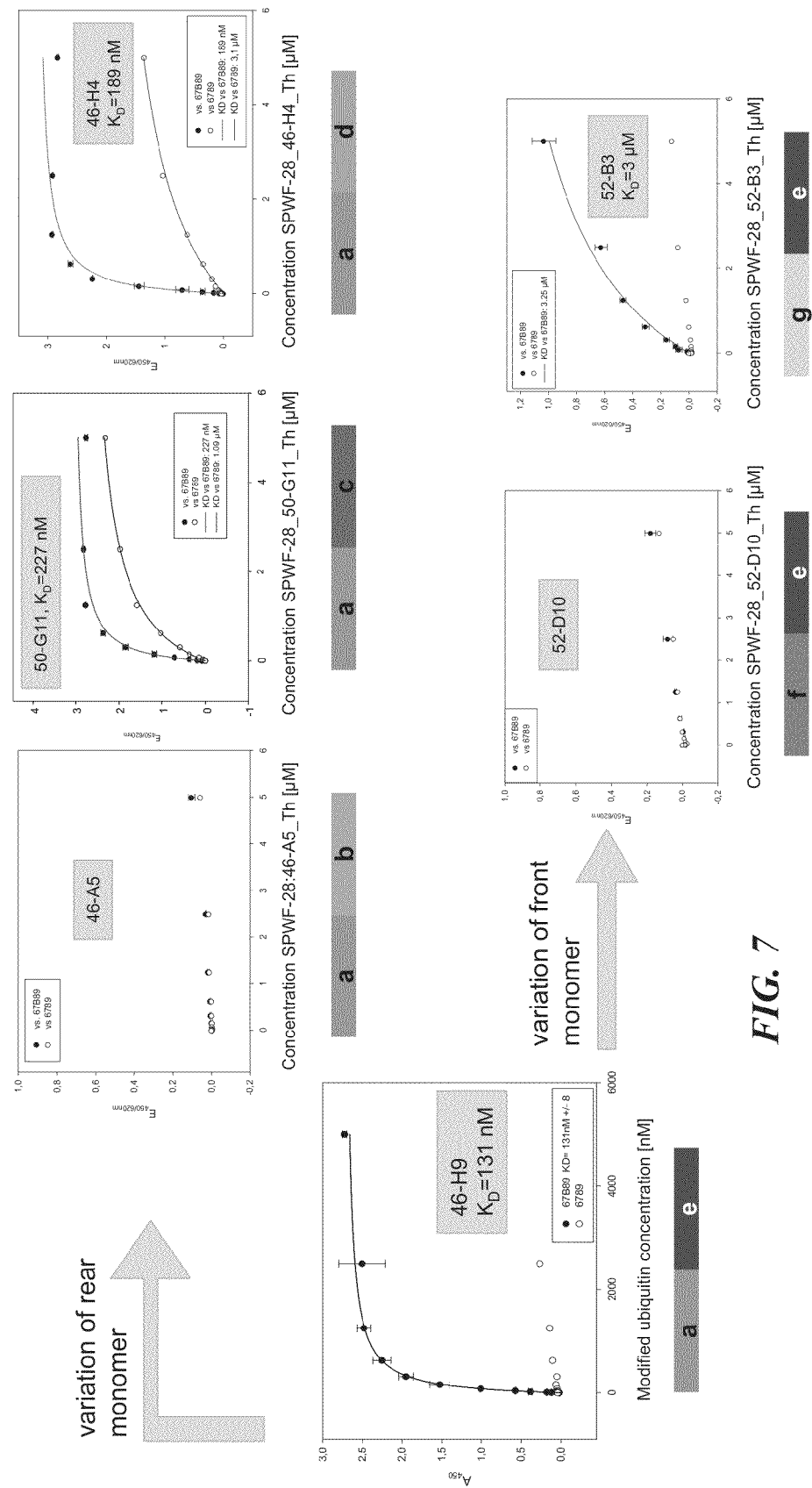
FIG. 7 shows the contribution of different modified ubiquitin based variants to binding affinity and specificity. The different variants share common sequence modules which are marked with lower case letters. The variants were analyzed with respect to their ED-B binding.

As can be seen from FIG. 7, 46-H4 has an excellent binding affinity to ED-B (Kd=189 nM); 46-A5 and 52-D10 have no binding activity while other modified ubiquitin proteins provide a minor binding activity compared 46-H4 to ED-B. Thus it can be concluded that both monomers in a hetero-dimeric variant are required for a high affinity binding to a target; both monomers show a monovalent binding to the target.

Figure 8:
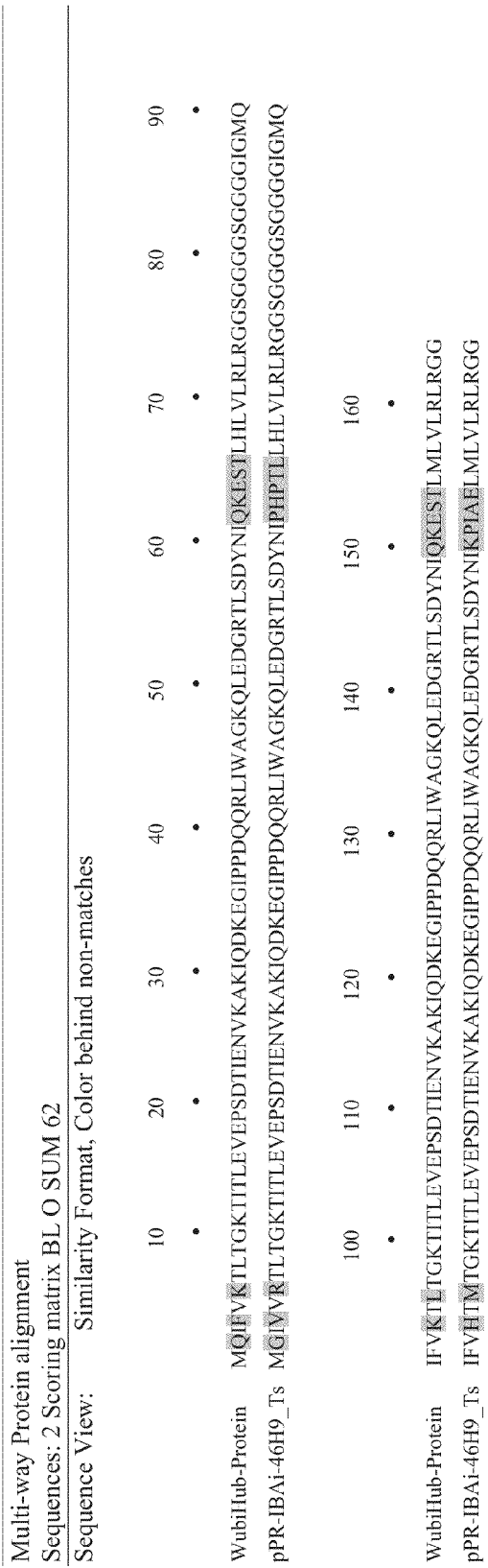

The modified ubiquitin hetero-dimer with high ED-B binding activity named 46 H9 is identified by the following amino acid replacements in both binding domain region in the two monomers as compared to wild type ubiquitin monomers:
in the first module (BDR1) (a) □2G, F4V, K6R, Q62P, K63H, E64A, S65T, T66L
in the second module (BDR2) (e) K6H, L8M, Q62K, K63P, E64I, S65A, T66E
50G11
in the first module (46H9)(a) □2G, F4V, K6R, Q62P, K63H, E64P, S65T, T66L
in the second module (c) K6M L8R, Q62M, K63N, E64A, S65R, T66L
46H4
in the first module (46H9)(a) □2G, F4V, K6R, Q62P, K63H, E64P, S65T, T66L
in the second module (d) K6G, LBW, Q62T, K63Q, E64Q, S65T, T66R
52B3
in the first module (g) □2R, F4P, K6Y, Q62P, K63P, E64F, S65A, T66R
in the second module (46H9) K6H, L8M, Q62K, K63P, E64I, S65A, T66E
52D10 (non-ED-B binder)
in the first module Q2V, F4C, K6R, Q62T, K63A, E64P, S65G, T66D
in the second module (46H9) (e) K6H, L8M, Q62K, K63P, E64I, S65A, T66E
46A5 (non-ED-B binder)
in the first module (46H9)(a) □2G, F4V, K6R, Q62P, K63H, E64P, S65T, T66L
in the second module (b) K6L, L8M, Q62L, K63A, E64F, S65A, FIG. 8 shows a sequence alignment. Line 1: Two monomers of the wild type ubiquitin protein (1st line) are linked with a 12-amino acid linker SGGGGSGGGGIG (SEQ ID NO: 32) starting at Position 77 and ending at Position 88; the second monomer with BDR2 starts at position 89 with a Methionine. This dimeric wild-type ubiquitin protein is aligned with the modified ubiquitin hetero-dimeric variant 46-H9 (2nd line) with different modifications in the first and in the second monomer resulting in two BDR's. Both BDRs act together in the binding of the target due to a monovalent binding to the target. WubiHub-Protein corresponds to SEQ ID NO: 75 and pPR-IBAi-46H9 Ts corresponds to SEQ ID NO: 76.

FIG. 9 shows a sequence alignment of modified ubiquitin hetero-dimeric variant 1041-D11 (1st line; SEQ ID NO: 77) to "Ub2_TsX9" (ubiquitin modified in position 45 in both monomers to Tryptophan, showing the linker GIG between the two monomers at (position 77 to 79; the second monomer starts with a Methionine at Position 80), and an exchange from Glycine to Alanine at the last c-terminal amino acids of the 2nd monomer; SEQ ID NO: 78). The third line shows "Ubi-Dimer wt", the wildtype ubiquitin as dimer (SEQ ID NO: 79); showing no linker alignment (thus, the second monomer starts at position 77 with a Methionine). The 4th line shows the "Ubi-Monomer wt" which is the human wild type ubiquitin (SEQ ID NO: 80).

Figure 10:
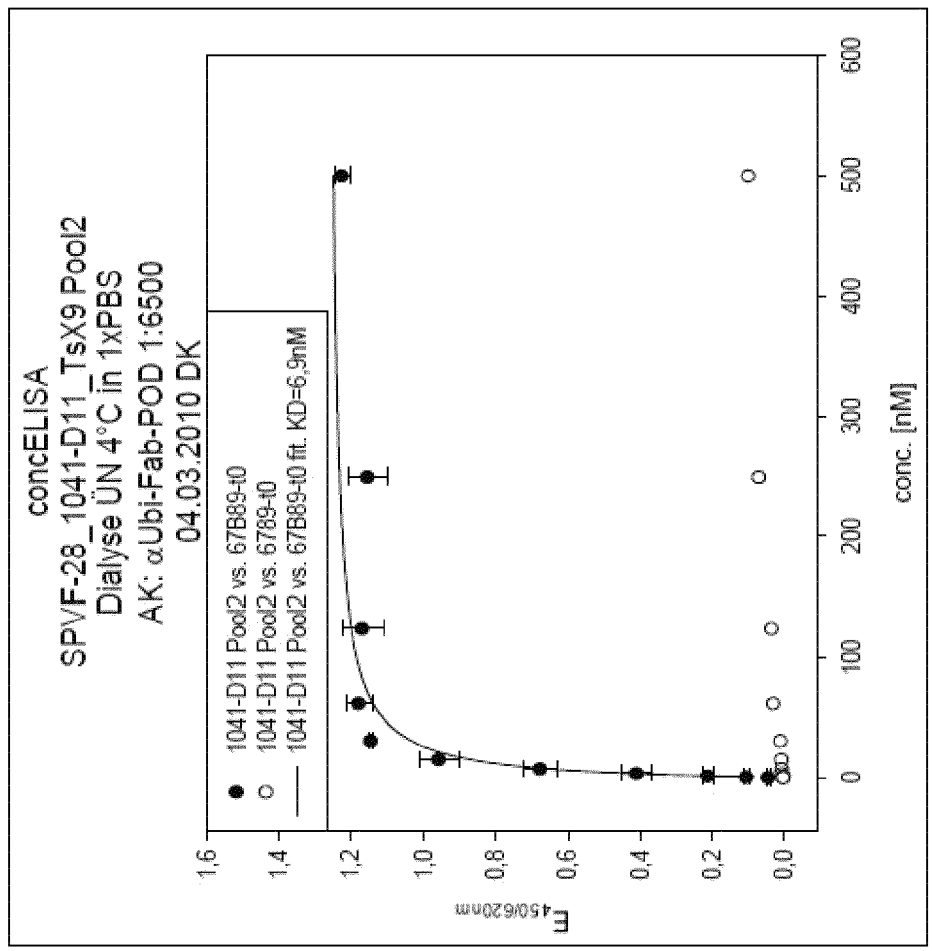

FIG. 10 shows a concentration dependent ELISA of the binding of the hetero-dimeric ubiquitin variant 1041-D11 to human ED-B. Variant 1041-D11 shows very high affinity binding to ED-B (Kd=6.9 nM=$6.9 \times 10^{-9}$ M). The closed dots show the affinity of the binding of hetero-dimeric ubiquitin variant 1041-D11 to an ED-B containing fibronectin fragment (referred to as 67B8940) compared to no binding of this variant to negative control (referred to as 678940) (open circles).

Figure 11:
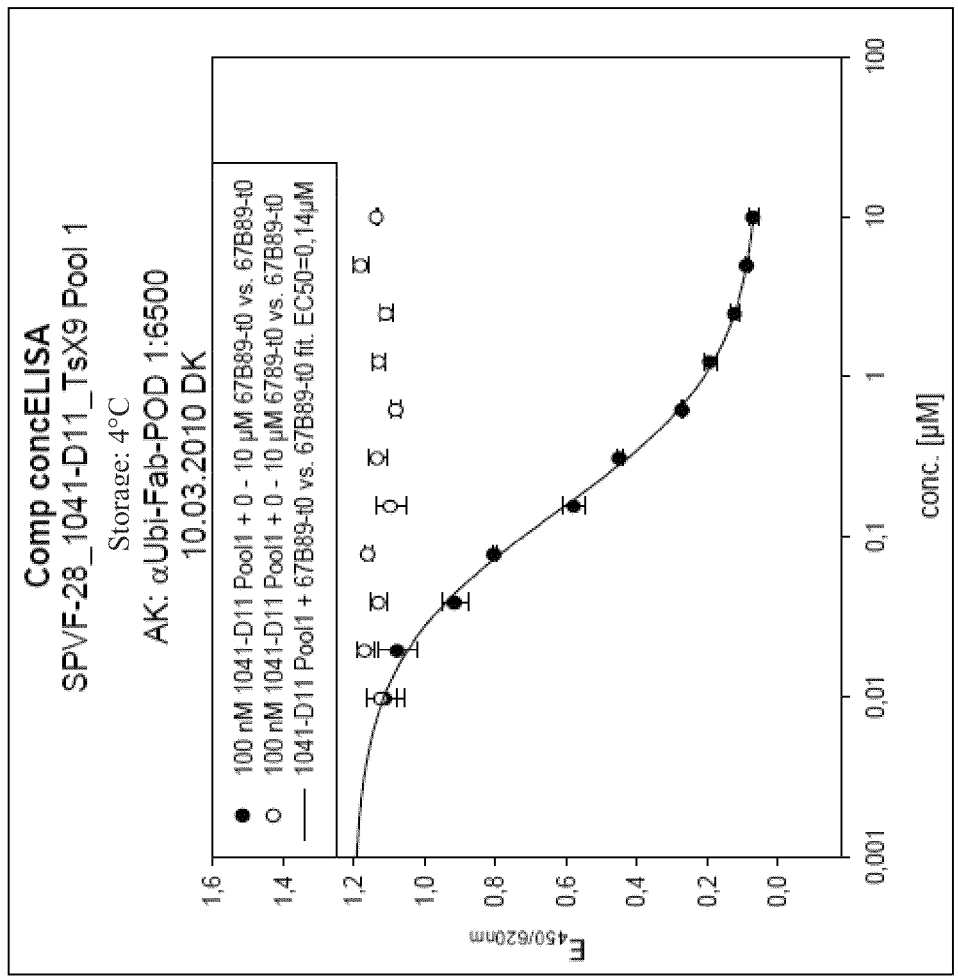

FIG. 11 shows competitive concentration dependent ELISAs of the binding of hetero-dimeric ubiquitin variant 1041-D11 to immobilized ED-B containing fibronectin fragment (67B89) in the presence of increasing amounts of free target. Hetero-dimeric ubiquitin variant 1041-D11 shows a very high affinity binding to ED-B (IC50=140 nM).

Figure 12:
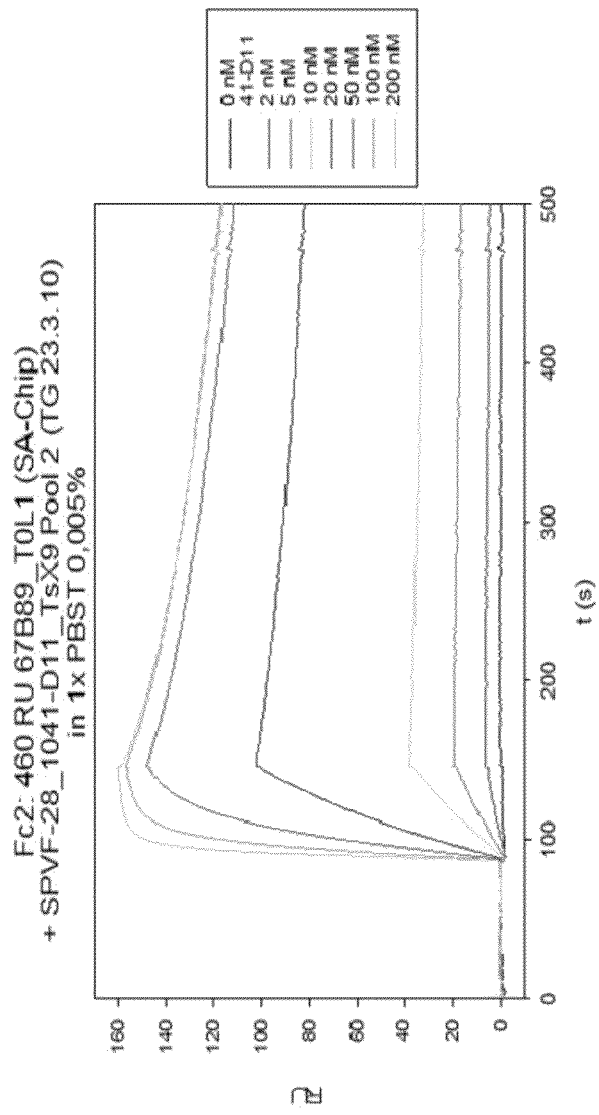

FIG. 12 shows a result of an analysis of the modified hetero-dimeric ubiquitin molecule 1041-D11 in label-free interaction assays using BIACORE®. Different concentrations of the hetero-dimeric ubiquitin variant were analyzed (see figure legend: 0-200 nM of 1041-D11) for binding to an ED-B containing fibronectin fragment (referred to as 67B89) immobilized on a SA-chip (BIACORE®). Analyzing the association and dissociation curves resulted in a Kd of 1 nM ($1 \times 10^{-9}$ M) and a $k_{off}$ rate of $7.7 \times 10^{-4}$ s$^{-1}$ which indicates a long half time of an complex of 1041-D11 and ED-B.

Figure 13:
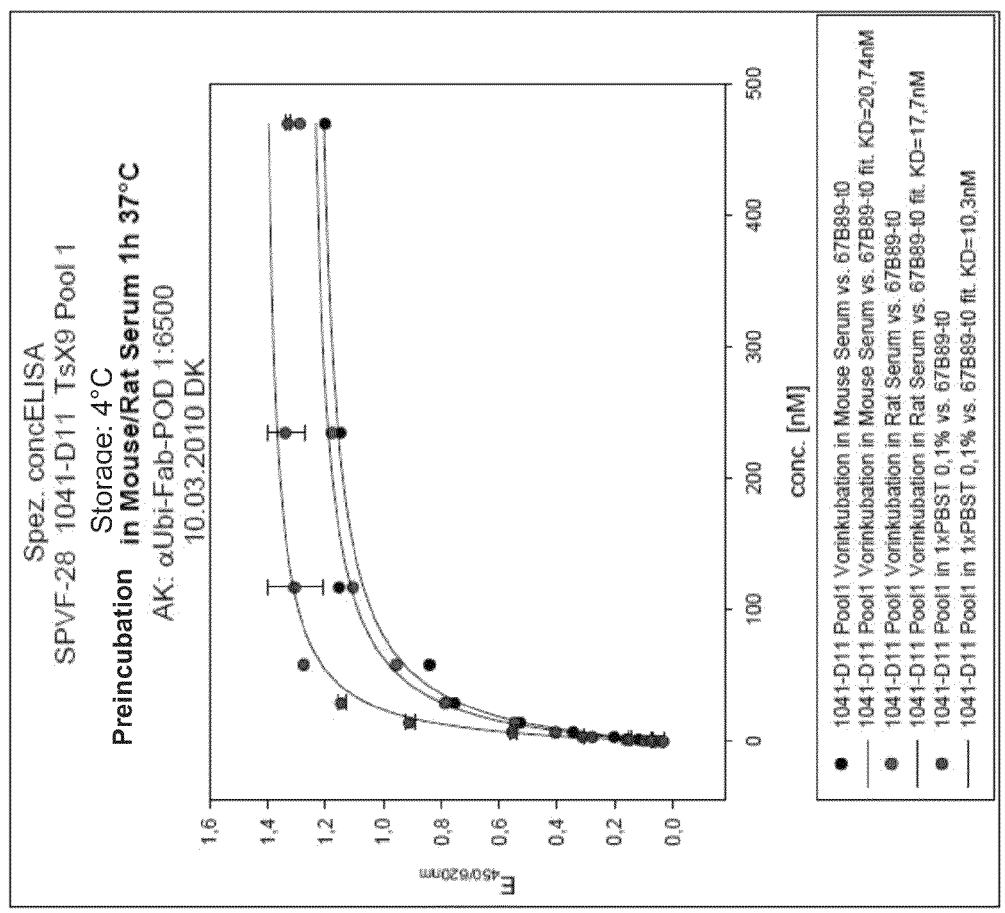

FIG. 13 shows the binding of hetero-dimeric ubiquitin variant 1041-D11 to ED-B in a concentration dependent ELISA simultaneously analyzing the serum-stability of binding activity. Shown are different conditions, such as pre-incubation for 1 h at 37° C. of the variant in mouse or rat serum or in PBST as control. The Kd-values are all between 10 and 20 nM. Thus, it can be concluded that the binding of the hetero-dimer 1041-D11 to ED-B is not significantly influenced by blood serum.

Figure 14A:
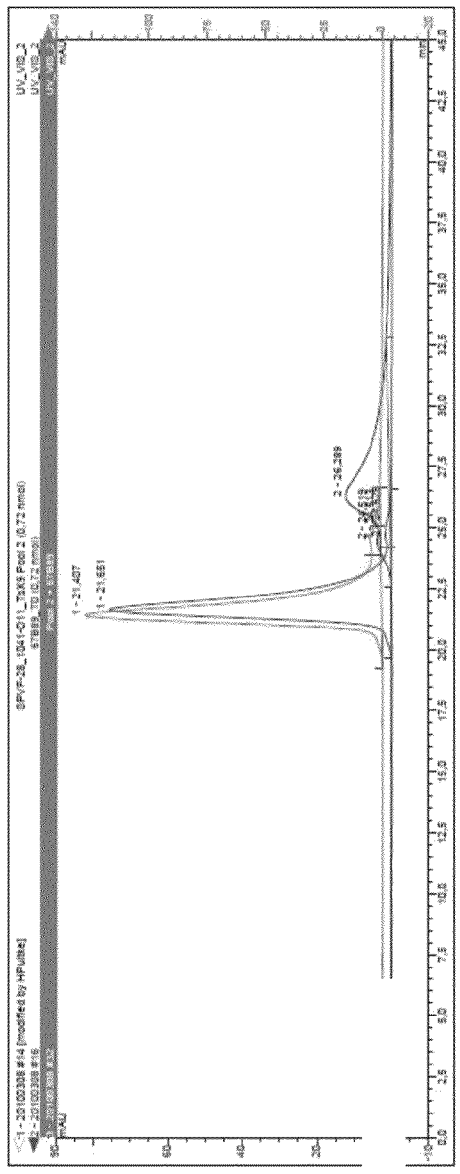
Figure 14B:
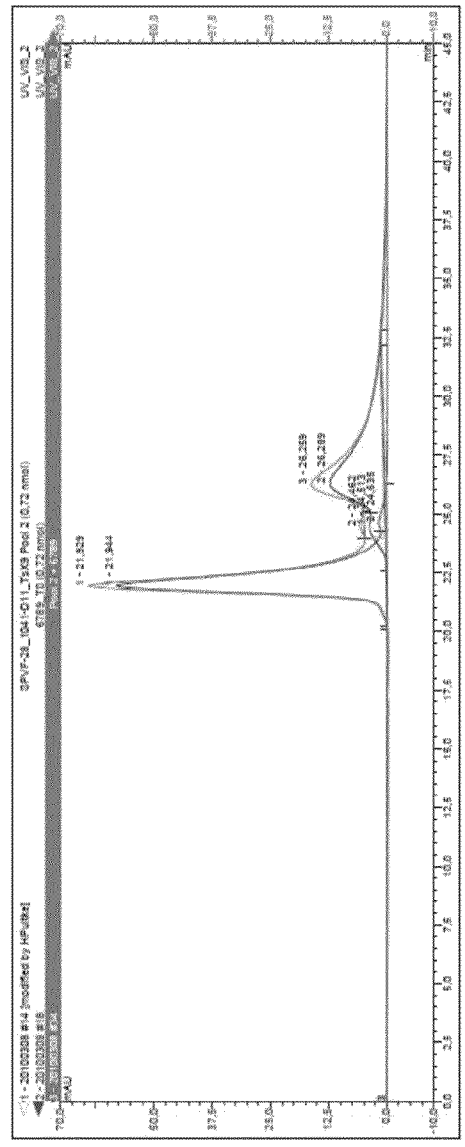

FIGS. 14A and 14B show an analysis of the complex-formation of hetero-dimeric ubiquitin variant 1041-D11 with fibronectin fragments by SE-HPLC.

FIG. 14A shows complex formation of 1041-D11 with ED-B. Three HPLC runs are overlaid: the blue peak with a retention time of 21.651 min originates from pure 1041-D11; the black peak with a retention time of 26.289 min represents the fibronectin fragment 67B89; a mixture of 1041-D11 and 67B89 results in the red peak with a retention time of 21.407 min after SE-HPLC. The shift of the 1041-D11 peak to a lower retention time as well as the disappearance of the 67B89 peak indicates formation of a complex of 1041-D11 and soluble ED-B.

FIG. 14B shows the overlay of three SE-HPLC runs of 1041-D11 (blue, 21.944 min), fibronectin fragment 6789 without ED-B (black, 26.289 min) and a mixture of 1041-D11 and 6789 (red line with peaks at 21.929 min and 26.289 min). Almost no shift of the 1041-D11 peak is observed. This fact together with a lack of disappearance of the 6789 peak indicates no significant binding of the ED-B free fibronectin fragment 6789.

FIGS. 15A-15D show the binding of hetero-dimeric ubiquitin variant 1041-D11 to cell culture cells.

Figure 15A:
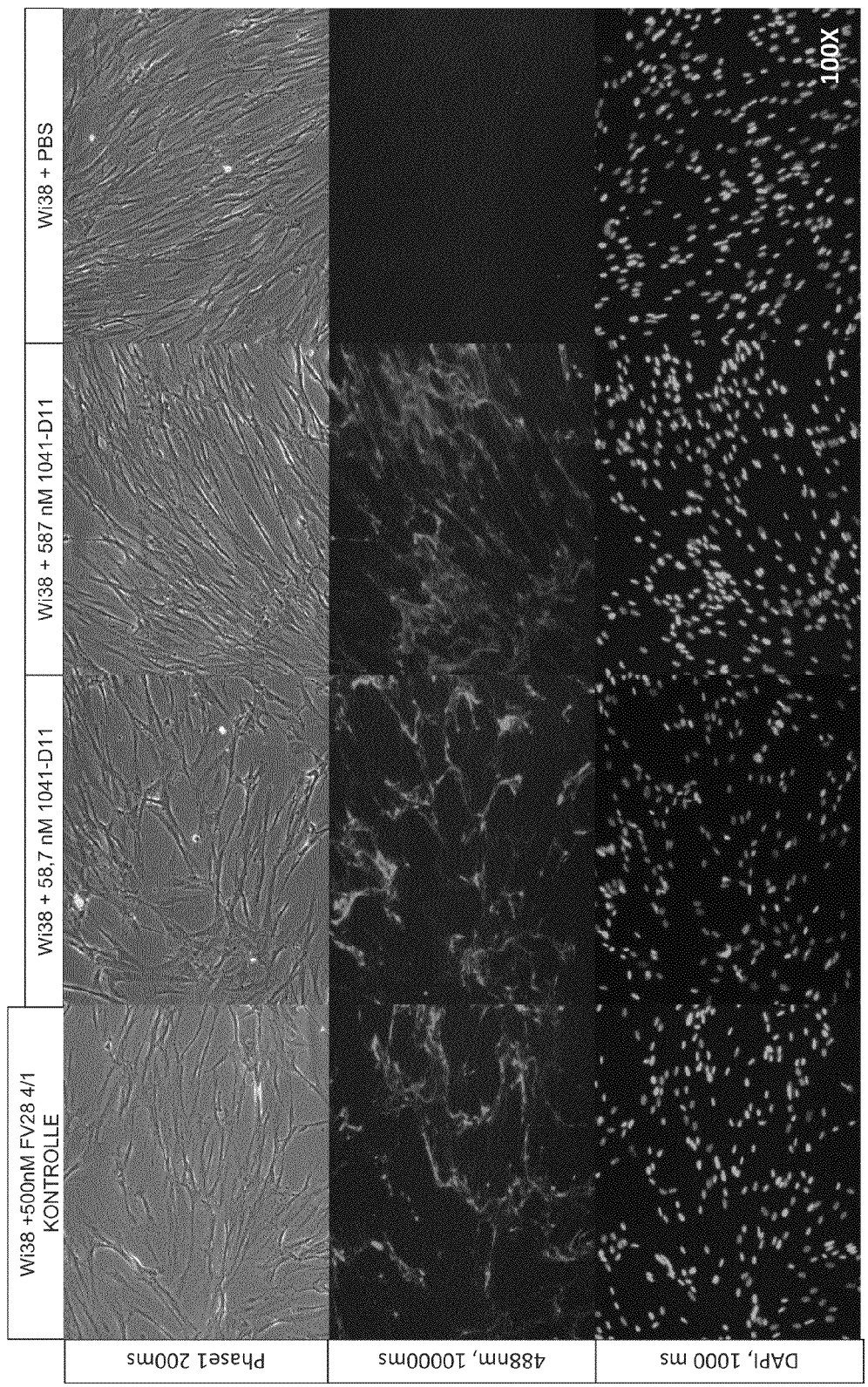

FIG. 15A shows binding of the hetero-dimeric ubiquitin variant 1041-D11 on human fetal lung fibroblast cells (Wi38) which were fixed. The first column in FIG. 15 shows the control using anti-ED-B antibodies, the second column shows the incubation of the variant at a protein concentration of 58.7 nM, the third column a ten-fold higher concentration of 1041-D11 protein (587 nM), the fourth column is a negative control with PBS. In the first row, human Wi38 fibroblast cells are shown in phase contrast; the second row shows the immunofluorescence and the third row a DAPI staining the nuclei. It can be concluded that the variant 1041-D11 binds to Wi38 with high specificity to ED-B containing extracellular matrix. A control using NHDF cells which express low level of EDB was performed (data not shown). The variants do not bind to those cells.

Figure 15B:
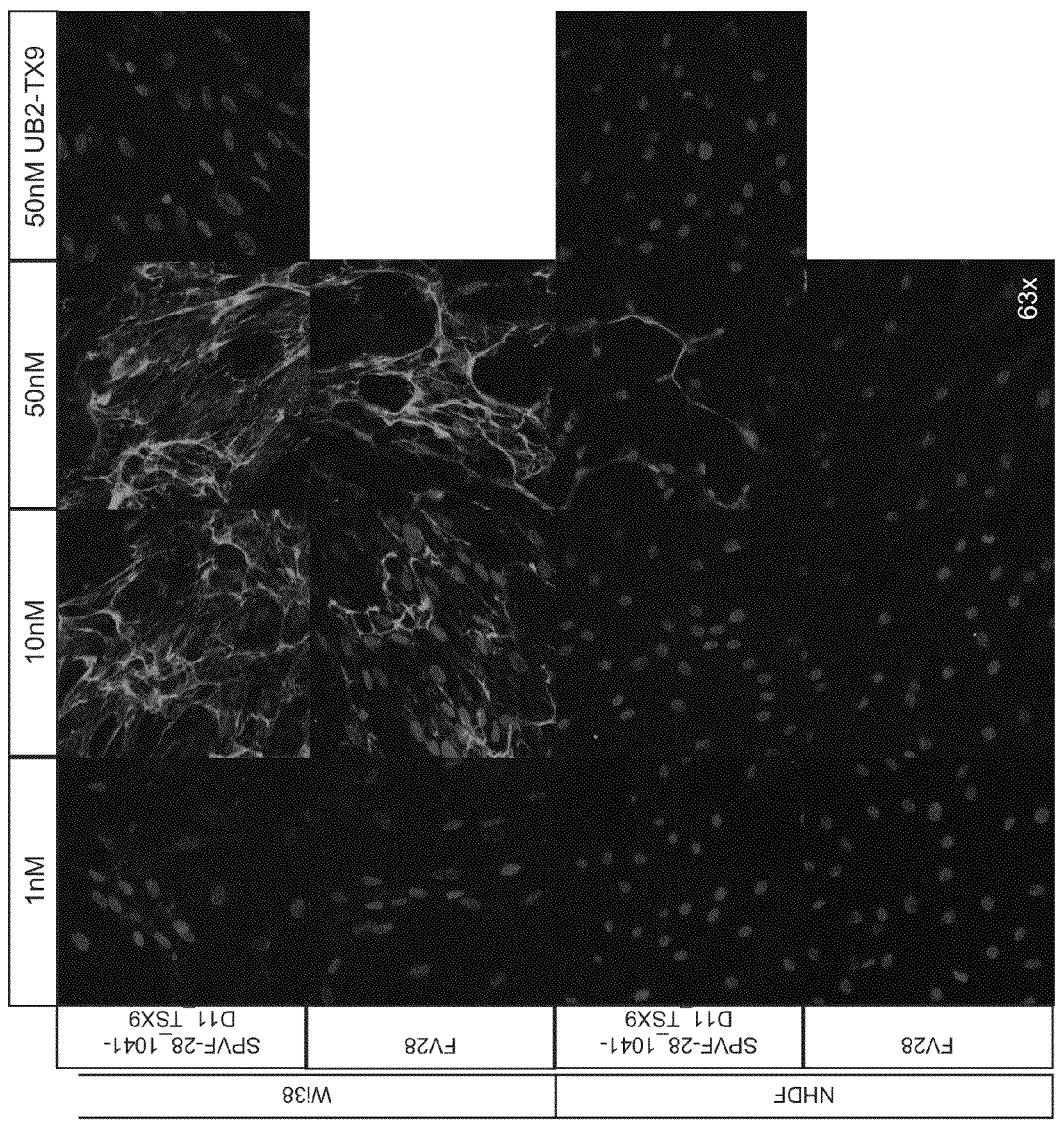

FIG. 15B shows the binding on vital human fetal lung fibroblast cells (Wi38). The negative control cells type NHDF are primary normal fibroblast cells, which express low levels of EDB-fibronectin. The first and third line shows the variant at different protein concentration and the negative control. The second and fourth line shows the incubation of the control using EDB antibodies. The first 2 lines show the variant and positive control on Wi38-cell line. The third and fourth line shows the incubation of NHDF-cells. It can be seen that the variant 1041-D11 binds to Wi38 with high specificity to ED-B containing extracellular matrix.

Figure 15C:
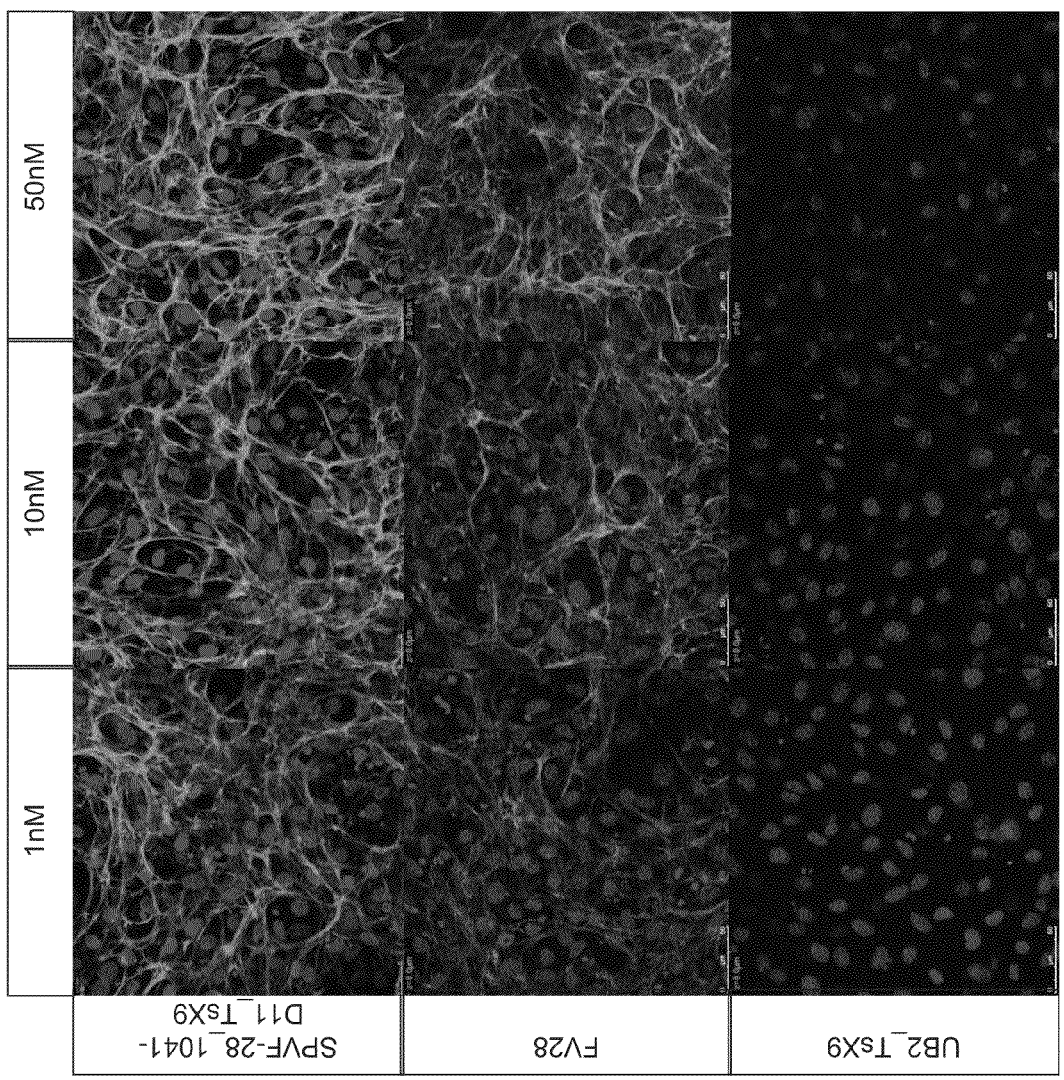

FIG. 15C shows the binding on fixed murine Balb 3T3-cells. Three different protein concentrations (1, 10, 50 nM) of the variant were tested. The first rows shows the variant (SPVF-28-1041-411-TsX9) on cells, the second row shows the positive control (Fv28-EDB-Antibodies), the third row shows the incubation with the negative control (UB2 TsS9; unmodified ubiquitin corresponding to SEQ ID NO:1). It can be seen that the variant 1041-D11 binds to murine Balb 3T3 cells with high specificity to ED-B containing extracellular matrix.

FIG. 15D shows the binding on fixed murine ST-2-cells. Three different protein concentrations (1, 10, 50 nM) of the variant were tested. The first rows shows the variant (SPVF-28-1041-411-TsX9) on cells, the second row shows the positive control (Fv28-EDB-Antibodies), the third row shows the incubation with the negative control (UB2_TsS9; unmodified ubiquitin corresponding to SEQ ID NO:1). It can be seen that the hetero-dimeric ubiquitin variant 1041-D11 binds to murine Balb ST-2 cells with high specificity to ED-B containing extracellular matrix.

Figure 16A:
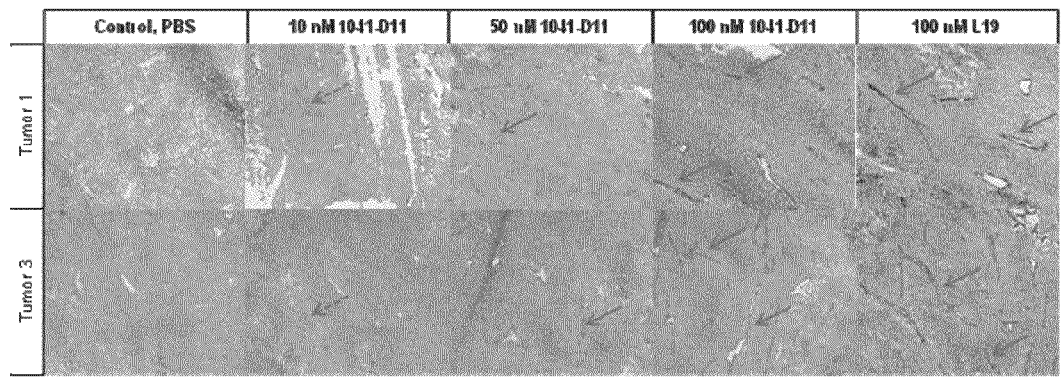

FIG. 16A shows the specificity of hetero-dimeric ubiquitin variant 1041-D11 to the target in mammalian tissue sections. F9 tumor tissues from seven samples were evaluated. Immunohistochemistry with different concentrations between 10 nM and 100 nM of hetero-dimeric ubiquitin variant 1041-D11 resulted in ED-B specific vascular staining on F9 tumors from mice. ED-B is a highly specific marker for tumor vasculature. The target protein ED-B is located on the abluminal side of the vessels. Variant 1041-D11 specifically decorates the vasculature in tissue sections from F9 tumors. The obtained results are comparable to the antibody fragment L19. In addition, 48 tissues were tested; no unspecific staining in any out of 48 tissues in FDA relevant panel was observed.

Figure 16B:
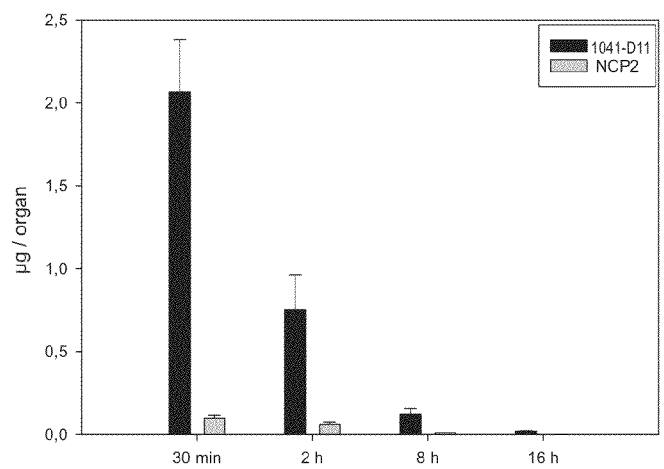

FIG. 16B shows the accumulation of 1041-D11 in tumor tissue in comparison to wild type ubiquitin (in the figure, Ub2 (NCP2). F9 tumor tissues were analyzed for the presence of 1041-D11 and wildtype ubiquitin at different time points between 30 min and 16 h. The highest accumulation of 1041-D11 in tumor tissue is observed 30 min and 16 h after administration whereas the accumulation of wildtype ubiquitin in F9 tumor tissues is low. The variant is enriched in tumors expressing ED-B when compared to wildtype ubiquitin. This is an evidence for the directed targeting of 1041-D11 to tumor tissues. Further, the tumour to blood-ratio of 1041-D11 in a cancer model clearly demonstrates in vivo activity of 1041-D11 variant in animals (data not shown).

FIGS. 17A-17E show the high selectivity and specificity 1041-D11-TNF-alpha fusion protein for ED-B.

Figure 17A:
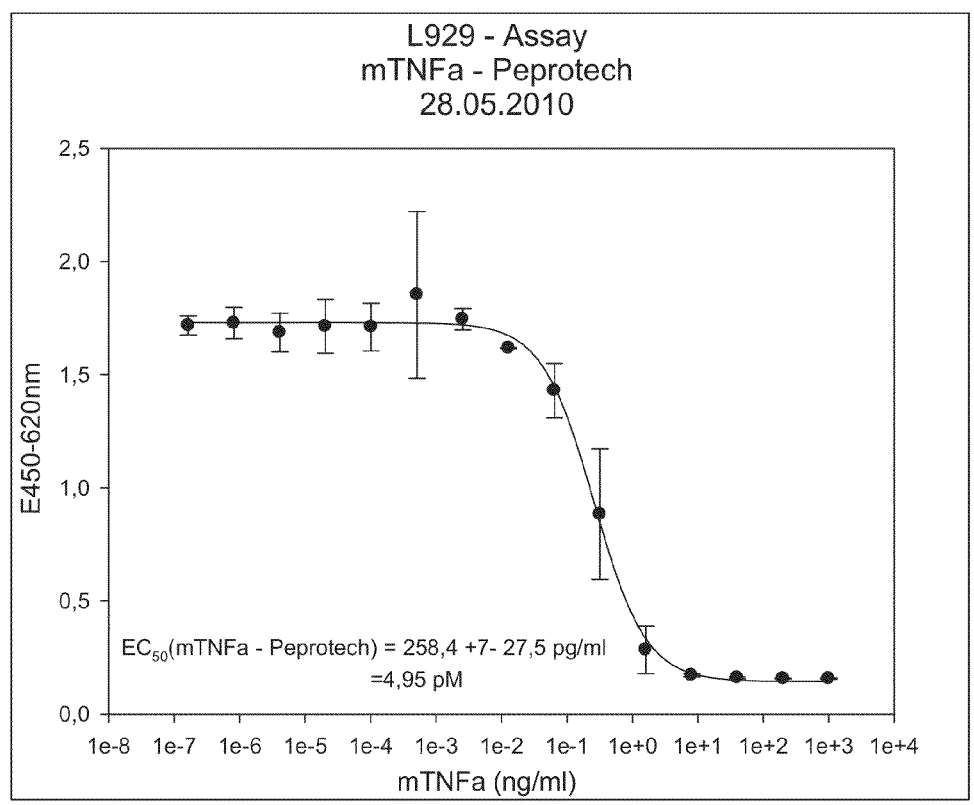
Figure 17B:
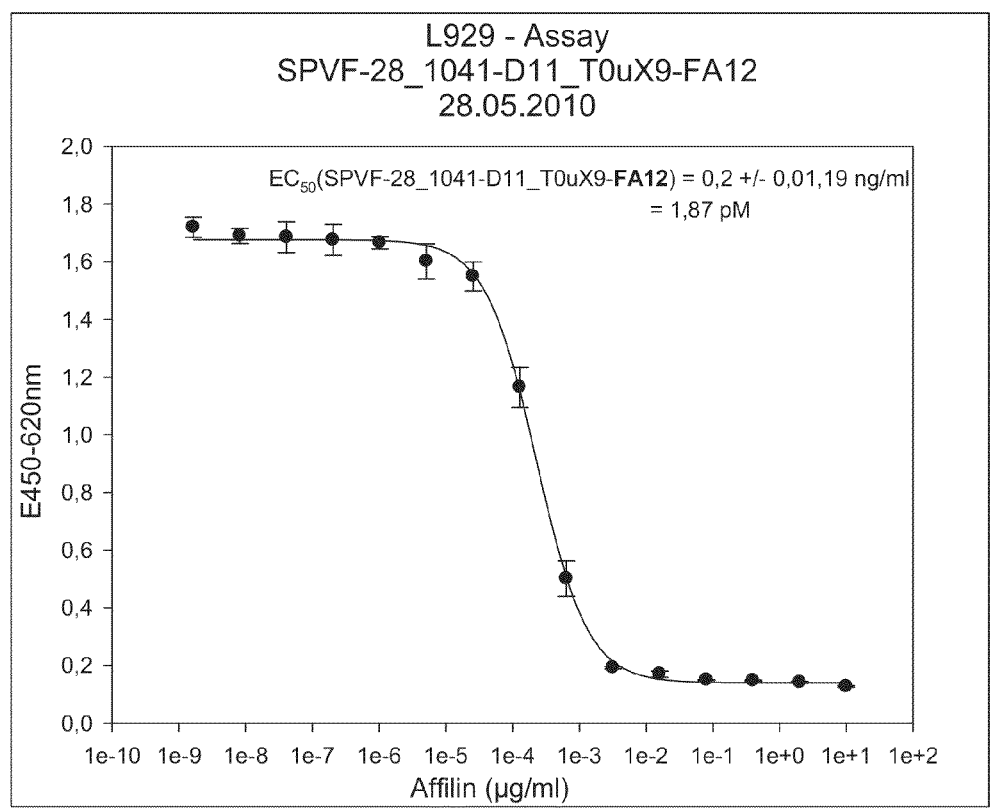

FIGS. 17A and 17B: Apoptosis inducing TNF-alpha activity of the 1041-D11-TNFα fusion protein was tested in a cell based assay (L929 cells). The figures clearly show that the 1041-D11-TNF-alpha fusion protein (FIG. 17B) is as active as free TNF-alpha (FIG. 17B) in cell culture.

Figure 17C:
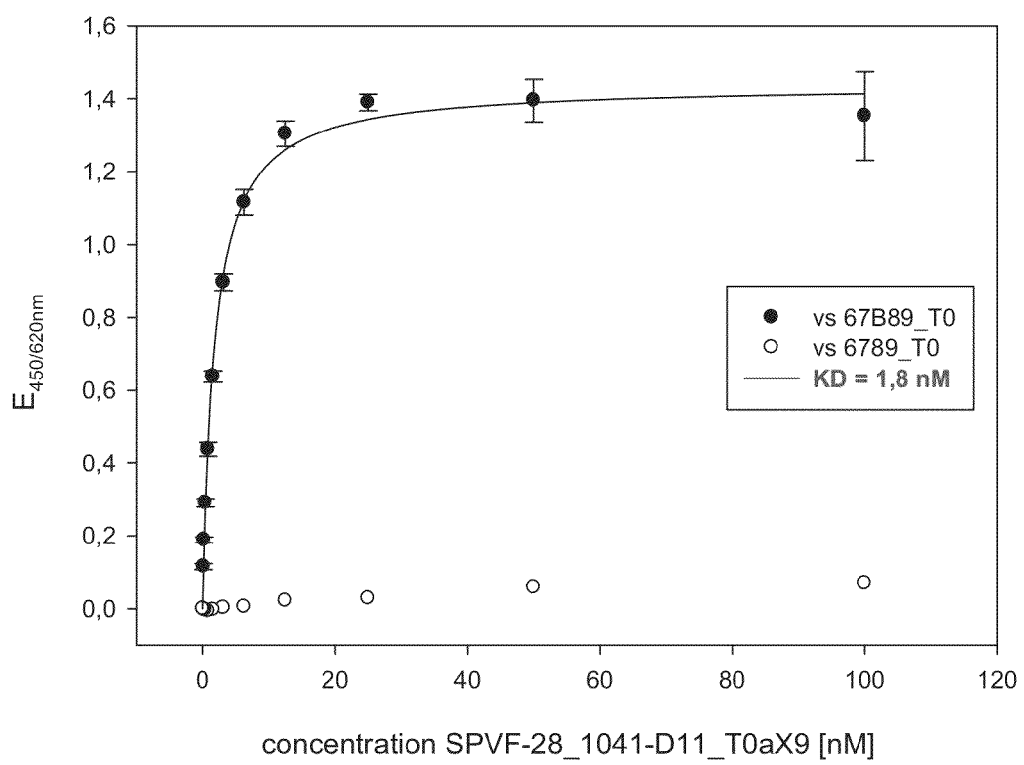

FIG. 17C demonstrates the high selectivity of the hetero-dimeric ubiquitin 1041-D11 TNF-alpha fusion protein to the target ED-B. The human ED-B fibronectin domain 67B89 is bound with an apparent KD value of 1.8 nM to variant 1041-D11 (closed circles), showing the high affinity for the target. Human fibronectin lacking the ED-B domain (h6789) is not bound by 1041-D11 TNFalpha (open circles).

Figure 17D:
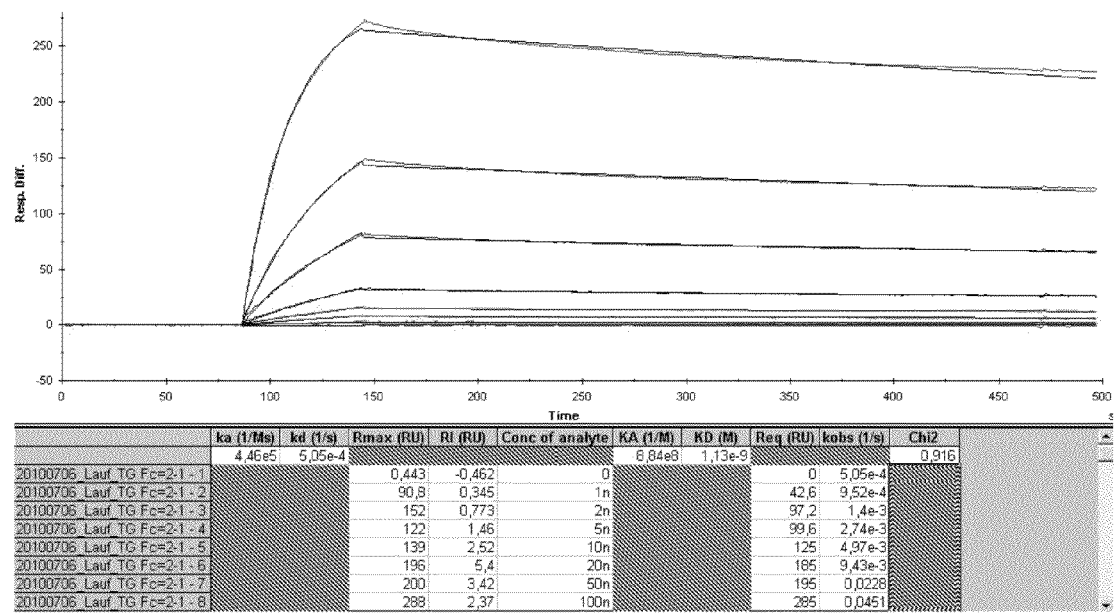

FIG. 17D shows the binding analysis of modified ubiquitin-based ED-B binding 1041-D11-TNF-alpha fusion protein by BIACORE® assays. The results demonstrate the high affinity of 1041-D11 TNF-alpha fusion protein with a KD value of 1.13 nM.

Figure 17E:
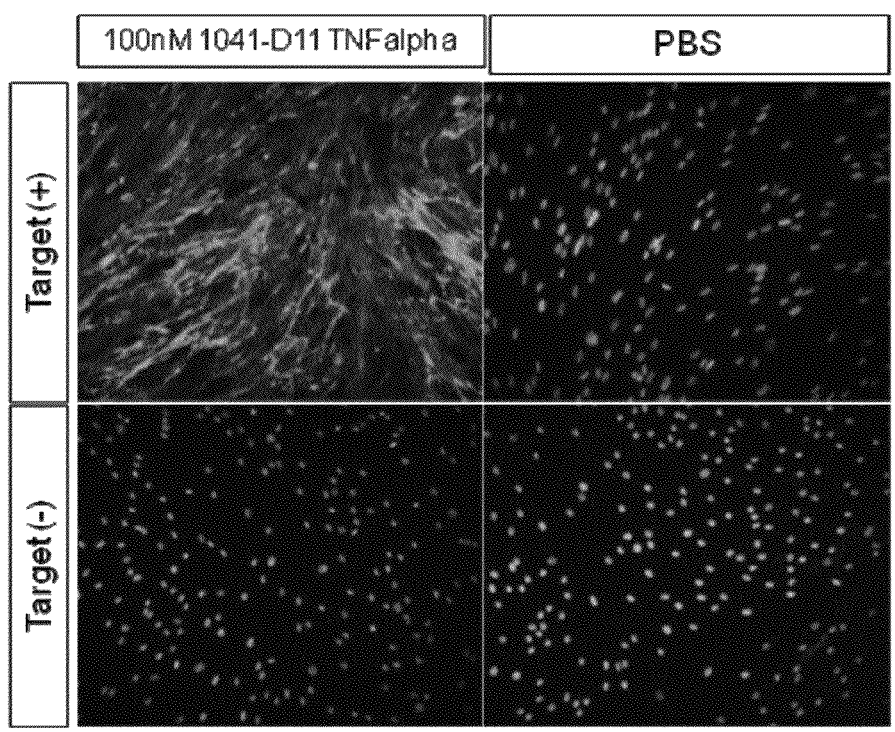

FIG. 17E shows the high binding specificity observed with variant 1041-D11 in cell culture is preserved when the 1041-D11 is fused to TNF-alpha. The fusion protein specifically binds to EDB expressing cells. Thus, 1041-D11 TNF-alpha fusion protein binds with very high affinity and specificity to the target ED-B ("target(+)"). In serum without ED-B ("target (−)"), no cross reaction can be observed.

Figure 18:
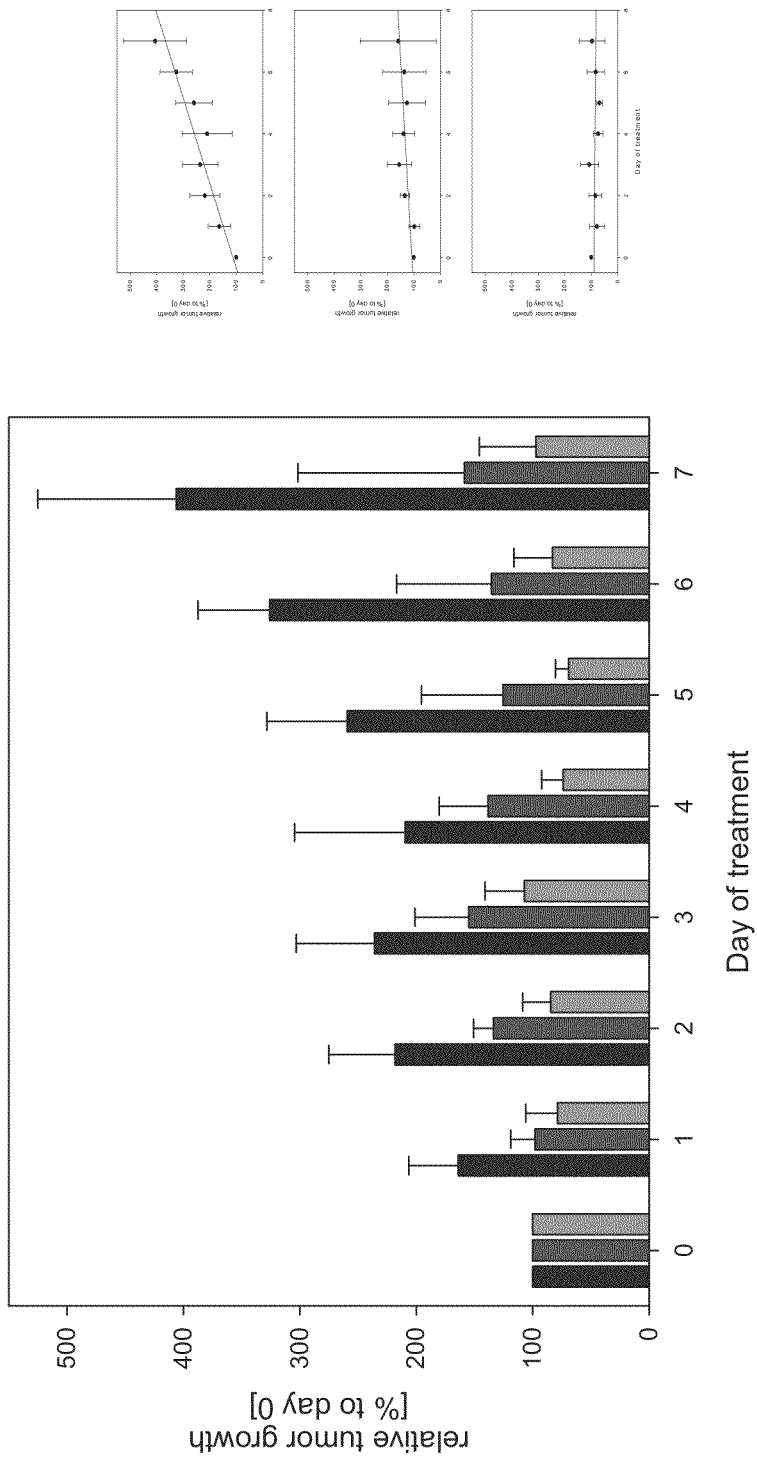

FIG. 18 shows the relative tumor growth in vivo during the time of treatment of mice for 7 days with variant 1041-D11 fused to TNFalpha in combination with Melphalan. The data clearly show that 1041-D11-TNFalpha in combination with the cytostatic agent Melphalan reduces the relative tumor growth more efficiently that mTNF-alpha in combination with Melphalan or Melphalan alone. The tumor growth kinetic 7 days after treatment shows the efficient reduction of tumors by 1041-D11-mTNFα. This is a clear evidence for the efficacy of a treatment of tumors with fusion protein 1041-D11-TNF-alpha in combination with Melphalan. ED-B is identical in several mammalian species, including mice and human, and thus, the results are predictive of the performance of variant 1041-D11-TNFalpha in humans.

EXAMPLES

The following Examples are provided for further illustration of the invention. The invention is particularly demonstrated with respect to the modification of ubiquitin as an example. The invention, however, is not limited thereto, and the following Examples merely show the practicability of the invention on the basis of the above description. For a complete disclosure of the invention reference is made also to the literature cited in the application and in the annex which are all incorporated in their entirety into the application by reference.

Example 1

Identification of Hetero-Dimeric ED-B Binding Proteins Based on Modified Ubiquitin Proteins Library Construction and Cloning Unless otherwise indicated, established recombinant genetic methods were used, for example as described in Sambrook et al. A random library of human ubiquitin heterodimers with high complexity was prepared by concerted mutagenesis of in total 15 selected amino acid positions. The modified amino acids, which were substituted by NNK triplets, comprised at least 3 amino acids selected from positions 2, 4, 6, 8, 62, 63, 64, 65, 66, 68 within the proximal (first) ubiquitin monomer and at least 3 amino acids selected from positions 2, 4, 6, 8, 62, 63, 64, 65, 66, 68 within the distal (second) ubiquitin monomer. Both ubiquitin monomers were genetically linked (head-to-tail) by a Glycine/Serine linker with at least the sequence GIG or by Glycine/Serine linker with at least the sequence SGGGG (SEQ ID NO: 48), for example GIG, SGGGG (SEQ ID NO: 48), SGGGGIG (SEQ ID NO: 49), SGGGGSGGGGIG (SEQ ID NO: 32) or SGGGGSGGGG (SEQ ID NO: 50), but any other linker is possible.

TAT Phage Display Selection

The heterodimeric ubiquitin library was enriched against the target using, for example, TAT phage display as selection system. Other selection methods known in the art can be used. The target can be immobilized nonspecifically onto protein binding surfaces or via biotinylated residues which were covalently coupled to the protein. The immobilization via biotin onto streptavidin beads or neutravidin strips is preferred. The target-binding phages are selected either in solution or on immobilized target; for example, the biotinylated and immobilized target with phage was incubated followed by washing of the phages bound to the matrix and by elution of matrix-bound phages. In each cycle following target incubation, the beads were magnetically separated from solution and washed several times. In the first selection cycle the biotinylated target was immobilized to neutravidin strips whereas in cycles two to four selections in solution was performed followed by immobilization of target-phage complexes on Streptavidin-coated Dynabeads® (Invitrogen). After washing in the first two selection cycles the phages of target-binding modified ubiquitin molecules were released by elution with acidic solution. In selection cycles three and four elution of phages was carried out by competitive elution with excess target. The eluted phages were reamplified. To direct specificty of binders a protein similar to the target can be included during selection.

Alternatively to TAT Phage Display Selection: Ribosome Display Selection

The ubiquitin library was enriched against the target using, for example, ribosome display as selection system (Zahnd et al., 2007, Ohashi et al., 2007). Other selection methods known in the art can be used. The target was biotinylated according to standard methods and immobilized on Streptavidin-coated Dynabeads® (Invitrogen). Ternary complexes comprising ribosomes, mRNA and nascent ubiquitin polypeptide were assembled using the PURExpress™ In Vitro Protein Synthesis Kit (NEB). Two primary rounds of selection were performed, wherein ternary complexes were incubated followed by two similar rounds of selection. In each cycle following target incubation, the beads were magnetically separated from solution and washed with ribosome display buffer with increasing stringency. After washing in the first two selection cycles, the beads were again magnetically separated from solution and mRNA of target-binding modified ubiquitin molecules was released from ribosomes by addition of 50 mM EDTA. In selection cycles three and four elution of mRNA was carried out by competitive elution with excess target (Lipovsek and Pluckthun, 2004). After each cycle, RNA purification and cDNA synthesis were performed using RNeasy MinElute Cleanup Kit (Qiagen, Germany), Turbo DNA-free Kit (Applied Biosystems, USA) and Transcriptor Reverse Transcriptase (Roche, Germany).

Cloning of Enriched Pools

After the fourth selection cycle the synthesized cDNA was amplified by PCR via primers F1 (GGAGACCACAACG-GTTTCCCTCTAGAAATAATTTTGTT-TAACTTTAAGAAGGAGA TATACATATG) (SEQ ID NO: 9) and WUBI(co)RD_xho (AAAAAAAAACTCGAGAC-CGCCACGCAGACGCAGAACCAG) (SEQ ID NO: 10), cut with restriction nucleases NdeI and XhoI (Promega, USA) and ligated into expression vector pET-20b(+) (Merck, Germany) via compatible cohesive ends.

Single Colony Hit Analysis

After transformation into NovaBlue(DE3) cells (Merck, Germany) ampicillin-resistant single colonies were grown for 6 h at 37° C. in 200 μl SOBAG medium (SOB medium containing 100 μg/ml ampicilin and 20 g/l glucose). expression of the ED-B-binding modified ubiquitin was achieved by cultivation for 16 h at 37° C. in 96-well deep well plates (Genetix, UK) using 500 μl auto induction medium ZYM-5052 (Studier, 2005). Cells were harvested by 15 min of centrifugation at 4° C. and 3600 g and subsequently lysed by incubation for 30 min at 37° C. with 300 μl lysis buffer per well, containing 0.2× BugBuster® (Merck, Germany), 0.3 mg/ml lysozyme (VWR, Germany) 0.2 mM PMSF (Roth, Germany), 3 mM MgCl$_2$ and 0.2 U/ml Benzonase (VWR, Germany) in 50 mM NaH$_2$PO$_4$, 300 mM NaCl, pH8. After centrifugation for 30 min at 4° C. and 3600 g the resulting supernatants were screened by ELISA using Nunc MediSorp plates (Thermo Fisher Scientific, USA) coated with 4 μg/ml ED-B and a ubiquitin-specific Fab fragment conjugated with horseradish peroxidase (POD). As detecting reagent TMB-Plus (Biotrend, Germany) was used and the yellow colour was developed using 50 μl/well 0.2 M H$_2$SO$_4$ solution and measured in a plate reader at 450 nm versus 620 nm.

Usually, several, for example, four cycles of selection display versus ED-B were carried out. In the last two cycles of selection binding molecules were eluted with an excess of free ED-B. These ED-B-binding variants were identified, among others:

Sequence of 46H9
(SEQ ID NO: 6)
MGIVVRTLTGKTITLEVEPSDTIENVKAKIQDKEGIPPDQQRLIWAGKQL

EDGRTLSDYNIPHPTLLHLVLRLRGGSGGGGSGGGGIGMQIFVHTMTGKT

ITLEVEPSDTIENVKAKIQDKEGIPPDQQRLIWAGKQLEDGRTLSDYNIK

PIAELHLVLRLRGG

Sequence of 9E12
(SEQ ID NO: 7)
MRIPVYTLTGKTITLEVEPSDTIENVKAKIQDKEGIPPDQQRLIWAGKQL

EDGRTLSDYNIPPFARLHLVLRLRGGSGGGGSGGGGIGMQIFVMTRTGKT

ITLEVEPSDTIENVKAKIQDKEGIPPDQQRLIWAGKQLEDGRTLSDYNIM

NARLLHLVLRLRGG

Sequence of 22D1
(SEQ ID NO: 8)
MLILVRTLTDKTITLEVEPSDTIGNVKAKIQDKEGIPPDQQRLIWAGKQL

EDGRTLSDYNISVGAMLHLVLRLRGGSGGGGSGGGGIGMQIFVLTWTGKT

ITLEVEPSDTIENVKAKIQDKEGIPPDQQRLIWAGKQLEDGRTLSDYNIR

RLPPLHLVLRLRGG

A sequence alignment of wild type ubiquitin monomer (Ubi monomer wt), with wild type ubiquitin dimer (ubi dimer wt) and wild type ubiquitin protein (Ub2-TsX in FIG. 9, with an exchange in Position 45 of each monomer and with two substitutions at the C-terminus) with the modified ubiquitin hetero-dimeric variant 1041-D11 is shown in FIG. 9. In Ub2-TsX the substitutions at the C-terminus (GG to AA) of the monomer increase the stability in serum because deubiquitinases cleave behind the GG of ubiquitin but not behind the AA. The secondary structure of the wild type ubiquitin compared to the ubiquitin with these substitutions at the C-terminus is almost identical.

The modified ubiquitins with superior ED-B binding activity referred to as 1041-D11 (shown in FIG. 9; SEQ ID NO: 36) or 1045-D10 are identified by the following amino acid replacements as compared to the wild type: in the first module: K6W, L8W, K63R, E64K, S65F, T66P; in the second module: K6T, L8Q, Q62W, K63S, E64N, S65W, T66E; optionally Q2R (in variant 1041-D11, but not in variant 1045-D10). Suitable preferred linkers for the fusion protein are those of SEQ ID NO: 32 or the sequence GIG. However, there are many conceivable linkers which can be used instead.

As a further preferred example a protein is provided by the following sequence wherein X may be any amino acid (SEQ ID NO: 47). As linker, SGGGGSGGGGIG (SEQ ID NO: 32) was used here (shown in italics). It is to be understood that also other kind of linkers or no linker are feasible alternatives.

(SEQ ID NO: 51)
MTIWVHTLTGKTITLEVEPSDTIENVKAKIQDKEGIPPDQQRLIWAGKQL

EDGRTLSDYNINFKLSLHLVLRLRGG*SGGGGSGGGG*IGMQIFVXTXTGKT

ITLEVEPSDTIENVKAKIQDKEGIPPDQQRLIWAGKQLEDGRTLSDYNIX

XXXXLHLVLRLRGG

Figure 2:
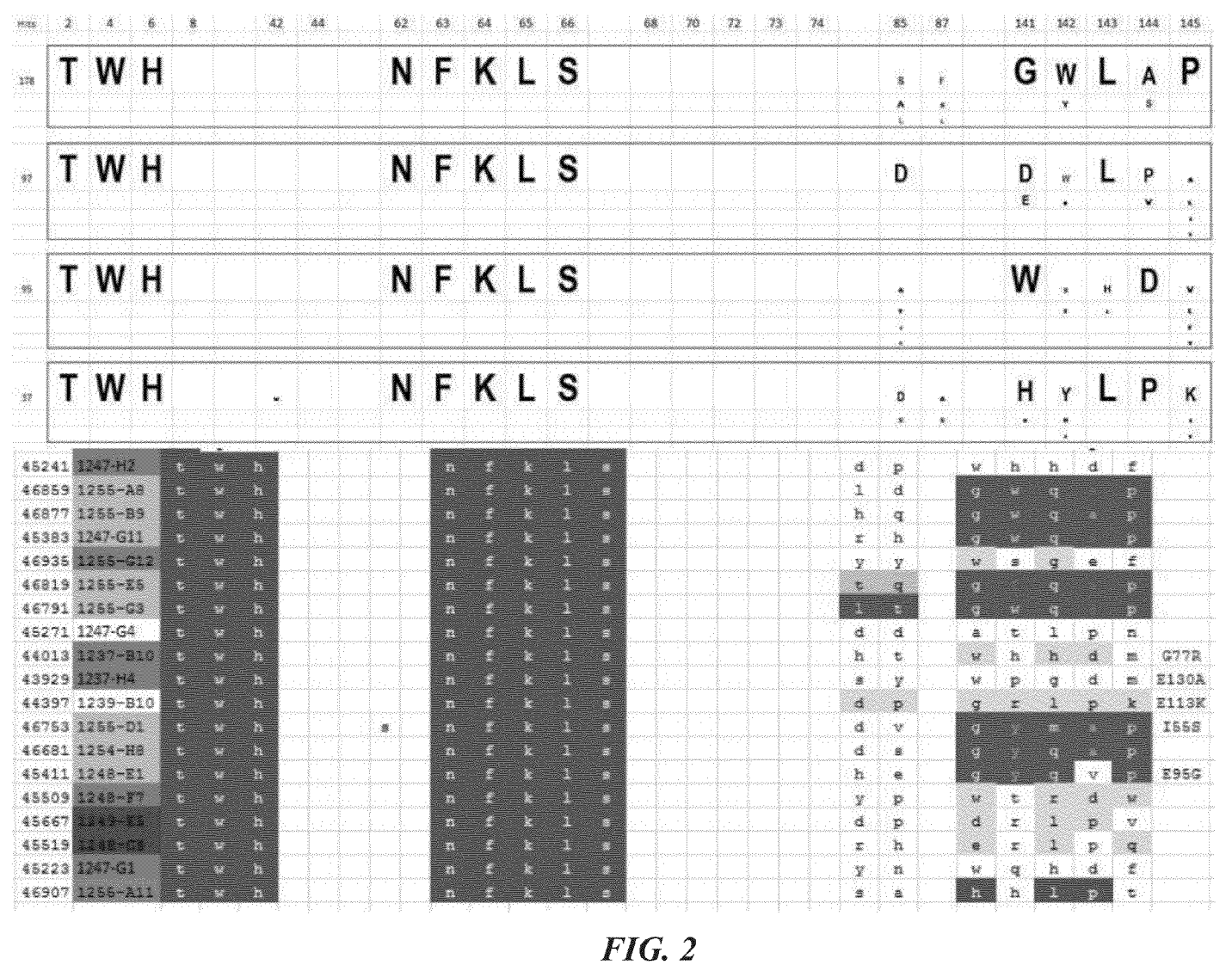

The consensus sequences of examples of proteins with these sequences are shown in FIG. 2.

Example 2

Production of Fusion Proteins from ED-B-Binding Modified Ubiquitin Variants and Human TNFalpha (hTNFa)

The variants are expressed as fusion proteins between the modified ubiquitin, for example hetero-dimeric variant1041-D11, and mouse or human TNFα in *E. coli*. Protein analysis of the fusion protein includes: protein expression and purity, no aggregation potential, TNFα activity in cell culture, affinity for target protein ED-B, Selectivity, specific binding in cell culture. Prerequisite for animal experiment to induce tumor shrinkage in F9 tumor bearing mice is a fusion with mouse TNFα.

Step 1

Production of a Vector for Cloning of Fusion Proteins (pETSUMO-TNFa)

pETSUMOadapt is a modified vector pETSUMO (Invitrogen), which was modified by insertion of an additional multiple cloning site (MCS). Starting from TNFalpha cloned in pETSUMOadapt, restriction sites for the insertion of modified ubiquitin variants binding ED-B-were introduced. The resulting construct has the structure His$_6$-SUMO-TNFa with the following DNA-sequence (SEQ ID NO: 11):

ATGGGCAGCAGCCATCATCATCATCATCACGGCAGCGGCCTGGTGCCGCG

CGGCAGCGCTAGCATGTCGGACTCAGAAGTCAATCAAGAAGCTAAGCCAG

AGGTCAAGCCAGAAGTCAAGCCTGAGACTCACATCAATTTAAAGGTGTCC

GATGGATCTTCAGAGATCTTCTTCAAGATCAAAAAGACCACTCCTTTAAG

AAGGCTGATGGAAGCGTTCGCTAAAAGACAGGGTAAGGAAATGGACTCCT

TAAGATTCTTGTACGACGGTATTAGAATTCAAGCTGATCAGACCCCTGAA

GATTTGGACATGGAGGATAACGATATTATTGAGGCTCACAGAGAACAGAT

TGGTGGT<u>GTGCGTAGCAGCAGC</u>CGTACCCCGAGCGATAAACCGGTGGCGC

ATGTGGTGGCGAATCCGCAGGCGGAAGGCCAGCTGCAGTGGCTGAACCGT

CGTGCGAATGCGCTGCTGGCCAACGGCGTGGAACTGCGTGATAATCAGCT

GGTTGTGCCGAGCGAAGGCCTGTATCTGATTTATAGCCAGGTGCTGTTTA

AAGGCCAGGGCTGCCCGAGCACCCATGTGCTGCTGACCCATACCATTAGC

CGTATTGCGGTGAGCTATCAGACCAAAGTGAACCTGCTGTCTGCGATTAA

AAGCCCGTGCCAGCGTGAAACCCCGGAAGGCGCGGAAGCGAAACCGTGGT

ATGAACCGATTTATCTGGGCGGCGTGTTTCAGCTGGAAAAAGGCGATCGT

CTGAGCGCGGAAATTAACCGTCCGGATTATCTGGATTTTGCGGAAAGCGG

CCAGGTGTATTTTGGCATTATTGCGCTG<u>TAATAA</u>

The TNFalpha sequence was amplified via PCR by introducing a BamHI- and XhoI-site. Primers used:

SUMO-EDB-TNFa-fw (SEQ ID NO: 12):
TTT TTT GGA TCC <u>GTG CGT AGC AGC AGC</u>

SUMO-EDB-TNFa-rev (SEQ ID NO: 13):
CTT GTC TCT CGA GGC GGC CGC <u>TTA TTA C</u>

The fw-primer (SEQ ID NO: 12) recognizes the first 15 base pairs of TNFa (underlined region) and has a BamHI-sequence (shown in bold). The rev-primer (SEQ ID NO: 13) contains the last base pair of TNFa, the estop codons (underlined) and a XhoI-restriction site (bold).

PCR Reaction Mix (100 µl):

84.5 µl H₂O; 10 µl 10× Pwo buffer+Mg; 2 µA 10 mM dNTPs (=200 µM); each 0.5 µl 100 µM primer fw/rev (=each 0.5 µM); 2 µl DNA (=0.25 µg); 0.5 µl Pwo polymerase (=2.5 U; Roche)

PCR-Program:

3 min 94° C., 30 s 94° C., 30 s 60° C., 2 min 72° C. (steps 2-4: 30 cycles), 5 min 72° C., followed by 4° C. followed by purification of the PCR product with the Qiagen-MinElute-Kit (elution in 10 µl EB). The PCR product is introduced in the MCS of the vector pETSUMOadapt via BamHI-XhoI-restriction and ligation.

Restriction mix (100 µl):

Vector: 83 µl H₂O; 10 µl 10×NE buffer 3; 1 µl 100×BSA; 3 µl BamHI (=30 U; NEB), 1.5 µl XhoI (=30 U; NEB); 1.65 µl vector; 3 h 37° C. incubation.

PCR product: 76.5 µl H₂O; 10 µl 10×NE buffer 3; 1 µl 100×BSA; 3 µl BamHI (=30 U; NEB), 1.5 µl XhoI (=30 U; NEB); 8 µl insert; 3 h 37° C. incubation Separation of Restriction in 1% Agarosegel (100 V 60 min run); cut vector fragment (5659 bp) and insert (491 bp); Purification with Qiagen gel extraction kit (elution in 30 µl EB).

Ligation (20 µl):

15.2 µl H₂O; 2 µl 10× T4-DNA ligase buffer; 2.26 µl Vector (200 ng); 0.54 µl insert (40 ng) 5 min 65° C. incubation; cool to 16° C.; add 1 µl T4-DNA ligase (=3 U; NEB); 16 h 16° C. incubation.

NaAc/Isopropanol-Precipitation:

Ligation-mixture (20 µl)+2.2 µl 3 M NaAc (pH 5.0)+22.2 µl isopropanol; 30 min −20° C.; 15 min 4° C. 13000 Upm; resuspend pellet in 500 µl 70% EtOH; spin; resuspend pellet in 10 µl H₂O.

Transformation:

Mix electro-competent Novablue(DE3)-cells (40 µl-aliquot) with 10 µl ligation product; transfer to 0.1-cm-elextroporation cuvette; puls in electroporator (1.8 kV, 50 µF, 100 Ohm); incubate solution with 1 ml SOC-medium 45 min 37° C. 220 Upm; 100 µl on LB-plate with Kanamycin; incubation overnight 37° C.

Step 2

Cloning of Modified Ubiquitin-Based EDB-Fusion Proteins

For the production of fusions of EDB-binding modified ubiquitin-based variants and TNFa, the EDB-modified ubiquitin-based sequence of interest in amplified from a pET20b-vector via PCR; BsaI- and BamHI-restriction sites are introduced. The method is suitable for monomeric and for dimeric EDB-modified ubiquitin-based variants. Primer for monomeric WT-Ubiquitin (Wubi):

```
SUMO-EDB-WUBI-fw (SEQ ID NO: 14)::
GTT CCA AGG TCT CAT GGT ATG CAG ATC TTC GTG

SUMO-EDB-Linker-rev (SEQ ID NO: 15)::
GTG GTG GGA TCC ACC GCC ACC ACC AGA ACC GCC ACG

CAG ACG
```

The fw-primer (SEQ ID NO: 14) recognizes the first 15 base pairs of modified ubiquitin (underlined region) and has a BsaI-sequence (shown in bold). The rev-Primer (SEQ ID NO: 15) recognizes the last 15 base pairs of modified ubiquitin and inserts an amino acid linker (sequence SGGGG) and a BamHI-restriction site (bold). For each modified ubiquitin-based-variant, a specific fw-primer is used. Primers monomeric EDB-modified ubiquitin-based variants 1H4, 5E1 and 4B10:

```
1H4 (MWIKV . . . ): Primer (SUMO-EDB-1H4-fw) (SEQ
ID NO: 16):
GTT CCA AGG TCT CAT GGT ATG TGG ATC AAG GTG 4B10 (MLILV): Primer (SUMO-EDB-4B10-fw) (SEQ ID
NO: 17):
GTT CCA AGG TCT CAT GGT ATG TTG ATC CTG GTG 5E1 (MVINV . . . ): Primer (SUMO-EDB-5E1-fw) (SEQ
ID NO: 18):
GTT CCA AGG TCT CAT GGT ATG GTT ATC AAT GTG
```

The rev-primer is used for all monomeric modified ubiquitin-based variants. Rev-Primer for dimeric modified ubiquitin-based variants:

```
Dimer-t0a-rev (SEQ ID NO: 19):
GTG GTG GGA TCC ACC GCC ACC ACC AGA ACC ACC ACG

TAA ACG
``` fw-Primer for the cloning of dimeric WT-ubiquitins (WubiHubi) and for dimeric EDB-modified ubiquitin-based variants:

```
WT (MQIFV . . . ) Primer (SUMO-EDB-WUBI-fw) (SEQ
ID NO: 20):
GTT CCA AGG TCT CAT GGT ATG CAG ATC TTC GTG
```

(note: fw-Primer for dimerics WT-ubiquitin is identical to fw-Primer for monomeric WT-ubiquitin.)

```
9E12 (MRIPV . . . ): Primer (9E12-t0a-fw) (SEQ ID
NO: 21):
GTT CCA AGG TCT CAT GGT ATG CGT ATC CCT GTG 24H12 (MVIKV . . . ): Primer (24H12-t0a-fw) (SEQ
ID NO: 22):
GTT CCA AGG TCT CAT GGT ATG GTT ATC AAG GTG 15G7 (MEIGV . . . ): Primer (15G7-t0a-fw) (SEQ ID
NO: 23):
GTT CCA AGG TCT CAT GGT ATG GAG ATC GGT GTG 22D1 (MLILV . . . ): Primer (22D1-t0a-fw) (SEQ ID
NO: 24):
GTT CCA AGG TCT CAT GGT ATG CTT ATC TTG GTG
```

PCR-Mixture (100 µl):

84.5 µl H₂O; 10 µl 10× Pwo-buffer+Mg; 2 µl 10 mM dNTPs (=200 µM); each 0.5 µl 100 µM Primer fw/rev (=je 0.5 µM); 2 µl DNA (dependent on the variant); 0.5 µl Pwo-Polymerase (=2.5 U; Roche)

PCR-Program:

1. 3 min 94° C.
2. 30 s 94° C.
3. 30 s 60° C.
4. 2 min 72° C. (steps 2-4: 30 cycles)
5. 5 min 72° C., followed by 4° C.

Purification of the PCR-products in agarose gel, cut required band and purify with Qiagen-gel extraction kit. Cloning of the PCR-product via BsaI-BamHI-restriction (in pETSUMO-TNFa)

Restriction (100 µl):

75 µl H$_2$O; 10 µl 10×NEBuffer 3; 1 µl 100×BSA; 3 µl BsaI (=30 U; NEB); 8 µl DNA (Vector or PCR-Product)$_2$ h 50° C. incubation, 10 min 65° C., add 3 µl BamHI (=30 U; NEB), 2 h 37° C. Separation of restriction in 1% agarose gel; cut vector fragment and insert; purification with Qiagen-gel extraction kit (elution in 30 µl EB).

Ligation (20 µl):

12.5 µl H$_2$O; 2 µl 10× T4-DNA ligase buffer; 5 µl vector (66 ng); 0.5 µl insert (variabel) 5 min 65° C. incubation; cool to 16° C.; add 1 µl T4-DNA ligase (=3 U; NEB); 16 h 16° C. incubation NaAc/Isopropanol Precipitation (See Step 1)

Transformation in elektrocompetent Novablue(DE3)-cells as described above. The result is the following fusion construct: EDB-modified ubiquitin and TNFa in pETSUMO-adapt with der His$_6$-SUMO— modified ubiquitin-SGGGG-TNFa (359 amino acids with monomeric modified ubiquitin 447 amino acids with dimeric modified ubiquitin)

Example 3

Expression and Purification of Ubiquitin-Based-TNFalpha Fusion Proteins

DNA sequence analysis showed the correct sequences of the SUMO-TNFa fusion proteins. For expression of the variants the clones were cultivated in a shaker flask by diluting a preculture 1:100 with LB/Kanamycin and agitating the culture at 200 rpm and 37° C. up to an optical density at 600 nm (OD600) of 0.5. Expression was induced by adding IPTG (final concentration 1 mM). Culturing was continued for 4 hours at 30° C. and 200 rpm. The bacteria cells were harvested by centrifugation at 4° C., 6000× g for 20 min. The cell pellet was suspended in 30 ml of NPI-20 buffer including benzonase and lysozyme. Cells were disrupted by ultrasonication (3×20 sec) on ice. The supernatant containing the soluble proteins was obtained after centrifugation of the suspension at 4° C. and 40000×g for 30 min. Both proteins were purified by affinity chromatography at room temperature. One column of Ni-Agarose (5 ml, GE Healthcare) was equilibrated with 50 ml of NPI-20. The supernatant containing the soluble proteins was applied to the column, followed by a washing step with NPI-20. The bound protein was eluted with a linear gradient to 50% NPI-500 in 100 ml. Fractions were analyzed by SDS-PAGE with respect to their purity. Suitable fractions were pooled and applied to a gel filtration column (Superdex 75, 1.6×60 cm, GE Healthcare) equilibrated with SUMO-hydrolase cleavage buffer (50 mM Tris, 300 mM NaCl, pH 8.0) at a flow rate of 1 ml/min.

The cleavage reaction was done according to the manufactures instruction (Invitrogen). After cleavage the protein was applied to a Ni-agarose column (5 ml, GE Healthcare). His-tagged SUMO-hydrolase and His-tagged SUMO were bound to the column and the correct fusion protein passed the column (His-tag free). Purity of the proteins was proofed by rpHPLC analysis and gel electrophoresis. The correct molecular mass of the trimer (via TNFa) was confirmed using analytical SEC analysis (10/30 Superdex G75, GE Healthcare).

Example 4

Binding Analysis of Modified Ubiquitin-Based ED-B Binding Variants to Human ED-B Example 4A Binding Analysis of Modified Ubiquitin-Based ED-B Binding Variants by Concentration Dependent ELISA Binding of ubiquitin-based variants to human ED-B was assayed by a concentration dependent ELISA. Increasing amounts of purified protein applied to NUNC-medisorp plates coated with human ED-B, BSA and cellular fibronectin (cFN). Antigen coating with 50 µl (10 µg/ml) per well was performed at 4° C. overnight. After washing the plates with PBS, 0.1% Tween 20 pH 7.4 (PBST) the wells were blocked using blocking solution (PBS pH 7.4; 3% BSA; 0.5% Tween 20) at 37° C. for 2 h. Wells were washed again three times with PBST. Different concentrations of modified ubiquitin based ED-B binding protein were then incubated in the wells at RT for 1 h (50 µl volume)(in FIG. 10, as start concentration, 500 nM of 1041-D11 protein was used). After washing the wells with PBST, the anti-Ubi fab fragment (AbyD) POD conjugate was applied in an appropriate dilution (for example, 1:2000 or 1:6500) in PBST. The plate was washed three times with 300 µl buffer PBST/well. 50 µl TMB substrate solution (KEM-EN-Tec) were added to each well and was incubated for 15 min. The reaction was stopped by adding 50 µl 0.2 M H$_2$SO$_4$ per well. The ELISA plates were read out using the TECAN Sunrise ELISA-Reader. The photometric absorbance measurements were done at 450 nm using 620 nm as a reference wavelength. FIG. 1 shows clearly the specific binding of the 1H4 to ED-B with an apparent KD value of 11 nM. The variant 5E1 shows an apparent KD value of 7.7 µM and 4B10 of 280 nM respectively. FIG. 10 shows very high affinity binding of variant 1041-D11 to ED-B (KD=6.9 nM). Thus, only a few modifications (up to 8 substitutions in each monomer) in the ubiquitin-wildtype result in a very higher affinity binding to ED-B.

Example 4B

Binding Analysis of Modified Ubiquitin-Based ED-B Binding Variants by Competitive Concentration Dependent ELISA Competitive concentration dependent ELISAs analyzed the binding of ubiquitin variant 1041-D11 to immobilized ED-B containing fibronectin fragment (67B89) in the presence of increasing amounts of free target. Conditions of the ELISA were as described for Example 5A, except that 1041-D11 protein was preincubated with ED-B (67B89) (0 µM-10 µM) or also with negative control 6789 (0 µM-10 µM) for 1 h and subsequently the mixture was given to the target 67B89 that was placed on a Medisorp-plate; following this, the variant was detected by the corresponding antibody (anti-Ubiquitin-Fab-POD; dilution 1:6500). FIG. 11 shows that variant 1041-D11 has a very high affinity binding to ED-B (IC50=140 nM). The result shown in FIG. 10 is confirmed; only a few modifications (up to 8 substitutions in each monomer) in the ubiquitin-wildtype result in a very higher affinity binding to ED-B.

Example 4C

Binding Analysis of Modified Ubiquitin-Based ED-B Binding Variants by Concentration Dependent ELISA Simultaneously Analyzing the Serum-Stability of Binding Activity

The ELISA is performed using procedures well known in the art and as described above (Example 5A and 5B). ED-B (here referred to as 67B89) is coated to microtiter plates, the variant is bound to ED-B and detected by a specific ubiquitin-antibody (Anti-Ubi-Fab-POD). The variant in this assay is treated in different ways: the variant is incubated in mouse serum for 1 h at 37° C. (see in FIG. 13, circles in blue); the variant is incubated in rat serum for 1 h at 37° C. (in FIG. 13, circles in red); or the variant is incubated PBS for 1 h at 37° C. (in FIG. 13, circles in black). FIG. 13 shows that all KDs of variant 1041-D11 are between 10.3 nM (in PBS) to 20.74 nM (in mouse-serum).

Example 4D

Binding Analysis of Modified Ubiquitin-Based ED-B Binding Variants by BIACORE® Assays

Different concentrations of the variant were analyzed (for example, 0-200 nM of the variant, preferably 1041-D11) for binding to an ED-B containing fibronectin fragment (referred to as 67B89) immobilized on a CM5-chip (BIACORE®) using methods known to those skilled in the art. The obtained data were processed via the BIAevaluation software and 1:1-Langmuir-fitting. The $K_D$ of variant 1041-D11 was 1.0 nM, as shown in FIG. 12. The kinetic binding constants were $k_{on}=7.6*10^5$ $M^{-1}s^{-1}$; $k_{off}=7.7*10^{-4}$ $s^{-1}$. The $K_D$ of the fusion protein 1041-D11-TNFalpha was 1.13 nM, as shown in FIG. 17D. The kinetic binding constants were $k_{on}=4.5*10^5$ $M^{-1}s^{-1}$; $k_{off}5.0^*10^{-4}$ $s^{-1}$.

Example 4E

Complex-Formation Analysis of Modified Ubiquitin-Based ED-B Binding Variants by SE-HPLC

For the analysis of complex formation, Tricorn Superdex 75 5/150 GL columns (GE-Healthcare) (V=3 ml) was used, protein amount of 50 μl was applied. Further conditions; buffer: 1×PBS, pH 7.3, flow-rate: 0.3 ml/min, run: 45 min (injection of sample: after 15 min). Condition: 0.72 nmol 1041-D11 protein+0.72 nmol ED-B (herein referred to 67B89 or also as a negative control 6789) incubated for 1 h at RT; then applied to column for analysis of complex-formation. In FIGS. 14A and 14B, only the variant is shown in black, only the target ED-B is shown in blue, the variant binding building a complex with ED-B in pink. FIG. 14A shows ED-B with the variant; FIG. 14B is the variant without ED-B. The figure shows that variant 1041-D11 builds a complex together with ED-B (67B89), but it builds no complex with 6789.

Example 5

Biological Assay of TNF Alpha

The physiological TNF-alpha-activity of TNF-alpha-modified ubiquitin based ED-B binding fusions has been determined using the L929 apoptosis assay (Flick et al., 1984 J. Immunol. Methods. 68:167-175). In this assay, TNF-alpha efficiently stimulates cell death in actinomycinD sensitized cells at $EC_{50}$ values in the picomolar range.

Cells have been resuspended in medium containing FBS and antibiotics. A cell suspension of 100 μl of a densitiy of $3.5×10^5$ cells/ml has been seeded into the wells of a 96 well standard cell culture plate followed by over night incubation in a humidified $CO_2$ incubator. Thereafter, the culture medium has been removed and 50 μl of medium containing FBS, ActinomycinD and antibiotics has been added to each well followed by a further 30 min incubation time. Thereafter, 50 μl of the test items, TNF-alpha-modified ubiquitin based ED-B binding-fusions or the human recombinant TNF-alpha control, at an appropriate concentration range of between $10^{-7}$ and $10^{-18}$ M, have been added. After a further 48 h incubation time the metabolic activity as a measure of cell survival was determined using WST-1 reagent (Roche).

Per test item at least three independent experiments have been conducted, each of them in triplicates. Each testing of TNF-alpha-modified ubiquitin based ED-B binding-fusion proteins was paralleled by testing a dose range of human recombinant TNF-alpha to get information on the inter assay variability.

The quantitative evaluation is based on the $EC_{50}$-value, i.e. the value according to the test item concentration promoting the survival of half of the cells.

TABLE 2

| | $EC_{50}$ value | |
|---|---|---|
| TNF-alpha-mub-Fusion | mub ®-TNF-alpha Fusion | Corresponding TNF-alpha |
| Wubi-TNF-alpha | 5.18 ± 2.84 pM | 7.97 ± 12.18 pM |
| Wubi-Hubi-TNF-alpha | 32.58 ± 11.26 pM | 5.02 ± 3.70 pM |
| SPWF-28__22-D1__TNF-alpha | 26.15 ± 14.41 pM | 2.32 ± 2.07 pM |
| SPWF-28__24-H12__TNF-alpha | 0.78 ± 0.24 pM | 3.01 ± 4.18 pM | mub: modified ubiquitin based ED-B binding

Of the TNF-alpha-modified ubiquitin based ED-B binding-fusion one ubiquitin monomer (Wubi) and three ubiquitin dimer constructs have been analyzed. Depending on the modified ubiquitin based ED-B binding variant coupled to the TNF-alpha moiety the TNF-alpha associated activity has been increased (SPWF-28__24-H12_TNF-alpha) or decreased (SPWF-28__22-D1_TNF-alpha, Wubi-Hubi-TNF-alpha) by about one order of magnitude. See FIGS. 17A-17F for variant 1041-D11 TNFalpha analysis.

Example 6

Binding Analysis of Ubiquitin Variants in Cell Culture Assays

The binding of variant 1041-D11 to cell culture cells was tested. Different cell culture cells were analysed, including normal human fetal lung fibroblast cells having high expression levels of ED-B (Wi38 cells), a mouse embryonic fibroblast cell line (Balb 3T3); a stromal cell line, derived from mouse bone marrow (ST-2) monocytes/macrophages (RAW 264.7), NHDF cells and murine fibroblast cells (LM).

The variant 1041-D11 (different concentrations) or an ED-B specific antibody (500 nM FV28 CH4/F1 1×PBS were incubated (1 h, 37° C.) with Wi38 cells (60,000 cells/ml; from ATCC), followed by fixation with methanol (5 min, −20° C.), blocking (5% Horse/PBS, 1 h); incubation with rabbit-a-Strep-Tag-IgG (obtained from GenScript A00875, 1:500) for 1 h and incubation with a-rabbit-IgG*Alexa488-AK (obtained from Invitrogen A11008, 1:1000) for 1 h. The nuclei were stained with DAPI. The first column in FIG. 15A shows the control using EDB antibodies, the second column shows the incubation of the variant at a protein concentration of 58.7 nM, the third column a ten-fold higher concentration of 1041-D11 protein (587 nM), the fourth column is a negative control with PBS. In the first row, human Wi38 fibroblast cells are shown in phase contrast, the second row shows the immunofluorescence and the third row a DAPI staining. It can be concluded from the pictures that the variant 1041-D11 binds to fixed Wi38 cells with high specificity to ED-B containing extracellular matrix. The negative control cell type NHDF are primary normal fibroblast cells, which express low levels of EDB-fibronectin (data not shown). The variants do not bind to those cells.

FIG. 15B shows the analysis of variant 1041-D11 on vital Wi38 cells. The negative control cells type NHDF are primary normal fibroblast cells, which express low levels of EDB-fibronectin. The cells were plated in chamber-slides (NUNC, 60000 cells/ml). To analyses the binding potential the cells were fixed with 100% MeOH for 5 min at −20° C. To block unspecific binding, the cells were incubated with 5% Horse-serum 1 h 37° C. The cells were tested with the variant 1041-D11, an ED-B specific antibody FV28 CH4/F1 as positive control or UB__2 as negative control with different concentrations 1 h RT. The proving occurred about an incubation with rabbit-a-Strep-Tag-IgG (obtained from GenScript A00875, 1:500) for 1 h and incubation with a-rabbit-IgG*Alexa488-AK (obtained from Invitrogen A11008, 1:1000) for 1 h. The nuclei were stained with DAPI. The first and third line in FIG. 15B shows the variant at different protein concentration and the negative control. The second and fourth line shows the incubation of the control using EDB antibodies. The first 2 lines show the variant and positive control on Wi38-cell line. The third and fourth line shows the incubation of NHDF-cells. It can be seen from the pictures that the variant 1041-D11 binds to vital Wi38 cells with high specificity to ED-B containing extracellular matrix. A control using NHDF cells which do not contain low EDB was performed (data not shown). The variants do not bind to those cells.

Similar experiments were performed using different cells types, for example Balb3T3 (ATCC, Kat-Nr. 30-2002), Raw (Lonza, Kat-Nr. BE12-115F/U1), ST-2 (Lonza, Ka t-Nr. BE12-115F/U1). FIGS. 15C and 15D show that the binding of ED-B is highly specific to murine Balb3T3 and ST-2 cells. No binding was observed to monocytes/macrophages (Raw) (data not shown).

As outlined above, FIG. 16A shows the specificity of 1041-D11 in tissue sections. F9 tumor tissues from seven samples were evaluated. Immune-histochemistry with 500 nM 1041-D11 resulted in ED-B specific vascular staining on F9 tumors from mice. ED-B is a highly specific marker for tumor vasculature. The target protein EDB is located on the abluminal side of the vessels. 1041-D11 specifically decorates the vasculature in tissue sections from F9 tumors. The obtained results are comparable to tissue specificity of the antibody fragment L19. In addition, 48 tissues were tested; no unspecific staining in any out of 48 tissues in FDA relevant panel was observed. FIG. 16B shows the accumulation of 1041-D11 in tumor cells in comparison to wild type Ubiquitin. Thus, fusion proteins based on modified ubiquitin specifically binding to ED-B are suitable an ED-B based targeted therapy for cancer.

Example 7

Efficacy In Vivo Study of 1041D11-TNFalpha

To establish the therapeutic efficacy of 1041-D11-TNFalpha, the compound was tested on F9 teratoma (see Borsi et al., 2003 Blood 102, 4384-4392) in mouse models. The ED-B expression in mice is comparable to the human in vivo situation and is suitable for an evaluation of the therapeutic impact of 1041-D11-mTNFalpha on cancer, preferably in combination with a cytotoxic compound such as Melphalan. F9 teratoma is an aggressive tumor with high vascular density. Borsi et al described that targeting of mouse TNFalpha via EDB-antibodies improve the efficacy of Melphalan which is demonstrated by retardation in tumor growth. The experimental schedule for the efficacy study was adapted from Borsi, 2003.

Stage 1 defined the pharmacologic active and tolerable dose with endpoints relating to the ratio of tumor vs. body weight, weight loss and survival. The inventors found that 1041D11-TNFalpha is tolerated at highest dose (6.75 µmol/g) but has no suppressing effect on tumor growth (>10% body weight after 3, 4 and 8 days→animals were killed), whereas 1041D11-TNFalpha at lowest dose (0.25 pmol/g) seems to retard tumor growth. Dosing groups further used were descending from 2.25 pmol/g 1041D11-TNFalpha.

Stage 2 of the study defined the dose-dependent efficacy with Melphalan having as endpoint the retardation of tumor growth (animal weight loss>10%, tumor>10% body weight, ulceration of tumor). In the study, 1041D11/mTNFa, murine TNFa, in combination with melphalan were tested. 168 animals were used, 14 Dosing groups (8 mice per group recruited when bearing F9 tumors of 300-400 mm$^3$); Administration of test sample i. v. followed by i. p. injection of Melphalan 24 h later Table 1 shows the dosing schedule:

| Group | Test item | Dose Melphalan** (mg/kg) | Dose TNF-α proteins (pmol/g)) | Route | Appl. vol | Animals (n)* |
|---|---|---|---|---|---|---|
| 1 | PBS | 0 | 0 | iv | 10 ml/kg | 8 |
| 2 | mouse TNF-α fusion protein | 0 | 2.25 | iv | 10 ml/kg | 8 |
| 3 | mouse TNF-α fusion protein | 0 | 0.75 | iv | 10 ml/kg | 8 |
| 4 | mouse TNF-α fusion protein | 0 | 0.25 | iv | 10 ml/kg | 8 |
| 5 | mouse TNF-α fusion protein | 0 | 0.025 | iv | 10 ml/kg | 8 |
| 6 | mouse TNF-α fusion protein | 0 | 0.0025 | iv | 10 ml/kg | 8 |
| 7 | Melphalan | 4.5 | 0 | ip | 10 ml/kg | 8 |
| 8 | Melphalan/ mouse TNF-α fusion protein* | 4.5 | 2.25 | ip/iv | 10/10 ml/kg | 8 |
| 9 | Melphalan/ mouse TNF-α fusion protein* | 4.5 | 0.75 | ip/iv | 10/10 ml/kg | 8 |
| 10 | Melphalan/ mouse TNF-α fusion protein* | 4.5 | 0.25 | ip/iv | 10/10 ml/kg | 8 |
| 11 | Melphalan/ mouse TNF-α fusion protein* | 4.5 | 0.025 | ip/iv | 10/10 ml/kg | 8 |
| 12 | Melphalan/ mouse TNF-α fusion protein* | 4.5 | 0.0025 | ip/iv | 10/10 ml/kg | 8 |

-continued

| | | Dose | | | |
|---|---|---|---|---|---|
| Group | Test item | Melphalan** (mg/kg) | TNF-α proteins (pmol/g)) | Route | Appl. vol | Animals (n)* |
| 13 | mouse TNF-α | 0 | 0.25 | iv | 10 ml/kg | 8 |
| 14 | Melphalan/ mouse TNF-α | 4.5 | 0.25 | ip/iv | 10/10 ml/kg | 8 |

*animals with subcutaneous tumors of 300-400 mm3
**Melphalan is applied 24 hours after mouse TNF-α protein injection
the MTD will be determined in study P10.0164

FIG. 18 shows the relative tumor growth during the time of treatment (7 days). FIG. 18 clearly shows that our compound 1041-D11-TNFalpha in combination with Melphalan reduces the relative tumor growth more efficiently that mTNFalpha in combination with Melphalan or Melphalan alone. The tumor growth kinetic 7 days after treatment shows the significant reduction of tumors by 1041-D11-mTNFa. This is a clear evidence for efficacy in combination with Melphalan.

PUBLICATIONS

1. Birchler, M., F. Viti, L. Zardi, B. Spiess, and D. Neri. 1999. Selective targeting and photocoagulation of ocular angiogenesis mediated by a phage-derived human antibody fragment. Nat Biotechnol 17:984-8.
2. Brenmoehl, J., M. Lang, M. Hausmann, S, N. Leeb, W. Falk, J. Scholmerich, M. Goke, and G. Rogler. 2007. Evidence for a differential expression of fibronectin splice forms ED-A and ED-B in Crohn's disease (CD) mucosa. Int J Colorectal Dis 22:611-23.
3. Dubin, D., J. H. Peters, L. F. Brown, B. Logan, K. C. Kent, B. Berse, S. Berven, B. Cercek, B. G. Sharifi, R. E. Pratt, and et al. 1995. Balloon catheterization induced arterial expression of embryonic fibronectins. Arterioscler Thromb Vasc Biol 15:1958-67.
4. Goodsell, D. S. 2001. FUNDAMENTALS OF CANCER MEDICINE: The Molecular Perspective: Antibodies. The Oncologist 6:547-548.
5. Kaczmarek, J., P. Castellani, G. Nicolo, B. Spina, G. Allemanni, and L. Zardi. 1994. Distribution of oncofetal fibronectin isoforms in normal, hyperplastic and neoplastic human breast tissues. Int J Cancer 59:11-6.
6. Menrad, A., and H. D. Menssen. 2005. ED-B fibronectin as a target for antibody-based cancer treatments. Expert Opin Ther Targets 9:491-500.
7. Pujuguet, P., A. Hammann, M. Moutet, J. L. Samuel, F. Martin, and M. Martin. 1996. Expression of fibronectin ED-A+ and ED-B+ isoforms by human and experimental colorectal cancer. Contribution of cancer cells and tumor-associated myofibroblasts. Am J Pathol 148:579-92.
8. Trachsel, E., M. Kaspar, F. Bootz, M. Detmar, and D. Neri. 2007. A human mAb specific to oncofetal fibronectin selectively targets chronic skin inflammation in vivo. Invest Dermatol 127:881-6.
9. Van Vliet, A., H. J. Baelde, L. J. Vleming, E. de Heer, and J. A. Bruijn. 2001. Distribution of fibronectin isoforms in human renal disease. J Pathol 193:256-62.
10. Lipovsek, D., and Pluckthun, A. (2004). In-vitro protein evolution by ribosome display and mRNA display. J. Immunol. Methods 290, 51-67.
11. Ohashi, H., Shimizu, Y., Ying, B. W., and Ueda, T. (2007). Efficient protein selection based on ribosome display system with purified components. Biochem Biophys. Res. Commun. 352, 270-276.
12. Studier, F. W. (2005). Protein production by auto-induction in high density shaking cultures. Protein Expr Purif 41, 207-234.
13. Zahnd, C., Amstutz, P., and Plückthun, A. (2007). Ribosome display: selecting and evolving proteins in vitro that specifically bind to a target. Nat. Methods 4, 269-279.

The invention claimed is:

1. A non-naturally occurring protein that binds to the extra-domain B (ED-B) of fibronectin, said protein comprising two monomeric ubiquitin units linked together in a head-to-tail arrangement, wherein:
   (i) each monomeric ubiquitin unit of said protein has at least 85% amino acid sequence identity to the amino acid sequence of SEQ ID NO: 1; and amino acid substitutions selected from the group consisting of positions corresponding to residues 2, 4, 6, 8, 62, 63, 64, 65, and 66 of SEQ ID NO: 1, and further wherein:
      (1) the amino acid substitutions in the first monomeric ubiquitin unit are the amino acid substitutions K6W, L8W, K63R, E64K, S65F, and T66P and the amino acid substitutions in the second monomeric ubiquitin unit are the amino acid substitutions K6T, L8Q, Q62W, K63S, E64N, and T66E, optionally Q2R; or
      (2) the amino acid substitutions in the first monomeric ubiquitin unit are the amino acid substitutions Q2T, F4W, K6H, Q62N, K63F, E64K, S65L, and T66S and the amino acid substitutions in the second monomeric ubiquitin unit are the amino acid substitutions K6X, L8X, Q62X, K63X, E64X, S65X, and T66X, optionally Q2X, wherein X can be any amino acid;
   (ii) said protein has a specific binding affinity to said ED-B domain of fibronectin of $K_d = 10^{-7}$-$10^{-12}$ M; and
   (iii) said protein exhibits a monovalent binding activity with respect to said ED-B domain of fibronectin.

2. The protein according to claim 1, wherein said first and second monomeric ubiquitin units are linked either directly or by a linker.

3. A fusion protein comprising the protein according to claim 1 fused to a pharmaceutically active component or a diagnostic component, wherein said pharmaceutically active component is a cytokine, a chemokine, a cytotoxic compound, or an enzyme; or wherein said diagnostically active component is a fluorescent compound, a photosensitizer, or a radionuclide.

4. The fusion protein according to claim 3, wherein said pharmaceutically active component is TNF-alpha.

5. A pharmaceutical composition comprising the protein of claim 1 and one or more pharmaceutically acceptable carriers or excipients.

6. The pharmaceutical composition of claim 5, further comprising one or more chemotherapeutic agents.

7. The pharmaceutical composition of claim 6, which is in the form of a combined preparation or in the form of a kit.

8. The protein according to claim 2, wherein the linker comprises the amino acid sequence of GIG, RIG, SGGGG (SEQ ID NO: 48), SGGGGIG (SEQ ID NO: 49), or SGGGGSGGGGIG (SEQ ID NO: 32).

9. The pharmaceutical composition of claim 6, wherein the one or more chemotherapeutic agents are selected from the group consisting of melphalan, doxorubicin, cyclophosphamide, dactinomycin, fluorodesoxyuracil, cisplatin, paclitaxel, gemcitabine, a kinase inhibitor, and a radiopharmaceutical.

* * * * *